(12) United States Patent
Helal et al.

(10) Patent No.: US 8,829,010 B2
(45) Date of Patent: Sep. 9, 2014

(54) **PYRAZOLO[3,4-*D*]PYRIMIDINE COMPOUNDS AND THEIR USE AS PDE2 INHIBITORS AND/OR CYP3A4 INHIBITORS**

(75) Inventors: Christopher John Helal, Mystic, CT (US); Thomas Allen Chappie, Carlisle, MA (US); John Michael Humphrey, Mystic, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 14/116,064

(22) PCT Filed: May 24, 2012

(86) PCT No.: PCT/IB2012/052627
§ 371 (c)(1),
(2), (4) Date: Nov. 6, 2013

(87) PCT Pub. No.: WO2012/168817
PCT Pub. Date: Dec. 13, 2012

(65) Prior Publication Data
US 2014/0080806 A1    Mar. 20, 2014

Related U.S. Application Data

(60) Provisional application No. 61/494,070, filed on Jun. 7, 2011.

(51) Int. Cl.
*C07D 487/04* (2006.01)
*A61K 31/519* (2006.01)

(52) U.S. Cl.
CPC .................................. *C07D 487/04* (2013.01)
USPC ........................................ 514/262.1; 544/262

(58) Field of Classification Search
USPC .......................................................... 544/262
See application file for complete search history.

(56) References Cited

U.S. PATENT DOCUMENTS

2006/0154931 A1    7/2006    Verhoest et al.

FOREIGN PATENT DOCUMENTS

| WO | 2006/072615 | 7/2006 |
| WO | 2006072615 | 7/2006 |

OTHER PUBLICATIONS

Boess et al.,Inhibition of phosphodiesterase 2 increases neuronal cGMP, synaptic plasticity and memoryperformance, Neuropharmacology, 47(7):1081-92, 2004.
Brandon et al., Potential CNS Applications for Phosphodiesterase Enzyme Inhibitors, Annual Reports in Medicinal Chemistry 42: 4-5, 2007.
Chen et al., Tetrahedron Lett. 2000, 41, 5453-5456.
Domek-Lopacinska and Strosznajder, The effect of selective inhibition of cyclic GMP hydrolyzing phosphodiesterases 2 and 5 on learning and memory processes and nitric oxide synthetase activity in brain during aging, Brain Research, 1216:68-77,2008.
Dounay et at., Bioorg. Med. Chern. Lett. 2009, 19, 1159-1163.
Erdik, Tetrahedron 1992,48, 9577-9648.
Jackson et al., J. Am. Chern. Soc. 1981, 103,533-540.
Jung and Y. M. Choi, J. Org. Chern. 1991, 56, 6729-6730.
Kayhan et al., The adenosine deaminase inhibitor erythro-9-[2-hydroxyl-3-nonyl]-adenine decreases intestinal permeability and protects against experimental sepsis: a prospective, randomized laboratory investigation, Critical Care, 12(5):R125, 2008.
Littke et al., J. Am. Chern. Soc. 2000, 122, 4020-4028.
Masood et al., Reversal of Oxidative Stress-Induced Anxiety by Inhibition of phosphodiesterase-2 in Mice, JPET 326 (2):369-379,2008.
Masood et al., Anxiolytic effects of phosphodiesterase-2 inhibitors associated with increased cGMP signaling, JPET 331 (2):690-699, 2009.
Obach, et. ai, "Mechanism-Based Inactivation of Human Cytochrome P450 Enzymes and the Prediction of Drug-Drug Interactions," Drug Metabolism and Disposition, vol. 35, No. 2, pp. 246-255, 2007.

(Continued)

*Primary Examiner* — Brian McDowell
(74) *Attorney, Agent, or Firm* — Feng Shao

(57) ABSTRACT

The present invention provides, inter alia, compounds of Formula (I) and pharmaceutically acceptable salts thereof, to processes for the preparation of, intermediates used in the preparation of, and compositions containing such compounds and the uses of such compounds as a method for the treatment of a disease or condition selected from the group consisting of central nervous system disorders, cognitive disorders, schizophrenia, dementia and other disorders in a mammal. The present invention further provides compounds of Formula (Id) and pharmaceutically acceptable salts thereof as CYP3A4 selective inhibitors.

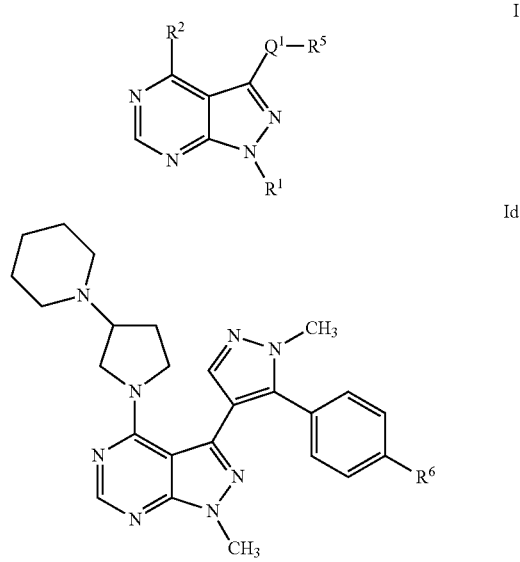

20 Claims, No Drawings

(56) References Cited

OTHER PUBLICATIONS

Podzuweit et al., Isozyme selectiveinhibition of cGMP-stimulated cyclic nucleotide phosphodiesterases by erythro-9-(2-hydroxy-3-nonyl) adenine, Cell Signal, 7(7):733-8, 1995.

Reierson et al., Repeated antidepressant therapy increases cyclic GMP signaling in rat hippocampus, Neurosci. Lett., 466(3): 149-53, 2009.

Rosman et al., Isolation and characterization of human cONAs encoding a cGMP-stimulated 3',5'-cyclic nucleotide phosphodiesterase, Gene, 191 (1 ):89-95, 1997.

Schmidtko et al., cGMP Produced by NO-Sensitive Guanylyl Cyclase Essentially Contributes to Inflammatory and Neuropathic Pain by Using Targets Different from cGMP-Dependent Protein Kinase I, The Journal of Neuroscience, 28 (34):8568-8576, 2008.

Seybold et al., Tumor necrosis factor-{alpha}-dependent expression of phosphodiesterase 2: role in endothelial hyper permeability, Blood, 105:3569-3576, 2005.

Sisko et al., J. Org. Chern. 2000, 65, 1516-1524.

Suzuki, J. Organornet. Chern. 1999,576, 147-168; N. Miyaura and A. Suzuki, Chern. Rev. 1995, 95, 2457-2483.

van Leusen, J. Wildeman, O. H. Oldenziel, J. Org. Chern. 1977, 42, 1153.

Vilsmeier and A. Haack, Ber. 1927, 60, 119-122.

Walsky and Obach, "Validated Assays for Human Cytochrome P450 Activities," Drug Metabolism and Disposition, vol. 32, No. 6, pp. 647-660, 2004.

PYRAZOLO[3,4-D]PYRIMIDINE COMPOUNDS AND THEIR USE AS PDE2 INHIBITORS AND/OR CYP3A4 INHIBITORS

This application is a national phase filing under 35 U.S.C. §371 of international patent application number PCT/IB2012/052627 filed May 24, 2012, which in turn claims the benefit of priority to U.S. Provisional Patent Application Ser. No. 61/494,070 filed Jun. 7, 2011, the disclosure of each of these two applications is hereby incorporated by reference in its entirety.

FIELD OF THE INVENTION

This invention generally relates to pyrazolo[3,4-d]pyrimidines, which are selective inhibitors of PDE2. This invention further relates to certain pyrazolo[3,4-d]pyrimidines, which are selective inhibitors of CYP3A4 (over CYP3A5). The present invention further relates to intermediates for preparation of such compounds; pharmaceutical compositions comprising such compounds; and the use of such compounds in methods for treating central nervous system (CNS) or other disorders described herein. The present invention relates also to methods for treating neurodegenerative or psychiatric disorders, including psychosis, impaired cognition, schizophrenia, depression, dementia and other disorders in a mammal.

BACKGROUND OF THE INVENTION

Phosphodiesterases (PDEs) are a class of intracellular enzymes involved in the hydrolysis of the nucleotides cyclic adenosine monophosphate (cAMP) and cyclic guanosine monophosphate (cGMP) to their respective nucleotide monophosphates. These cyclic nucleotides serve as secondary messengers in several cellular pathways, regulating an array of intracellular processes within neurons of the central nervous system including the activation of cAMP- and cGMP-dependent protein kinases that produce subsequent phosphorylation of proteins involved in regulation of synaptic transmission, synaptic plasticity, neuronal differentiation and survival.

So far, only a single gene for PDE2, PDE2A, has been identified; however, multiple alternatively spliced isoforms of PDE2A, which include PDE2A1, PDE2A2, and PDE2A3, have been reported. PDE2A was identified as a unique family based on primary amino acid sequence and distinct enzymatic activity. The human PDE2A3 sequence was isolated in 1997 (Rosman et al., *Isolation and characterization of human cDNAs encoding a cGMP-stimulated 3',5'-cyclic nucleotide phosphodiesterase*, Gene, 191 (1):89-95, 1997).

Inhibition of PDE2A demonstrates enhanced cognitive function across multiple preclinical models of cognitive performance that reflect improvements in recognition memory, social interactions and working memory, which are all deficient in schizophrenia (Boess et al., *Inhibition of phosphodiesterase 2 increases neuronal cGMP, synaptic plasticity and memory performance*, Neuropharmacology, 47(7):1081-92, 2004). PDE2A inhibition also improved cognitive deficits that develop in aging and Alzheimer's disease (Domek-Lopacinska and Strosznajder, *The effect of selective inhibition of cyclic GMP hydrolyzing phosphodiesterases 2 and 5 on learning and memory processes and nitric oxide synthetase activity in brain during aging*, Brain Research, 1216:68-77, 2008). Bayer has published the biochemical and behavioral profile of BAY 60-7550, reporting a role in PDE2 inhibition in cognitive disorders (Brandon et al., *Potential CNS Applications for Phosphodiesterase Enzyme Inhibitors*, Annual Reports in Medicinal Chemistry 42: 4-5, 2007). This compound showed significant potency at other PDE isoforms and had high clearance and limited brain penetration.

PDE2 inhibitors have also been reported to show efficacy in preclinical models of anxiety and depression (Masood et al., *Anxiolytic effects of phosphodiesterase-2 inhibitors associated with increased cGMP signaling*, JPET 331(2):690-699, 2009; Masood et al., *Reversal of Oxidative Stress-Induced Anxiety by Inhibition of Phosphodiesterase-2 in Mice*, JPET 326(2):369-379, 2008; Reierson et al., *Repeated antidepressant therapy increases cyclic GMP signaling in rat hippocampus*, Neurosci. Lett., 466(3):149-53, 2009).

PDE2A protein expressed in the dorsal horn of the spinal cord and dorsal root ganglia enables PDE2A to modulate cyclic nucleotide levels in these regions during processing of neuropathic and inflammatory pain (Schmidtko et al., *cGMP Produced by NO-Sensitive Guanylyl Cyclase Essentially Contributes to Inflammatory and Neuropathic Pain by Using Targets Different from cGMP-Dependent Protein Kinase I*, The Journal of Neuroscience, 28(34):8568-8576, 2008).

In the periphery, the expression of PDE2A in endothelial cells has been reported to play a critical role in regulation of endothelial barrier function. The expression levels of PDE2A in endothelial cells are increased in response to inflammatory cytokines such as TNF-alpha under conditions of sepsis and acute respiratory distress syndrome, and contribute to disruption of endothelial barrier function. Inhibition of PDE2A has been demonstrated to reverse permeability deficits in sepsis and enhance survival rates in animal models of sepsis and endotoxicosis (Seybold et al., *Tumor necrosis factor-{alpha}-dependent expression of phosphodiesterase 2: role in endothelial hyperpermeability*, Blood, 105:3569-3576, 2005; Kayhan et al., *The adenosine deaminase inhibitor erythro-9-[2-hydroxyl-3-nonyl]-adenine decreases intestinal permeability and protects against experimental sepsis: a prospective, randomized laboratory investigation*, Critical Care, 12 (5):R125, 2008).

At least for the reasons discussed hereinabove, new or improved agents that modulate (such as inhibiting/antagonizing) PDE2 are continually needed for developing new and more effective pharmaceuticals to treat PDE2-associated conditions or diseases or disorders, such as cognitive impairment associated with schizophrenia anxiety, depression, neuropathic pain, inflammatory pain, sepsis, and endotoxicosis, to name a few. In discovering new or improved agents that modulate (such as inhibiting/antagonizing) PDE2, it is also desirable but not required to discover agents with improved chemical or biological properties such as solubility, bioavailability, pharmacokinetics, pharmacodynamics, and/or toxicity. It is also desirable but not required to discover agents with less side effects such as less cardiovascular side effects. In some embodiments, the compounds, compositions, and methods described herein are directed, in part, toward these unmet needs.

Cytochrome P450 enzymes are among the most important enzymes in the metabolism of drugs and other xenobiotics. They comprise a large family of enzymes, of which the most important are the 1A, 2A, 2B, 2C, 2D, 2E, and 3A groups. The drug metabolism reactions catalyzed by these enzymes are mostly oxidations, including hydroxylation, heteroatom dealkylation, and dehydrogenation reactions, among others. These reactions serve to make drugs more hydrophilic (and, hence, more readily excreted) and to add functional groups to molecules that can be subsequently coupled with hydrophilic endogenous entities (such as glucuronic acid or sulfuric acid groups) and excreted. P450 enzymes are a source of interpatient variability of drug pharmacokinetics, due to drug-drug interactions or naturally occurring genetic variants in the structure and/or expression of these enzymes.

Among the many human P450 enzyme families, the CYP3A family is most important, since it is involved in the metabolism of hundreds of compounds. CYP3A has four members in humans: CYP3A4, CYP3A5, CYP3A7, and CYP3A43. CYP3A4 and CYP3A5 are important in the metabolism of drugs. These two enzymes are similar in amino acid sequence, but some differences in substrate profile exist. CYP3A5 is subject to a genetic polymorphism, with some subjects not expressing a functional protein. This can result in interindividual differences in therapy and toxicity.

Because of the importance of CYP3A4 and CYP3A5, it is desirable to develop tools and methods that can be used to distinguish the contribution of each of these enzymes in the metabolism of drugs. Due to their high structural similarity, a tool and method to determine the relative contribution of 3A4 versus 3A5 to the metabolism of a new chemical has not been forthcoming. [See e.g. Obach, et. al, "Mechanism-Based Inactivation of Human Cytochrome P450 Enzymes and the Prediction of Drug-Drug Interactions," Drug Metabolism And Disposition, Vol. 35, No 2, pp 246-255, 2007]. In some embodiments, compounds, compositions, and methods described herein are directed, in part, toward these unmet needs.

SUMMARY OF THE INVENTION

The present invention provides, inter alia, a compound of Formula I:

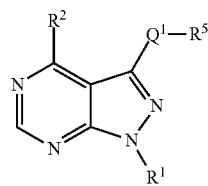

or a pharmaceutically acceptable salt thereof, wherein:
"-$Q^1$-$R^5$" is $Q^{1a}R^5$, $Q^{1b}R^5$, or $Q^{1c}R^5$:

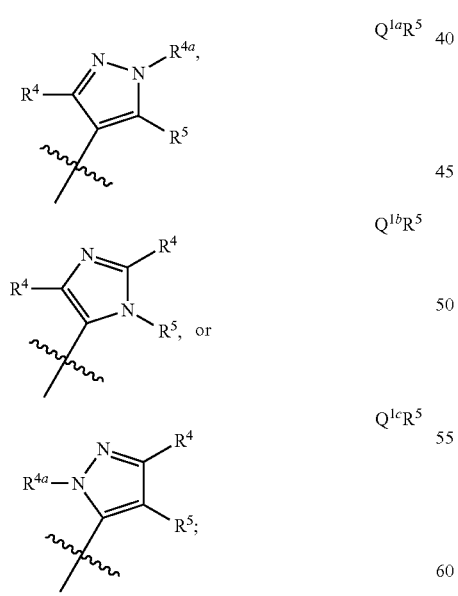

$R^1$ is hydrogen, $(C_1$-$C_6)$alkyl, $(C_3$-$C_4)$alkenyl, $(C_3$-$C_4)$alkynyl, —$CF_3$, —$CHF_2$, —$CH_2F$, or $(C_3$-$C_{15})$cycloalkyl;
$R^2$ is —$NHR^3$ or —$N(R^3)_2$;
each $R^3$ is independently selected from the group consisting of $(C_1$-$C_6)$alkyl, $(C_1$-$C_6)$haloalkyl, $(C_2$-$C_6)$alkenyl, $(C_2$-$C_6)$alkynyl, and $(C_3$-$C_{15})$cycloalkyl, each optionally substituted with 1, 2, 3, 4, or 5 independently selected $R^9$;

or when $R^2$ is —$N(R^3)_2$ both of said $R^3$ may be taken together with the nitrogen atom to which they are attached to form a 4- to 6-membered heterocyclic ring optionally containing one or two oxo groups (O=) and optionally substituted with one to three substituents each independently selected from the group consisting of fluoro, chloro, bromo, —CN, —$CF_3$, —$CHF_2$, —$CH_2F$, —OH, —O—$(C_1$-$C_6)$alkyl, $NH_2$, —NH—$(C_1$-$C_6)$alkyl, —$N[(C_1$-$C_6)$alkyl]$_2$, $(C_1$-$C_6)$alkyl, $(C_2$-$C_6)$alkenyl, $(C_2$-$C_6)$alkynyl, —(C=O)—$R^8$, —(C=O)—$OR^8$, —(C=O)—$N(R^8)_2$, —O—(C=O)—$R^8$, —$OR^8$, —O—(C=O)—$OR^8$, —$SR^8$, —$S(O)R^8$, —$S(O)_2R^8$, —$S(O)_2N(R^8)_2$, —NH—(C=O)—$R^8$, —NH—(C=O)—$OR^8$, —O—(C=O)—$N(R^8)_2$, —NH—(C=O)—$N(R^8)_2$, —$N[(C_1$-$C_6)$alkyl](C=O)—$R^8$, —$N[(C_1$-$C_6)$alkyl](C=O)—$OR^8$, —$N[(C_1$-$C_6)$alkyl](C=O)—$N(R^8)_2$, $(C_3$-$C_{15})$cycloalkyl, $(C_6$-$C_{10})$aryl, $(C_1$-$C_{14})$heterocyclic, and $(C_1$-$C_{13})$heteroaryl; wherein each of said $(C_3$-$C_{15})$cycloalkyl and $(C_1$-$C_{14})$heterocyclic may optionally contain one double or triple bond and may optionally contain one to two oxo (O=) groups, and wherein each of said $(C_3$-$C_{15})$cycloalkyl, $(C_6$-$C_{10})$aryl, $(C_1$-$C_{14})$heterocyclic, and $(C_1$-$C_{13})$heteroaryl is optionally substituted with one to three substituents each independently selected from fluoro, chloro, bromo, —CN, —$CF_3$, —$CHF_2$, —$CH_2F$, —OH, —O—$(C_1$-$C_6)$alkyl, —O—$(C_1$-$C_6)$haloalkyl, $NH_2$, —NH—$(C_1$-$C_6)$alkyl, —$N[(C_1$-$C_6)$alkyl]$_2$, $(C_1$-$C_6)$alkyl, $(C_1$-$C_6)$haloalkyl, $(C_2$-$C_6)$alkenyl, and $(C_2$-$C_6)$alkynyl;

each $R^4$ is independently selected from the group consisting of hydrogen, halo, $(C_1$-$C_6)$alkyl, $(C_2$-$C_6)$alkenyl, $(C_2$-$C_6)$alkynyl, —$CF_3$, —$CHF_2$, —$CH_2F$, and $(C_3$-$C_{15})$cycloalkyl;
$R^{4a}$ is hydrogen, $(C_1$-$C_6)$alkyl, $(C_3$-$C_4)$alkenyl, $(C_3$-$C_4)$alkynyl, —$CF_3$, —$CHF_2$, —$CH_2F$, or $(C_3$-$C_{15})$cycloalkyl;
$R^5$ is $R^{5a}$, $R^{5b}$, $R^{5c}$, $R^{5d}$, $R^{5e}$, $R^{5f}$, or $R^{5g}$:

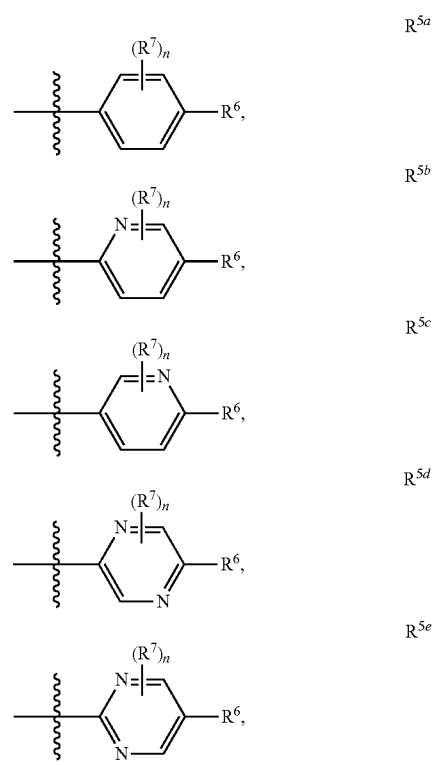

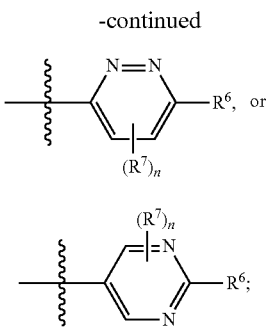

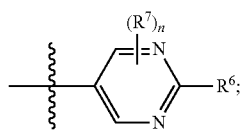

where n is 0, 1, 2, 3, or 4;

$R^6$ is selected from the group consisting of hydrogen, halo, $(C_1-C_6)$alkyl, —$CF_3$, —$CHF_2$, —$CH_2F$, —$CF_2$—$(C_1-C_6)$alkyl, —$SF_5$, —CN, —$(C_1-C_6)$alkyl-CN, —$NO_2$, —(C=O)—$R^8$, —(C=O)—$OR^8$, —$OR^8$, —O—(C=O)—$N(R^8)_2$, —$SR^8$, —$S(O)R^8$, —$S(O)_2R^8$, $NH_2$, —NH—$(C_1$-$C_6)$alkyl, —$N[(C_1-C_6)$alkyl$]_2$, —NH—(C=O)—$R^8$, —NH—(C=O)—$OR^8$, —$N[(C_1-C_6)$alkyl$](C=O)$—$R^8$, —$N[(C_1-C_6)$alkyl$](C=O)$—$OR^8$, $(C_2-C_6)$alkenyl, $(C_2-C_6)$alkynyl, $(C_3-C_{15})$cycloalkyl, $(C_1-C_{14})$heterocyclic, $(C_6-C_{10})$aryl, and $(C_1-C_{13})$heteroaryl; wherein each of said $(C_3-C_{15})$cycloalkyl and $(C_1-C_{14})$heterocyclic optionally contains one double or triple bond and optionally contains one to two oxo (O=) groups;

each $R^7$ is independently selected from the group consisting of halo, $(C_1-C_6)$alkyl, $(C_2-C_6)$alkenyl, $(C_2-C_6)$alkynyl, —CN, —$CF_3$, —$CHF_2$, —$CH_2F$, —O—$(C_1-C_6)$alkyl and $(C_3-C_{15})$cycloalkyl;

or $R^6$ and an adjacent $R^7$, together with the two carbon atoms to which they are attached, form a 5- or 6-membered heteroaryl or a 5- or 6-membered heterocyclic ring, each optionally substituted with one to three substituents each independently selected from fluoro, chloro, bromo, —CN, —$CF_3$, —$CHF_2$, —$CH_2F$, —OH, —O—$(C_1-C_6)$alkyl, —O—$(C_1-C_6)$haloalkyl, $(C_1-C_6)$alkyl, and $(C_1-C_6)$haloalkyl;

or two adjacent $R^7$, together with the two carbon atoms to which they are attached, form a 5- or 6-membered heteroaryl or a 5- or 6-membered heterocyclic ring, each optionally substituted with one to three substituents each independently selected from fluoro, chloro, bromo, —CN, —$CF_3$, —$CHF_2$, —$CH_2F$, —OH, —O—$(C_1-C_6)$alkyl, —O—$(C_1-C_6)$haloalkyl, $(C_1-C_6)$alkyl, and $(C_1-C_6)$haloalkyl;

each $R^8$ wherever it occurs is independently selected from the group consisting of hydrogen, $(C_1-C_6)$alkyl, $(C_3-C_{15})$cycloalkyl, —$(C_1-C_6)$alkyl-$(C_3-C_{15})$cycloalkyl, —$CF_3$, —$CH_2F$, and —$CHF_2$; and each $R^9$ is independently selected from the group consisting of halo, —$CF_3$, —$CHF_2$, —$CH_2F$, —$CF_2$—$(C_1-C_6)$alkyl, —CN, —$(C_1-C_6)$alkyl-CN, —$NO_2$, —(C=O)—$R^8$, —(C=O)—$OR^8$, —$OR^8$, —O—(C=O)—$N(R^8)_2$, —$SR^8$, —$S(O)R^8$, —$S(O)_2R^8$, $NH_2$, —NH—$(C_1-C_6)$alkyl, —$N[(C_1-C_6)$alkyl$]_2$, —NH—(C=O)—$R^8$, —NH—(C=O)—$OR^8$, —$N[(C_1-C_6)$alkyl$](C=O)$—$R^8$, —$N[(C_1-C_6)$alkyl$](C=O)$—$OR^8$, $(C_1-C_6)$alkyl, $(C_2-C_6)$alkenyl, $(C_2-C_6)$alkynyl, $(C_3-C_{15})$cycloalkyl, $(C_1-C_{14})$heterocyclic, $(C_6-C_{10})$aryl, and $(C_1-C_{13})$heteroaryl; wherein each of said $(C_3-C_{15})$cycloalkyl and $(C_1-C_{14})$heterocyclic may optionally contain one double or triple bond and one to two oxo (O=) groups; and wherein each of said $(C_3-C_{15})$cycloalkyl, $(C_1-C_{14})$heterocyclic, $(C_6-C_{10})$aryl, and $(C_1-C_{13})$heteroaryl moieties may be optionally substituted with one to three substituents independently selected from $(C_1-C_6)$alkyl, $(C_1-C_6)$alkoxy, halo, and —$CF_3$.

As used herein, the term "adjacent" in describing the relative positions of two substitution groups on a same ring structure refers to two substitution groups that are respectively attached to two ring-forming atoms of the same ring, wherein the two-ring forming atoms are directly connected through a chemical bond. For example, in the following structure:

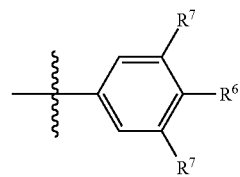

either of the two $R^7$ groups is an adjacent group of $R^6$.

As used herein, the term "n-membered" where n is an integer typically describes the number of ring-forming atoms in a moiety where the number of ring-forming atoms is n. For example, pyridine is an example of a 6-membered heteroaryl ring and thiophene is an example of a 5-membered heteroaryl group.

As used herein, the term "alkyl" is defined to include saturated aliphatic hydrocarbons including straight chains and branched chains. Preferably, the alkyl group has 1 to 6 carbon atoms. For example, as used herein, the term "$(C_1-C_6)$alkyl," as well as the alkyl moieties of other groups referred to herein [e.g., $(C_1-C_6)$alkoxy], refers to linear or branched radicals of 1 to 6 carbon atoms (e.g., methyl, ethyl, n-propyl, isopropyl, n-butyl, isobutyl, sec-butyl, tert-butyl), optionally substituted by 1 to 5 suitable substituents.

Whenever a numerical range associate with carbon atoms is used in this application, for example when 1 to 6 is used in the term of "$(C_1-C_6)$alkyl", it means that the alkyl group may contain 1 carbon atom, 2 carbon atoms, 3 carbon atoms, etc. up to and including 6 carbon atoms; for another example, the term "$(C_1-C_{14})$heterocyclic" refers to a "heterocyclic" group that contains 1 to 14 ring-forming carbon atoms; and the term "$(C_1-C_{13})$heteroaryl" refers to a "heteroaryl" group that contains 1 to 13 ring-forming carbon atoms.

As used herein, the term "alkenyl" is defined to include aliphatic hydrocarbons having at least one carbon-carbon double bond, including straight chains and branched chains having at least one carbon-carbon double bond. Preferably, the alkenyl group has 2 to 6 carbon atoms. More preferably, the alkenyl group has 2 to 4 carbon atoms. For example, as used herein, the term "$(C_2-C_6)$alkenyl" means straight or branched chain unsaturated radicals of 2 to 6 carbon atoms, including, but not limited to, ethenyl, 1-propenyl, 2-propenyl (allyl), isopropenyl, 2-methyl-1-propenyl, 1-butenyl, 2-butenyl, and the like, optionally substituted by 1 to 5 suitable substituents. When the compounds of Formula I contain an alkenyl group, the alkenyl group may exist as the pure E (entgegen) form, the pure Z (zusammen) form, or any mixture thereof.

As used herein, the term "alkynyl" is defined to include aliphatic hydrocarbons having at least one carbon-carbon triple bond, including straight chains and branched chains having at least one carbon-carbon triple bond. Preferably, the alkynyl group has 2 to 6 carbon atoms. For example, as used herein, the term "$(C_2-C_6)$alkynyl" is used herein to mean straight or branched hydrocarbon chain alkynyl radicals as defined above, having 2 to 6 carbon atoms and one triple bond, optionally substituted by 1 to 5 suitable substituents.

As used herein, the term "cycloalkyl" is defined to include saturated or unsaturated (non-aromatic) monocyclic or polycyclic (such as bicyclic) hydrocarbon rings (e.g., monocyclics such as cyclopropyl, cyclobutyl, cyclopentyl, cyclohexyl, cycloheptyl, cyclooctyl, or cyclononyl or bicyclics including bridged or fused systems such as bicyclo[2.2.1]heptanyl, bicyclo[3.2.1]octanyl or bicyclo[5.2.0]nonanyl, etc.), optionally substituted by 1 to 5 suitable substituents. The cycloalkyl group has 3 to 15 carbon atoms. In one embodiment the cycloalkyl may optionally contain one, two or more non-cumulative non-aromatic double or triple bonds and one to three oxo groups. Preferably, the bicycloalkyl group has 6 to 15 carbon atoms. The bicycloalkyl is optionally substituted by 1 to 5 suitable substituents. In one embodiment the bicycloalkyl may optionally contain one, two or more non-cumulative non-aromatic double or triple bonds As used herein, the term "aryl" is defined to include all-carbon monocyclic or fused-ring polycyclic aromatic groups having a conjugated pi-electron system. The aryl group has 6, 8, or 10 carbon atoms in the ring(s). More commonly, the aryl group has 6 or 10 carbon atoms in the ring(s). Most commonly, the aryl group has 6 carbon atoms in the ring. For example, as used herein, the term "($C_6$-$C_{10}$)aryl" means aromatic radicals containing from 6 to 10 carbon atoms such as phenyl, naphthyl, tetrahydronaphthyl, indanyl and the like. The aryl group is optionally substituted by 1 to 5 suitable substituents.

As used herein, the term "heteroaryl" is defined to include monocyclic or fused-ring polycyclic aromatic heterocyclic groups with one or more heteroatom ring members (ring-forming atoms) selected from O, S and N in at least one ring. The heteroaryl group has 5 to 14 ring-forming atoms, including 1 to 13 carbon atoms, and 1 to 8 heteroatoms selected from O, S, and N. Preferably, the heteroaryl group has 5 to 10 ring-forming atoms including one to four heteroatoms. The heteroaryl group can also contain one to three oxo groups. More preferably, the heteroaryl group has 5 to 8 ring-forming atoms including one, two or three heteroatoms. Monocyclic heteroaryls of particular interest include those with 5 ring-forming atoms including one to three heteroatoms or those with 6 ring-forming atoms including one or two nitrogen heteroatoms. Fused bicyclic heteroaryls of particular interest include two fused 5- and/or 6-membered monocyclic rings including one to four heteroatoms.

Suitable heteroaryls include pyridyl, pyrazinyl, pyrimidinyl, pyridazinyl, thienyl, furyl, imidazolyl, pyrrolyl, oxazolyl (e.g., 1,3-oxazolyl, 1,2-oxazolyl), thiazolyl (e.g., 1,2-thiazolyl, 1,3-thiazolyl), pyrazolyl, tetrazolyl, triazolyl (e.g., 1,2,3-triazolyl, 1,2,4-triazolyl), oxadiazolyl (e.g., 1,2,3-oxadiazolyl), thiadiazolyl (e.g., 1,3,4-thiadiazolyl), quinolyl, isoquinolyl, benzothienyl, benzofuryl, indolyl, pyridone, pyrimidone, pyrazinone, pyrimidinone, 1H-imidazol-2(3H)-one, 1H-pyrrole-2,5-dione, and the like. The heteroaryl group is optionally substituted by 1 to 5 suitable substituents.

As used herein, the term "heterocyclic" is defined to include a monocyclic, bridged polycyclic or fused polycyclic, saturated or unsaturated, non-aromatic 3- to 15-membered ring system (such as 4- to 14-membered ring system or 4- to 10-membered ring system), including 1 to 14 ring-forming carbon atoms and 1 to 10 ring-forming heteroatoms selected from O, S and N. The heterocyclic group can also include one to three oxo groups. Examples of such heterocycloalkyl rings include azetidinyl, tetrahydrofuranyl, imidazolidinyl, pyrrolidinyl, piperidinyl, piperazinyl, oxazolidinyl, thiazolidinyl, pyrazolidinyl, thiomorpholinyl, tetrahydrothiazinyl, tetrahydrothiadiazinyl, morpholinyl, oxetanyl, tetrahydrodiazinyl, oxazinyl, oxathiazinyl, indolinyl, isoindolinyl, quinuclidinyl, chromanyl, isochromanyl, benzoxazinyl, 2-azabicyclo[2.2.1]heptanone, 3-azabicyclo[3.1.0]hexane, 3-azabicyclo[4.1.0]heptane and the like. Further examples of said heterocyclic rings include tetrahydrofuran-2-yl, tetrahydrofuran-3-yl, imidazolidin-1-yl, imidazolidin-2-yl, imidazolidin-4-yl, pyrrolidin-1-yl, pyrrolidin-2-yl, pyrrolidin-3-yl, piperidin-1-yl, piperidin-2-yl, piperidin-3-yl, piperidin-4-yl, piperazin-1-yl, piperazin-2-yl, 1,3-oxazolidin-3-yl, isothiazolidine, 1,3-thiazolidin-3-yl, 1,2-pyrazolidin-2-yl, 1,2-tetrahydrothiazin-2-yl, 1,3-tetrahydrothiazin-3-yl, 1,2-tetrahydrodiazin-2-yl, 1,3-tetrahydrodiazin-1-yl, 1,4-oxazin-2-yl, oxazolidinone, and the like. The heterocyclic ring is optionally substituted by 1 to 5 suitable substituents. Preferred heterocyclics include 5- or 6-membered monocyclic rings and 9- or 10-membered fused bicyclic rings.

As used herein, the term "halo" or "halogen" group is defined to include fluorine, chlorine, bromine or iodine.

As used herein, "haloalkyl" refers to an alkyl group having one or more halogen substituents. Examples of haloalkyl groups include, but are not limited to, $CF_3$, $C_2F_5$, $CHF_2$, $CH_2F$, $CH_2CF_3$, and the like.

As used herein, the term "optionally substituted" means that substitution is optional and therefore includes both unsubstituted and substituted atoms and moieties. A "substituted" atom or moiety indicates that any hydrogen on the designated atom or moiety can be replaced with a selection from the indicated substituent group, provided that the normal valency of the designated atom or moiety is not exceeded, and that the substitution results in a stable compound. For example, if a methyl group (i.e., $CH_3$) is optionally substituted, then 3 hydrogen atoms on the carbon atom can be replaced with substituent groups.

As noted above, the compounds of Formula I may exist in the form of pharmaceutically acceptable salts such as, e.g., acid addition salts and base addition salts of the compounds of Formula I. The phrase "pharmaceutically acceptable salt(s)", as used herein, unless otherwise indicated, includes acid addition or base salts which may be present in the compounds of Formula I.

Pharmaceutically acceptable salts of the compounds of Formula I include the acid addition and base salts thereof.

Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulphate and hemicalcium salts.

For a review on suitable salts, see "Handbook of Pharmaceutical Salts: Properties, Selection, and Use" by Stahl and Wermuth (Wiley-VCH, 2002). Methods for making pharmaceutically acceptable salts of compounds of Formula I are known to one of skill in the art.

As used herein the terms "Formula I" and "Formula I or pharmaceutically acceptable salts thereof" are defined to include all forms of the compound of Formula I, including hydrates, solvates, isomers, crystalline and non-crystalline forms, isomorphs, polymorphs, metabolites, and prodrugs thereof.

Compounds of Formula I or pharmaceutically acceptable salt thereof, may exist in unsolvated and solvated forms. When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

The compounds of Formula I may exist as clathrates or other complexes. Included within the scope of the invention are complexes such as clathrates, drug-host inclusion complexes wherein, in contrast to the aforementioned solvates, the drug and host are present in stoichiometric or non-stoichiometric amounts. Also included are complexes of the Formula I containing two or more organic and/or inorganic components which may be in stoichiometric or non-stoichiometric amounts. The resulting complexes may be ionized, partially ionized, or non-ionized. For a review of such complexes, see J. K. Haleblian, *J. Pharm. Sci.* 1975, 64, 1269-1288.

Also included within the scope of the invention are metabolites of compounds of Formula I, that is, compounds formed in vivo upon administration of the drug.

The compounds of Formula I may have asymmetric carbon atoms. The carbon-carbon bonds of the compounds of Formula I may be depicted herein using a solid line (—) a solid wedge ( ▬ ) or a dotted wedge ( ⋯ ). The use of a solid line to depict bonds to asymmetric carbon atoms is meant to indicate that all possible stereoisomers (e.g. specific enantiomers, racemic mixtures, etc.) at that carbon atom are included. The use of either a solid or dotted wedge to depict bonds to asymmetric carbon atoms is meant to indicate that only the stereoisomer shown is meant to be included. It is possible that compounds of Formula I may contain more than one asymmetric carbon atom. In those compounds, the use of a solid line to depict bonds to asymmetric carbon atoms is meant to indicate that all possible stereoisomers are meant to be included. For example, unless stated otherwise, it is intended that the compounds of Formula I can exist as enantiomers and diastereomers or as racemates and mixtures thereof. The use of a solid line to depict bonds to one or more asymmetric carbon atoms in a compound of Formula I and the use of a solid or dotted wedge to depict bonds to other asymmetric carbon atoms in the same compound is meant to indicate that a mixture of diastereomers is present.

Stereoisomers of Formula I include cis and trans isomers, optical isomers such as R and S enantiomers, diastereomers, geometric isomers, rotational isomers, conformational isomers, and tautomers of the compounds of Formula I, including compounds exhibiting more than one type of isomerism; and mixtures thereof (such as racemates and diastereomeric pairs). Also included are acid addition or base addition salts wherein the counterion is optically active, for example, D-lactate or L-lysine, or racemic, for example, DL-tartrate or DL-arginine.

When any racemate crystallizes, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

The compounds of the Formula I may exhibit the phenomena of tautomerism and structural isomerism. For example, the compounds of Formula I may exist in several tautomeric forms, including the enol and imine form, and the keto and enamine form and geometric isomers and mixtures thereof. All such tautomeric forms are included within the scope of the compounds of Formula I. Tautomers may exist as mixtures of a tautomeric set in solution. In solid form, usually one tautomer predominates. Even though one tautomer may be described, the present invention includes all tautomers of the compounds of Formula I.

The present invention also includes isotopically-labeled compounds, which are identical to those recited in Formula I above, but for the fact that one or more atoms are replaced by an atom having an atomic mass or mass number different from the atomic mass or mass number usually found in nature. Examples of isotopes that may be incorporated into compounds of Formula I include isotopes of hydrogen, carbon, nitrogen, oxygen, phosphorus, fluorine and chlorine, such as, but not limited to, $^2H$, $^3H$, $^{13}C$, $^{14}C$, $^{15}N$, $^{17}O$, $^{18}O$, $^{32}P$, $^{35}S$, $^{18}F$, and $^{36}Cl$. Certain isotopically-labeled compounds of Formula I, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically-labeled compounds of Formula I may generally be prepared by carrying out the procedures disclosed in the Schemes and/or in the Examples and Preparations below, by substituting an isotopically-labeled reagent for a non-isotopically-labeled reagent.

A specific embodiment of the present invention is a compound of Formula Ia:

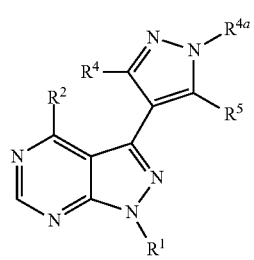

Ia or a pharmaceutically acceptable salt thereof (i.e., a compound of Formula I, or pharmaceutically acceptable salt thereof wherein "-$Q^1$-$R^5$" is $Q^{1a}R^5$).

Another specific embodiment of the present invention is a compound of Formula Ib:

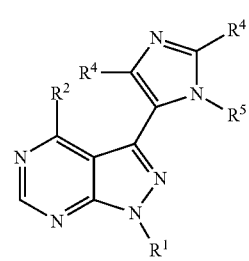

Ib or a pharmaceutically acceptable salt thereof (i.e., a compound of Formula I, or pharmaceutically acceptable salt thereof wherein "-$Q^1$-$R^5$" is $Q^{1b}R^5$).

Another specific embodiment of the present invention is a compound of Formula Ic:

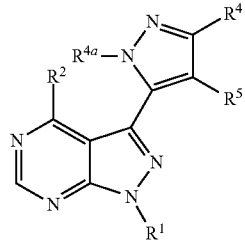

or a pharmaceutically acceptable salt thereof (i.e., a compound of Formula I, or pharmaceutically acceptable salt thereof wherein "-Q¹-R⁵" is Q¹ᶜR⁵).

An embodiment of particular interest is a compound of Formula I (also including Formulae Ia, Ib, and/or Ic), or a pharmaceutically acceptable salt thereof, wherein R¹ is ($C_1$-$C_6$)alkyl; more specifically wherein R¹ is ($C_1$-$C_3$)alkyl; even more specifically wherein R¹ is methyl or ethyl; still more specifically wherein R¹ is methyl.

A specific embodiment of the present invention is a compound of Formula I (also including Formulae Ia, Ib, and/or Ic), or a pharmaceutically acceptable salt thereof, wherein R¹ is hydrogen.

A specific embodiment of the present invention is a compound of Formula I (also including Formulae Ia, Ib, and/or Ic), or a pharmaceutically acceptable salt thereof, wherein R¹ is ($C_3$-$C_4$)alkenyl or ($C_3$-$C_4$)alkynyl.

A specific embodiment of the present invention is a compound of Formula I (also including Formulae Ia, Ib, and/or Ic), or a pharmaceutically acceptable salt thereof, wherein R¹ is methyl, —CF₃, —CHF₂, or —CH₂F.

A specific embodiment of the present invention is a compound of Formula I (also including Formulae Ia, Ib, and/or Ic), or a pharmaceutically acceptable salt thereof, wherein R¹ is —CF₃, —CHF₂, or —CH₂F.

A specific embodiment of the present invention is a compound of Formula I (also including Formulae Ia, Ib, and/or Ic), or a pharmaceutically acceptable salt thereof, wherein R¹ is ($C_3$-$C_{15}$)cycloalkyl, more specifically ($C_3$-$C_6$)cycloalkyl.

A specific embodiment of the present invention is a compound of Formula I (also including Formulae Ia, Ib, and/or Ic), or a pharmaceutically acceptable salt thereof, wherein R² is —NHR³ or —N(R³)₂; and each R³ is independently selected from the group consisting of ($C_1$-$C_6$)alkyl, ($C_1$-$C_6$)haloalkyl, ($C_3$-$C_6$)alkenyl, ($C_3$-$C_6$)alkynyl, and ($C_3$-$C_{15}$)cycloalkyl, each optionally substituted with 1, 2, 3, 4, or 5 independently selected R⁹.

A specific embodiment of the present invention is a compound of Formula I (also including Formulae Ia, Ib, and/or Ic), or a pharmaceutically acceptable salt thereof, wherein:
R² is —N(R³)₂;
each R³ is independently selected from ($C_1$-$C_6$)alkyl;
or both of said R³ may be taken together with the nitrogen atom to which they are attached to form a 4- to 6-membered heterocyclic ring optionally containing one or two oxo groups (O=) and optionally substituted with one to three substituents each independently selected from the group consisting of fluoro, chloro, bromo, —CN, —CF₃, —CHF₂, —CH₂F, —OH, —O—($C_1$-$C_6$)alkyl, NH₂, —NH—($C_1$-$C_6$)alkyl, —N[($C_1$-$C_6$)alkyl]₂, ($C_1$-$C_6$)alkyl, ($C_2$-$C_6$)alkenyl, ($C_2$-$C_6$)alkynyl, —(C=O)—R⁸, —(C=O)—OR⁸, —(C=O)—N(R⁸)₂, —O—(C=O)—R⁸, —OR⁸, —O—(C=O)—OR⁸, —SR⁸, —S(O)R⁸, —S(O)₂R⁸, —S(O)₂N(R⁸)₂, —NH—(C=O)—R⁸, —NH—(C=O)—OR⁸, —O—(C=O)—N(R⁸)₂, —NH—(C=O)—N(R⁸)₂, —N[($C_1$-$C_6$)alkyl](C=O)—R⁸, —N[($C_1$-$C_6$)alkyl]₂, —N[($C_1$-$C_6$)alkyl](C=O)—OR⁸, —N[($C_1$-$C_6$)alkyl](C=O)—N(R⁸)₂, ($C_3$-$C_{15}$)cycloalkyl, ($C_6$-$C_{10}$)aryl, ($C_1$-$C_{14}$)heterocyclic, and ($C_1$-$C_{13}$)heteroaryl; wherein each of said ($C_3$-$C_{15}$)cycloalkyl and ($C_1$-$C_{14}$)heterocyclic may optionally contain one double or triple bond and may optionally contain one to two oxo (O=) groups, and wherein each of said ($C_3$-$C_{15}$)cycloalkyl, ($C_6$-$C_{10}$)aryl, ($C_1$-$C_{14}$)heterocyclic, and ($C_1$-$C_{13}$)heteroaryl is optionally substituted with one to three substituents each independently selected from fluoro, chloro, bromo, —CN, —CF₃, —CHF₂, —CH₂F, —OH, —O—($C_1$-$C_6$)alkyl, —O—($C_1$-$C_6$)haloalkyl, NH₂, —NH—($C_1$-$C_6$)alkyl, —N[($C_1$-$C_6$)alkyl]₂, ($C_1$-$C_6$)alkyl, ($C_1$-$C_6$)haloalkyl, ($C_2$-$C_6$)alkenyl, and ($C_2$-$C_6$)alkynyl.

An embodiment of particular interest is compounds of Formula I (also including Formulae Ia, Ib, and/or Ic), or pharmaceutically acceptable salts thereof, wherein R² is —N(R³)₂ and each R³ is independently ($C_1$-$C_6$)alkyl; more specifically wherein each R³ is independently ($C_1$-$C_3$)alkyl; even more specifically wherein each R³ is independently methyl or ethyl; still more specifically wherein each R³ is methyl.

An embodiment of particular interest is compounds of Formula I (also including Formulae Ia, Ib, and/or Ic), or pharmaceutically acceptable salts thereof, wherein R² is —NHR³; and R³ is ($C_1$-$C_6$)alkyl; more specifically wherein R² is —NH($C_1$-$C_3$)alkyl; even more specifically wherein R² is —NH(CH₃) or —NH(CH₂CH₃).

An embodiment of particular interest is compounds of Formula I (also including Formulae Ia, Ib, and/or Ic), or pharmaceutically acceptable salts thereof, wherein R² is —N(R³)₂; and both of said R³ are taken together with the nitrogen atom to which they are attached to form a 4- to 6-membered heterocyclic ring optionally substituted with one to three substituents each independently selected from the group consisting of fluoro, —CN, —O—($C_1$-$C_6$)alkyl, —N[($C_1$-$C_6$)alkyl]₂, ($C_1$-$C_6$)alkyl, —S(O)₂R⁸, —S(O)₂N(R⁸)₂, —NH—(C=O)—R⁸, —NH—(C=O)—OR⁸, —N[($C_1$-$C_6$)alkyl](C=O)—R⁸, ($C_1$-$C_{14}$)heterocyclic, and ($C_1$-$C_{13}$)heteroaryl; and wherein each of said ($C_1$-$C_{14}$)heterocyclic, and ($C_1$-$C_{13}$)heteroaryl is optionally substituted with one to three substituents each independently selected from ($C_1$-$C_6$)alkyl. In a further embodiment, both of said R³ may be taken together with the nitrogen atom to which they are attached to form an azetidinyl, pyrrolidinyl, or piperidinyl ring, each optionally substituted with one to three substituents each independently selected from the group consisting of fluoro, —CN, —O—($C_1$-$C_6$)alkyl, —N[($C_1$-$C_6$)alkyl]₂, ($C_1$-$C_6$)alkyl, —S(O)₂R⁸, —S(O)₂N(R⁸)₂, —NH—(C=O)—R⁸, —NH—(C=O)—OR⁸, —N[($C_1$-$C_6$)alkyl](C=O)—R⁸, ($C_1$-$C_{14}$)heterocyclic (for example, a 5-, 6-, or 7-membered heterocyclic ring such as pyrrolidinyl or piperidinyl), and ($C_1$-$C_{13}$)heteroaryl (for example, a 5-membered heteroaryl such as pyrazolyl or isoxazolyl); and wherein each of said ($C_1$-$C_{14}$)heterocyclic, and ($C_1$-$C_{13}$)heteroaryl is optionally substituted with one to three substituents each independently selected from ($C_1$-$C_6$)alkyl; and each R⁸ wherever it occurs is independently selected from the group consisting of ($C_1$-$C_6$) alkyl and —($C_1$-$C_6$)alkyl-($C_3$-$C_{15}$)cycloalkyl [for example —($C_1$-$C_2$)alkyl-($C_3$-$C_6$)cycloalkyl such as cyclopropylmethyl].

A specific embodiment of the present invention is a compound of Formula I (also including Formulae Ia, Ib, and/or Ic), or a pharmaceutically acceptable salt thereof, wherein each $R^4$ is independently hydrogen, $(C_1-C_6)$alkyl, —$CF_3$, —$CHF_2$, or —$CH_2F$; more specifically wherein each $R^4$ is independently hydrogen, $(C_1-C_3)$alkyl, —$CF_3$, —$CHF_2$, or —$CH_2F$; even more specifically wherein each $R^4$ is independently hydrogen, methyl, —$CF_3$, —$CHF_2$, or —$CH_2F$; still more specifically wherein each $R^4$ is hydrogen.

A specific embodiment of the present invention is a compound of Formula I (also including Formulae Ia, Ib, and/or Ic), or a pharmaceutically acceptable salt thereof, wherein each $R^{4a}$ is hydrogen, $(C_1-C_6)$alkyl, —$CF_3$, —$CHF_2$, —$CH_2F$, or $(C_3-C_6)$cycloalkyl; more specifically wherein $R^{4a}$ is $(C_1-C_6)$alkyl, —$CF_3$, —$CHF_2$, —$CH_2F$, or $(C_3-C_6)$cycloalkyl; even more specifically wherein $R^{4a}$ is $(C_1-C_6)$alkyl; still more specifically wherein $R^{4a}$ is $(C_1-C_3)$alkyl (particularly methyl).

A specific embodiment of the present invention is a compound of Formula I (also including Formulae Ia, Ib, and/or Ic), or a pharmaceutically acceptable salt thereof, wherein $R^5$ is $R^{5a}$:

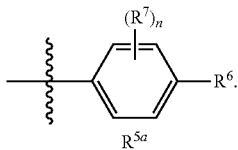

A specific embodiment of the present invention is a compound of Formula I (also including Formulae Ia, Ib, and/or Ic), or a pharmaceutically acceptable salt thereof, wherein $R^5$ is $R^{5b}$:

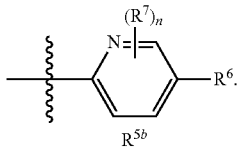

A specific embodiment of the present invention is a compound of Formula I (also including Formulae Ia, Ib, and/or Ic), or a pharmaceutically acceptable salt thereof, wherein $R^5$ is $R^{5c}$:

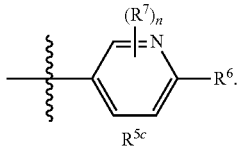

A specific embodiment of the present invention is a compound of Formula I (also including Formulae Ia, Ib, and/or Ic), or a pharmaceutically acceptable salt thereof, wherein $R^5$ is $R^{5d}$:

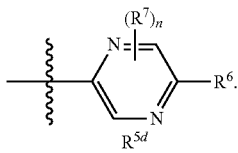

A specific embodiment of the present invention is a compound of Formula I (also including Formulae Ia, Ib, and/or Ic), or a pharmaceutically acceptable salt thereof, wherein $R^5$ is $R^{5e}$:

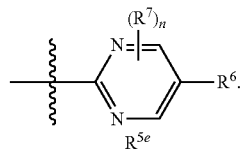

A specific embodiment of the present invention is a compound of Formula I (also including Formulae Ia, Ib, and/or Ic), or a pharmaceutically acceptable salt thereof, wherein $R^5$ is $R^{5f}$:

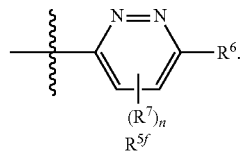

A specific embodiment of the present invention is a compound of Formula I (also including Formulae Ia, Ib, and/or Ic), or a pharmaceutically acceptable salt thereof, wherein $R^5$ is $R^{5g}$:

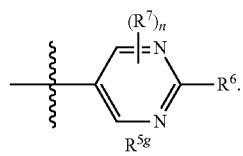

An embodiment of the present invention is a compound of Formula I (including Formula Ia, Ib, and/or Ic, and also including wherein $R^5$ is $R^{5a}$, $R^{5b}$, $R^{5c}$, $R^{5d}$, $R^{5e}$, $R^{5f}$, or $R^{5g}$), or pharmaceutically acceptable salt thereof, wherein:

each $R^6$ is independently selected from the group consisting of hydrogen, halo, $(C_1-C_6)$alkyl, —$CF_3$, —$CHF_2$, —$CH_2F$, —$CF_2$—$(C_1-C_6)$alkyl, —$SF_5$, —$CN$, —$(C_1-C_6)$alkyl-CN, —$NO_2$, —(C=O)—$R^8$, —(C=O)—$OR^8$, —$OR^8$, —O—(C=O)—$N(R^8)_2$, —$SR^8$, —S(O)$R^8$, —S(O)$_2R^8$, $NH_2$, —NH—$(C_1-C_6)$alkyl, —N[$(C_1-C_6)$alkyl]$_2$, —NH—(C=O)—$R^8$, —NH—(C=O)—$OR^8$, —N[$(C_1-C_6)$alkyl](C=O)—$R^8$, —N[$(C_1-C_6)$alkyl](C=O)—$OR^8$, $(C_2-C_6)$alkenyl, $(C_2-C_6)$alkynyl, $(C_3-C_{15})$cycloalkyl, $(C_1-C_{14})$heterocyclic, $(C_6-C_{10})$aryl, and $(C_1-C_{13})$heteroaryl; wherein each of said $(C_3-C_{15})$cycloalkyl and $(C_1-C_{14})$heterocyclic optionally contains one double or triple bond and optionally contains one to two oxo (O=) groups; and each $R^7$ is independently selected from the group consisting of halo, $(C_1-C_6)$alkyl, $(C_2-C_4)$alkenyl, $(C_2-C_6)$alkynyl, —CN, —$CF_3$, —$CHF_2$, —$CH_2F$, —O—$(C_1-C_6)$alkyl and $(C_3-C_{15})$cycloalkyl.

A specific embodiment of the present invention is a compound of Formula I (also including Formulae Ia, Ib, and/or Ic, and also including wherein $R^5$ is $R^{5a}$, $R^{5b}$, $R^{5c}$, $R^{5d}$, $R^{5e}$, $R^{5f}$, or $R^{5g}$), or a pharmaceutically acceptable salt thereof, wherein $R^6$ is hydrogen, halo, —$CF_3$, —$CHF_2$, or —$CH_2F$.

A specific embodiment of the present invention is a compound of Formula I (also including Formulae Ia, Ib, and/or Ic, and also including wherein $R^5$ is $R^{5a}$, $R^{5b}$, $R^{5c}$, $R^{5d}$, $R^{5e}$, $R^{5f}$, or $R^{5g}$), or a pharmaceutically acceptable salt thereof, wherein $R^6$ is —(C=O)—$R^8$, —(C=O)—$OR^8$, —$OR^8$, —O—(C=O)—$N(R^8)_2$, —$SR^8$, —S(O)$R^8$, —S(O)$_2R^8$, $NH_2$, $-NH-(C_1-C_6)$alkyl, $-N[(C_1-C_6)$alkyl$]_2$, $-NH-(C=O)-R^8$, $-NH-(C=O)-OR^8$, $-O-(C=O)-N(R^8)_2$, $-N[(C_1-C_6)$alkyl$]-(C=O)-R^8$, or $-N[(C_1-C_6)$alkyl$]-(C=O)-OR^8$.

A specific embodiment of the present invention is a compound of Formula I (also including Formulae Ia, Ib, and/or Ic, and also including wherein $R^5$ is $R^{5a}$, $R^{5b}$, $R^{5c}$, $R^{5d}$, $R^{5e}$, $R^{5f}$, or $R^{5g}$), or a pharmaceutically acceptable salt thereof, wherein $R^6$ is $(C_1-C_6)$alkyl or $(C_3-C_{15})$cycloalkyl.

In an embodiment of a compound of any one of Formula I, Ia, Ib, or Ic (including wherein $R^5$ is $R^{5a}$, $R^{5b}$, $R^{5c}$, $R^{5d}$, $R^{5e}$, $R^{5f}$, or $R^{5g}$), or a pharmaceutically acceptable salt thereof, $R^6$ is $(C_2-C_6)$alkenyl, $(C_2-C_6)$alkynyl, $(C_1-C_{14})$heterocyclic, $(C_6-C_{10})$aryl, or $(C_1-C_{13})$heteroaryl.

A specific embodiment of the present invention is a compound of Formula I (also including Formulae Ia, Ib, and/or Ic, and also including wherein $R^5$ is $R^{5a}$, $R^{5b}$, $R^{5c}$, $R^{5d}$, $R^{5e}$, $R^{5f}$, or $R^{5g}$), or a pharmaceutically acceptable salt thereof, wherein $R^6$ is selected from the group consisting of halo (F, Br, or Cl), $(C_1-C_6)$alkyl [for example, $(C_1-C_4)$alkyl such as methyl, ethyl, or 2-propyl], $-CF_3$, $-CHF_2$, $-OR^8$ [for example, $(C_1-C_6)$alkoxy such as methoxy], $(C_3-C_{15})$cycloalkyl [for example, $(C_3-C_6)$cycloalkyl such as cyclopropyl].

A specific embodiment of the present invention is a compound of Formula I (also including Formulae Ia, Ib, and/or Ic, and also including wherein $R^5$ is $R^{5a}$, $R^{5b}$, $R^{5c}$, $R^{5d}$, $R^{5e}$, $R^{5f}$, or $R^{5g}$), or a pharmaceutically acceptable salt thereof, wherein each $R^7$ is independently selected from the group consisting of halo and $(C_1-C_6)$alkyl [for example, $(C_1-C_4)$alkyl such as methyl or ethyl].

An embodiment of the present invention is a compound of Formula I (and also including wherein $R^5$ is $R^{5a}$, $R^{5b}$, $R^{5c}$, $R^{5d}$, $R^{5e}$, $R^{5f}$, or $R^{5g}$), or pharmaceutically acceptable salt thereof, wherein $R^6$ and an adjacent $R^7$, together with the two carbon atoms to which they are attached, form a 5- or 6-membered heteroaryl or a 5- or 6-membered heterocyclic ring, each optionally substituted with one to three substituents each independently selected from fluoro, chloro, bromo, $-CN$, $-CF_3$, $-CHF_2$, $-CH_2F$, $-OH$, $-O-(C_1-C_6)$alkyl, $-O-(C_1-C_6)$haloalkyl, $(C_1-C_6)$alkyl, and $(C_1-C_6)$haloalkyl. In a further embodiment of $R^5$, $R^6$ and an adjacent $R^7$, together with the two carbon atoms to which they are attached, can form any one of the following $R^5$ moieties:

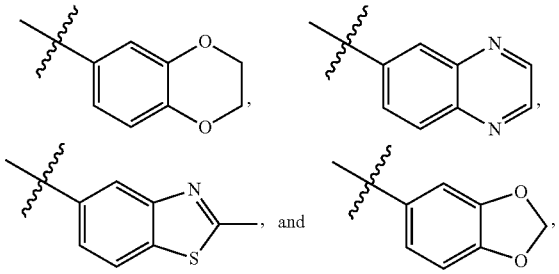

An embodiment of the present invention is a compound of Formula I, or pharmaceutically acceptable salt thereof, wherein two adjacent $R^7$, together with the two carbon atoms to which they are attached, form a 5- or 6-membered heteroaryl or a 5- or 6-membered heterocyclic ring, each optionally substituted with one to three substituents each independently selected from fluoro, chloro, bromo, $-CN$, $-CF_3$, $-CHF_2$, $-CH_2F$, $-OH$, $-O-(C_1-C_6)$alkyl, $-O-(C_1-C_6)$haloalkyl, $(C_1-C_6)$alkyl, and $(C_1-C_6)$haloalkyl. In a further embodiment of $R^5$, two adjacent $R^7$, together with the two carbon atoms to which they are attached, can form any one of the following $R^5$ moieties:

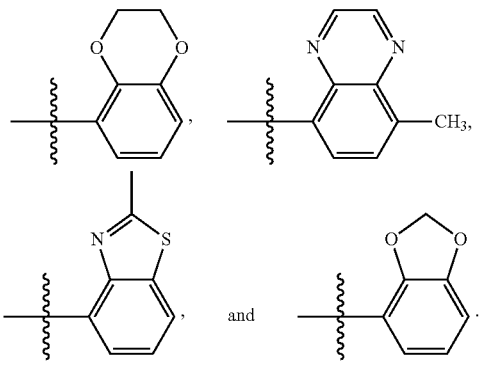

A specific embodiment of the present invention is a compound of Formula I (also including Formulae Ia, Ib, and/or Ic), or a pharmaceutically acceptable salt thereof, wherein each $R^8$ wherever it occurs is independently selected from the group consisting of $(C_1-C_6)$alkyl [for example, $(C_1-C_4)$alkyl such as methyl, ethyl, 2-propyl, or tert-butyl] and $-(C_1-C_6)$alkyl-$(C_3-C_{15})$cycloalkyl [for example, $-(C_1-C_2)$alkyl-$(C_3-C_6)$cycloalkyl such as cyclopropylmethyl].

A specific embodiment of the present invention is a compound of Formula I (also including Formulae Ia, Ib, and/or Ic), or a pharmaceutically acceptable salt thereof, wherein each $R^9$ is independently selected from the group consisting of hydrogen, halo (such as F, Cl, or Br), $-CF_3$, $-CHF_2$, $-CH_2F$, $-CF_2-(C_1-C_6)$alkyl, $-CN$, or $-O-(C_1-C_6)$alkyl; more specifically wherein each $R^9$ is independently hydrogen or halo; even more specifically each $R^9$ is hydrogen.

A specific embodiment of the present invention is a compound of Formula I (also including Formulae Ia, Ib, and/or Ic), or a pharmaceutically acceptable salt thereof, wherein n is 0, 1, or 2.

A specific embodiment of the present invention is a compound of Formula I, or pharmaceutically acceptable salt thereof, wherein "-$Q^1$-$R^5$" is $Q^{1a}R^5$ or $Q^{1b}R^5$. In a further embodiment, each $R^4$ is hydrogen; $R^{4a}$ is $(C_1-C_6)$alkyl (for example, methyl or ethyl); and $R^5$ is $R^{5a}$ or $R^{5b}$.

A specific embodiment of the present invention is a compound of Formula I, or pharmaceutically acceptable salt thereof, wherein:

"-$Q^1$-$R^5$" is $Q^{1a}R^5$ or $Q^{1b}R^5$;

$R^1$ is $(C_1-C_6)$alkyl;

$R^2$ is $-NHR^3$ or $-N(R^3)_2$;

each $R^3$ is independently $(C_1-C_6)$alkyl;

or both of said $R^3$ may be taken together with the nitrogen atom to which they are attached to form a 4- to 6-membered heterocyclic ring optionally substituted with one to three substituents each independently selected from the group consisting of fluoro, $-CN$, $-O-(C_1-C_6)$alkyl, $-N[(C_1-C_6)$alkyl$]_2$, $(C_1-C_6)$alkyl, $-S(O)_2R^8$, $-S(O)_2N(R^8)_2$, $-NH-(C=O)-R^8$, $-NH-(C=O)-OR^8$, $-N[(C_1-C_6)$alkyl$](C=O)-R^8$, $(C_1-C_{14})$heterocyclic, and $(C_1-C_{13})$heteroaryl; and wherein each of said $(C_1-C_{14})$heterocyclic, and $(C_1-C_{13})$heteroaryl is optionally substituted with one to three substituents each independently selected from $(C_1-C_6)$alkyl;

each $R^4$ is hydrogen;

$R^{4a}$ is $(C_1-C_6)$alkyl;

$R^5$ is $R^{5a}$ or $R^{5b}$;

$R^6$ is selected from the group consisting of halo, $(C_1-C_6)$alkyl, $-CF_3$, $-CHF_2$, $-OR^8$, and $(C_3-C_{15})$cycloalkyl;

each $R^7$ is independently selected from the group consisting of halo and $(C_1-C_6)$alkyl;

each $R^8$ wherever it occurs is independently selected from the group consisting of $(C_1-C_6)$alkyl and —$(C_1-C_6)$alkyl-$(C_3-C_{15})$cycloalkyl;

each $R^9$ is hydrogen; and n is 0, 1, or 2.

A specific embodiment of the present invention is a compound of Formula I, or pharmaceutically acceptable salt thereof, wherein:

$R^6$ is selected from the group consisting of hydrogen, halo, $(C_1-C_6)$alkyl, —$CF_3$, —$CHF_2$, —$CH_2F$, —$CF_2$—$(C_1-C_6)$alkyl, —$SF_5$, —CN, —$(C_1-C_6)$alkyl-CN, —$NO_2$, —(C=O)—$R^8$, —(C=O)—$OR^8$, —O—(C=O)—$N(R^8)_2$, —$SR^8$, —$S(O)R^8$, —$S(O)_2R^8$, $NH_2$, —NH—$(C_1-C_6)$alkyl, —$N[(C_1-C_6)$alkyl$]_2$, —NH—(C=O)—$R^8$, —NH—(C=O)—$OR^8$, —$N[(C_1-C_6)$alkyl$](C=O)—R^8$, —$N[(C_1-C_6)$alkyl$](C=O)—OR^8$, $(C_2-C_6)$alkenyl, $(C_2-C_6)$alkynyl, $(C_3-C_{15})$cycloalkyl, $(C_1-C_{14})$heterocyclic, $(C_6-C_{10})$aryl, and $(C_1-C_{13})$heteroaryl; wherein each of said $(C_3-C_{15})$cycloalkyl and $(C_1-C_{14})$heterocyclic optionally contains one double or triple bond and optionally contains one to two oxo (O=) groups; and each $R^7$ is independently selected from the group consisting of halo, $(C_1-C_6)$alkyl, $(C_2-C_4)$alkenyl, $(C_2-C_6)$alkynyl, —CN, —$CF_3$, —$CHF_2$, —$CH_2F$, —O—$(C_1-C_6)$alkyl and $(C_3-C_{15})$cycloalkyl.

A specific embodiment of the present invention is a compound of Formula I, or pharmaceutically acceptable salt thereof, wherein:

"$Q^1$-$R^5$" is $Q^{1a}R^5$:

$Q^{1a}R^5$;

$R^1$ is $(C_1-C_6)$alkyl;

each $R^3$ is independently selected from the group consisting of $(C_1-C_6)$alkyl, $(C_2-C_6)$alkenyl, $(C_2-C_6)$alkynyl, and $(C_3-C_{15})$cycloalkyl, each optionally substituted with 1, 2, or 3 independently selected $R^9$;

or when $R^2$ is —$N(R^3)_2$ both of said $R^3$ may be taken together with the nitrogen atom to which they are attached to form a 4- to 6-membered heterocyclic ring optionally containing one or two oxo groups (O=), and optionally may be substituted with one to three substituents each independently selected from the group consisting of fluoro, —CN, —$CF_3$, —$CHF_2$, —$CH_2F$, —OH, —O—$(C_1-C_6)$alkyl, $NH_2$, —NH—$(C_1-C_6)$alkyl, —$N[(C_1-C_6)$alkyl$]_2$, $(C_1-C_6)$alkyl, $(C_2-C_6)$alkenyl, $(C_2-C_6)$alkynyl, —(C=O)—$R^8$, —(C=O)—$OR^8$, —(C=O)—$N(R^8)_2$, —O—(C=O)—$R^8$, —$OR^8$, —O—(C=O)—$OR^8$, —$SR^8$, —$S(O)R^8$, —$S(O)_2R^8$, —$S(O)_2N(R^8)_2$, —NH—(C=O)—$R^8$, —NH—(C=O)—$OR^8$, —O—(C=O)—$N(R^8)_2$, —NH—(C=O)—$N(R^8)_2$, —$N[(C_1-C_6)$alkyl$](C=O)—R^8$, —$N[(C_1-C_6)$alkyl$](C=O)—OR^8$, —$N[(C_1-C_6)$alkyl$](C=O)—N(R^8)_2$, $(C_3-C_{15})$cycloalkyl, $(C_6-C_{10})$aryl, $(C_1-C_{14})$heterocyclic, and $(C_1-C_{13})$heteroaryl; wherein each of said $(C_3-C_{15})$cycloalkyl and $(C_1-C_{14})$heterocyclic optionally contains one double or triple bond and optionally contains one to two oxo (O=) groups, and wherein each of said $(C_3-C_{15})$cycloalkyl, $(C_6-C_{10})$aryl, $(C_1-C_{14})$heterocyclic, and $(C_1-C_{13})$heteroaryl is optionally substituted with one to three substituents each independently selected from fluoro, chloro, bromo, —CN, —$CF_3$, —$CHF_2$, —$CH_2F$, —OH, —O—$(C_1-C_6)$alkyl, —O—$(C_1-C_6)$haloalkyl, $NH_2$, —NH—$(C_1-C_6)$alkyl, —$N[(C_1-C_6)$alkyl$]_2$, $(C_1-C_6)$alkyl, $(C_1-C_6)$haloalkyl, $(C_2-C_6)$alkenyl, and $(C_2-C_6)$alkynyl;

$R^4$ is hydrogen;

$R^{4a}$ is $(C_1-C_6)$alkyl; and $R^5$ is $R^{5a}$, $R^{5b}$, $R^{5c}$, or $R^{5d}$:

$R^{5a}$ $R^{5b}$ $R^{5c}$ or $R^{5d}$, where n is 0, 1, 2, 3, or 4.

A specific embodiment of the present invention is a compound of Formula Ia, or pharmaceutically acceptable salt thereof, wherein:

$R^1$ is methyl, —$CF_3$, —$CHF_2$, or —$CH_2F$;

$R^2$ is —$N(R^3)_2$, wherein both of said $R^3$ are taken together with the nitrogen atom to which they are attached to form an optionally substituted 4- to 6-membered heterocyclic ring that is a moiety of the "$Q^{1a}R^5$" moiety of is a moiety of each of $R^{20a}$ and $R^{20b}$ is independently $(C_1-C_3)$alkyl (for example methyl or ethyl);

or $R^{20a}$ and $R^{20b}$, together with the nitrogen atom to which they are attached, form a 5- or 6-membered heterocyclic ring (such as pyrrolidinyl or piperidinyl); and $R^6$ is methyl, ethyl, or Cl.

A specific embodiment of the present invention is a compound of Formula Ia, or pharmaceutically acceptable salt thereof, wherein:

$R^1$ is methyl, —$CF_3$, —$CHF_2$, or —$CH_2F$;

$R^2$ is —$N(R^3)_2$, wherein both of said $R^3$ are taken together with the nitrogen atom to which they are attached to form an optionally substituted 4- to 6-membered heterocyclic ring that is a moiety of

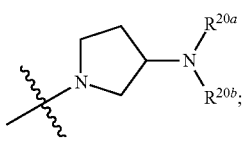

the "$Q^{1a}R^5$" moiety of

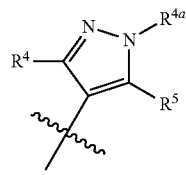

is a moiety of

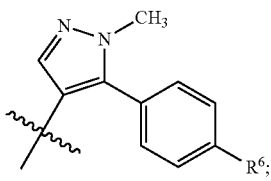

$R^{20a}$ and $R^{20b}$, together with the nitrogen atom to which they are attached, form pyrrolidinyl or piperidinyl; and $R^6$ is methyl, ethyl, or Cl.

A specific embodiment of the present invention is a compound of Formula Id:

Id

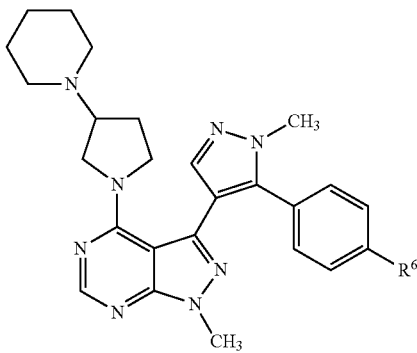

or a pharmaceutically acceptable salt thereof, wherein $R^6$ is methyl, ethyl, or Cl.

A specific embodiment of the present invention is a compound of Formula Id or pharmaceutically acceptable salt thereof, wherein $R^6$ is methyl or ethyl. In a further embodiment, $R^6$ is methyl.

A specific embodiment of the present invention is a compound of Formula Ib, or a pharmaceutically acceptable salt thereof, wherein:

$R^1$ is methyl, —$CF_3$, —$CHF_2$, or —$CH_2F$;

$R^2$ is —$N(R^3)_2$, wherein both of said $R^3$ are taken together with the nitrogen atom to which they are attached to form an optionally substituted 4- to 6-membered heterocyclic ring that is a moiety of

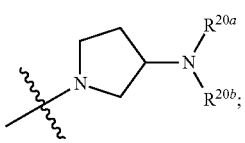

the "$Q^{1b}R^5$" moiety of

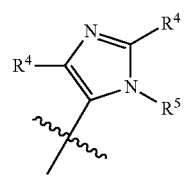

is a moiety of

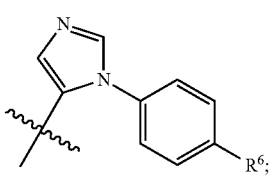

each of $R^{20a}$ and $R^{20b}$ is independently ($C_1$-$C_3$)alkyl (for example methyl or ethyl);

or $R^{20a}$ and $R^{20b}$, together with the nitrogen atom to which they are attached, form a 5- or 6-membered heterocyclic ring [for example pyrrolidinyl or piperidinyl]; and $R^6$ is methyl, ethyl, or Cl.

In another embodiment, the invention also is the compounds described as Examples 1-60 in the Examples section of the subject application, and pharmaceutically acceptable salts thereof.

In another embodiment the invention is a compound that is:

4-(azetidin-1-yl)-1-methyl-3-[1-methyl-5-(4-methylphenyl)-1H-pyrazol-4-yl]-1H-pyrazolo[3,4-d]pyrimidine;

3-[5-(4-cyclopropylphenyl)-1-methyl-1H-pyrazol-4-yl]-4-(3-fluoroazetidin-1-yl)-1-methyl-1H-pyrazolo[3,4-d]pyrimidine;

4-(azetidin-1-yl)-1-methyl-3-{1-methyl-5-[5-(trifluoromethyl)pyridin-2-yl]-1H-pyrazol-4-yl}-1H-pyrazolo[3,4-d]pyrimidine;

4-(azetidin-1-yl)-3-{5-[4-(difluoromethyl)phenyl]-1-methyl-1H-pyrazol-4-yl}-1-methyl-1H-pyrazolo[3,4-d]pyrimidine;

3-[5-(4-ethylphenyl)-1-methyl-1H-pyrazol-4-yl]-4-(3-fluoroazetidin-1-yl)-1-methyl-1H-pyrazolo[3,4-d]pyrimidine;

4-(azetidin-1-yl)-3-[5-(4-ethylphenyl)-1-methyl-1H-pyrazol-4-yl]-1-methyl-1H-pyrazolo[3,4-d]pyrimidine;
methyl (1-{3-[5-(4-cyclopropylphenyl)-1-methyl-1H-pyrazol-4-yl]-1-methyl-1H-pyrazolo[3,4-d]pyrimidin-4-yl}azetidin-3-yl)carbamate;
4-(azetidin-1-yl)-3-[5-(4-cyclopropylphenyl)-1-methyl-1H-pyrazol-4-yl]-1-methyl-1H-pyrazolo[3,4-d]pyrimidine;
4-(azetidin-1-yl)-3-[5-(3-fluoro-4-methoxyphenyl)-1-methyl-1H-pyrazol-4-yl]-1-methyl-1H-pyrazolo[3,4-d]pyrimidine;
4-(azetidin-1-yl)-1-methyl-3-{1-methyl-5-[4-(trifluoromethyl)phenyl]-1H-pyrazol-4-yl}-1H-pyrazolo[3,4-d]pyrimidine;
4-(3,3-difluoroazetidin-1-yl)-1-methyl-3-{1-methyl-5-[4-(trifluoromethyl)phenyl]-1H-pyrazol-4-yl}-1H-pyrazolo[3,4-d]pyrimidine;
4-(3-fluoroazetidin-1-yl)-1-methyl-3-{1-methyl-5-[4-(trifluoromethyl)phenyl]-1H-pyrazol-4-yl}-1H-pyrazolo[3,4-d]pyrimidine;
4-(azetidin-1-yl)-3-[5-(4-bromophenyl)-1-methyl-1H-pyrazol-4-yl]-1-methyl-1H-pyrazolo[3,4-d]pyrimidine;
4-(3,3-difluoroazetidin-1-yl)-3-[5-(4-ethylphenyl)-1-methyl-1H-pyrazol-4-yl]-1-methyl-1H-pyrazolo[3,4-d]pyrimidine;
3-[5-(4-cyclopropylphenyl)-1-methyl-1H-pyrazol-4-yl]-4-(3,3-difluoroazetidin-1-yl)-1-methyl-1H-pyrazolo[3,4-d]pyrimidine; or
3-{5-[4-(difluoromethyl)phenyl]-1-methyl-1H-pyrazol-4-yl}-4-(3-fluoroazetidin-1-yl)-1-methyl-1H-pyrazolo[3,4-d]pyrimidine,
or a pharmaceutically acceptable salt thereof.

In another embodiment the invention is a compound of Formula Id that is 1-methyl-3-[1-methyl-5-(4-methylphenyl)-1H-pyrazol-4-yl]-4-[(3S)-3-(piperidin-1-yl)pyrrolidin-1-yl]-1H-pyrazolo[3,4-d]pyrimidine, or a pharmaceutically acceptable salt thereof.

The present invention also provides compositions comprising a compound of Formula I or an acceptable salt thereof (e.g., pharmaceutical compositions). Accordingly, in one embodiment, the invention provides a pharmaceutical composition comprising a compound of Formula I or a pharmaceutically acceptable salt thereof, optionally including a pharmaceutically acceptable carrier and, optionally, at least one additional medicinal or pharmaceutical agent. In one embodiment, the additional medicinal or pharmaceutical agent is an anti-schizophrenia agent as described below.

The pharmaceutically acceptable carrier may comprise any conventional pharmaceutical carrier or excipient. Suitable pharmaceutical carriers include inert diluents or fillers, water and various organic solvents (such as hydrates and solvates). The pharmaceutical compositions may, if desired, contain additional ingredients such as flavorings, binders, excipients and the like. Thus for oral administration, tablets containing various excipients, such as citric acid, may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Non-limiting examples of materials, therefore, include lactose or milk sugar and high molecular weight polyethylene glycols. When aqueous suspensions or elixirs are desired for oral administration, the active compound therein may be combined with various sweetening or flavoring agents, coloring matters or dyes and, if desired, emulsifying agents or suspending agents, together with diluents such as water, ethanol, propylene glycol, glycerin, or combinations thereof.

The pharmaceutical composition may, for example, be in a form suitable for oral administration as a tablet, capsule, pill, powder, sustained release formulation, solution or suspension, for parenteral injection as a sterile solution, suspension or emulsion, for topical administration as an ointment or cream or for rectal administration as a suppository.

Exemplary parenteral administration forms include solutions or suspensions of active compounds in sterile aqueous solutions, for example, aqueous propylene glycol or dextrose solutions. Such dosage forms may be suitably buffered, if desired.

The pharmaceutical composition may be in unit dosage forms suitable for single administration of precise dosages. One of ordinary skill in the art would appreciate that the composition may be formulated in sub-therapeutic dosage such that multiple doses are envisioned.

In one embodiment the composition comprises a therapeutically effective amount of a compound of Formula I and optionally including a pharmaceutically acceptable carrier.

Another embodiment of the invention includes a method for the treating of schizophrenia or psychosis in a mammal, preferably a human, comprising administering to said mammal (preferably a human) a therapeutically effective amount of a compound of Formula I or pharmaceutically acceptable salt thereof.

Another embodiment of the invention includes a method for treating a PDE2-mediated (or PDE2-associated) disorder, comprising administering to a mammal (preferably a human) in need thereof an amount of a compound of Formula I effective in inhibiting PDE2; more preferably, administering an amount of a compound of Formula I effective in selectively inhibiting PDE2.

Another embodiment of the invention provides a method for treating neurological disorders (such as migraine; epilepsy; Alzheimer's disease; Parkinson's disease; brain injury; stroke; cerebrovascular diseases (including cerebral arteriosclerosis, cerebral amyloid angiopathy, hereditary cerebral hemorrhage, and brain hypoxia-ischemia); cognitive disorders (including amnesia, senile dementia, HIV-associated dementia, Alzheimer's-associated dementia, Huntington's-associated dementia, Lewy body dementia, vascular dementia, drug-related dementia, delirium, and mild cognitive impairment); mental deficiency (including Down syndrome and fragile X syndrome); sleep disorders (including hypersomnia, circadian rhythm sleep disorder, insomnia, parasomnia, and sleep deprivation) and psychiatric disorders (such as anxiety (including acute stress disorder, generalized anxiety disorder, social anxiety disorder, panic disorder, post-traumatic stress disorder and obsessive-compulsive disorder); factitious disorder (including acute hallucinatory mania); impulse control disorders (including compulsive gambling and intermittent explosive disorder); mood disorders (including bipolar I disorder, bipolar II disorder, mania, mixed affective state, major depression, chronic depression, seasonal depression, psychotic depression, and postpartum depression); psychomotor disorders; psychotic disorders (including schizophrenia, schizoaffective disorder, schizophreniform, and delusional disorder); drug dependence (including narcotic dependence, alcoholism, amphetamine dependence, cocaine addiction, nicotine dependence, and drug withdrawal syndrome); eating disorders (including anorexia, bulimia, binge eating disorder, hyperphagia, and pagophagia); and pediatric psychiatric disorders (including attention deficit disorder, attention deficit/hyperactive disorder, conduct disorder, and autism) in a mammal, preferably a human, comprising administering to said mammal a therapeutically effective amount of a compound of Formula I or a pharmaceutically acceptable salt thereof.

Another embodiment of the invention includes a method for the treatment of schizophrenia.

Another embodiment of the invention includes a method for the treatment of cognitive impairment associated with schizophrenia.

The term "therapeutically effective amount" as used herein refers to that amount of the compound being administered which will relieve to some extent one or more of the symptoms of the disorder being treated. In reference to the treatment of schizophrenia, a therapeutically effective amount refers to that amount which has the effect of relieving to some extent (or, preferably, eliminating) one or more symptoms associated with schizophrenia.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined herein. The term "treating" also includes adjuvant and neoadjuvant treatment of a subject.

Administration of the compounds of Formula I may be effected by any method that enables delivery of the compounds to the site of action. These methods include oral routes, intranasal routes, inhaled routes, intraduodenal routes, parenteral injection (including intravenous, subcutaneous, intramuscular, intravascular or infusion), topical, and rectal administration.

In one embodiment of the present invention, the compounds of Formula I may be preferably administered/effected by oral routes.

Dosage regimens may be adjusted to provide the optimum desired response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form, as used herein, refers to physically discrete units suited as unitary dosages for the mammalian subjects to be treated; each unit containing a predetermined quantity of active compound calculated to produce the desired therapeutic effect in association with the required pharmaceutical carrier. The specifications for the dosage unit forms of the invention are dictated by and directly dependent on (a) the unique characteristics of the chemotherapeutic agent and the particular therapeutic or prophylactic effect to be achieved, and (b) the limitations inherent in the art of compounding such an active compound for the treatment of sensitivity in individuals. In one embodiment of the present invention, the compounds of Formula I may preferably be used to treat humans.

It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. For example, doses may be adjusted based on pharmacokinetic or pharmacodynamic parameters, which may include clinical effects such as toxic effects and/or laboratory values. Thus, the present invention encompasses intra-patient dose-escalation as determined by the skilled artisan. Determining appropriate dosages and regimens for administration of the chemotherapeutic agent is well-known in the relevant art and would be understood to be encompassed by the skilled artisan once provided the teachings disclosed herein.

The amount of the compound of Formula I administered will be dependent on the subject being treated, the severity of the disorder or condition, the rate of administration, the disposition of the compound and the discretion of the prescribing physician. However, an effective dosage is in the range of about 0.01 to about 50 mg per kg body weight per day, preferably about 0.01 to about 5 mg/kg/day, in single or divided doses. For a 70 kg human, this would amount to about 0.7 mg to about 3500 mg/day, preferably about 5 mg to about 2000 mg/day. In some instances, dosage levels below the lower limit of the aforesaid range may be more than adequate, while in other cases still larger doses may be employed without causing any harmful side effect, provided that such larger doses are first divided into several small doses for administration throughout the day.

As used herein, the term "combination therapy" refers to the administration of a compound of Formula I together with an at least one additional pharmaceutical or medicinal agent (e.g., an anti-schizophrenia agent), either sequentially or simultaneously.

As noted above, the compounds of Formula I may be used in combination with one or more additional anti-schizophrenia agents which are described below. When a combination therapy is used, the one or more additional anti-schizophrenia agents may be administered sequentially or simultaneously with the compound of the invention. In one embodiment, the additional anti-schizophrenia agent is administered to a mammal (e.g., a human) prior to administration of the compound of the invention. In another embodiment, the additional anti-schizophrenia agent is administered to the mammal after administration of the compound of the invention. In another embodiment, the additional anti-schizophrenia agent is administered to the mammal (e.g., a human) simultaneously with the administration of the compound of the invention.

The invention also provides a pharmaceutical composition for the treatment of schizophrenia in a mammal, including a human, which comprises an amount of a compound of Formula I, as defined above (including hydrates, solvates and polymorphs of said compound or pharmaceutically acceptable salts thereof), in combination with one or more (preferably one to three) anti-schizophrenia agents such as ziprasidone, risperidone, olanzapine, quetiapine, aripiprazole, asenapine, blonanserin, or iloperidone, wherein the amounts of the active agent and the combination when taken as a whole are therapeutically effective for treating schizophrenia.

Compounds of Formula Id are CYP3A4 inhibitors. In one embodiment, the $IC_{50}$ of a compound of Formula Id with respect to CYP3A4 is less than about 10 µM, 5 µM, 2 µM, 1 µM, 500 nM, 200 nM, 100 nM, or 50 nM. Compounds of Formula Id are also CYP3A4 inhibitors that are selective over CYP3A5. As used herein, a selective CYP3A4 inhibitor (over CYP3A5) refers to a compound for which the ratio of its $IC_{50}$ with respect to CYP3A5 to its $IC_{50}$ with respect to CYP3A4 is greater than about 60, 70, 80, 90, 100, 120, 140, or 150. For instance, the $IC_{50}$ of Example 2 with respect to CYP3A4 (Testosterone) is about 122 nM and the $IC_{50}$ of Example 2 with respect to CYP3A5 (Testosterone) is about 20.93 µM. Thus, the ratio of its $IC_{50}$ with respect to CYP3A5 to its $IC_{50}$ with respect to CYP3A4 (fold selectivity) is about 172. Accordingly, a compound of Formula Id (such as Example 2 or 56) can be employed to develop methods that can be employed to distinguish the relative contributions of CYP3A4 and CYP3A5 in the metabolism of drugs.

The present invention further provides a method for inhibiting an activity of CYP3A4 (either in vitro or in vivo), comprising contacting (including incubating) the CYP3A4 with a compound of Formula Id (such as Example 2), or a pharmaceutically acceptable salt thereof.

The present invention further provides a method for selectively inhibiting an activity of CYP3A4 (either in vitro or in vivo), comprising contacting (including incubating) the CYP3A4 with a compound of Formula Id (such as Example 2), or a pharmaceutically acceptable salt thereof. The present invention provides a method for selectively inhibiting an activity of CYP3A4 (either in vitro or in vivo), comprising contacting (including incubating) the CYP3A4 with a compound of Formula Id (such as Example 2), or pharmaceutically acceptable salt thereof, in the presence of CYP3A5.

In another aspect, the present invention provides a method for determining the relative contributions of CYP3A4 versus CYP3A5 to the metabolism of a compound (either in vitro or in vivo) comprising using a compound of Formula Id (such as Example 2), or a pharmaceutically acceptable salt thereof. In one embodiment, a compound of Formula Id (such as Example 2), or a pharmaceutically acceptable salt thereof, is used as a reference standard/compound in such a method.

DETAILED DESCRIPTION OF THE INVENTION

Compounds of the invention, including salts thereof, can be prepared using known organic synthesis techniques and can be synthesized according to any of numerous possible synthetic routes.

The reactions for preparing compounds of the invention can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis*, 3$^{rd}$ Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC) or thin layer chromatography (TLC).

Compounds of Formula I and intermediates thereof may be prepared according to the following reaction schemes and accompanying discussion. Unless otherwise indicated, $R^1$ through $R^9$, $Q^1$, n, and structural Formula I are as defined above in the reaction schemes and discussion that follow. In general the compounds of this invention may be made by processes which include processes analogous to those known in the chemical arts, particularly in light of the description contained herein. Certain processes for the manufacture of the compounds of this invention and intermediates thereof are provided as further features of the invention and are illustrated by the following reaction schemes. Other processes may be described in the experimental section. The schemes and examples provided herein (including the corresponding description) are for illustration only, and not intended to limit the scope of the present invention.

Scheme 1 refers to preparation of compounds of Formula I. Referring to Scheme 1, a compound of Formula I can be prepared from a compound of Formula II [where $Lg^2$ is a suitable leaving group such as triazolyl or halo (e.g., Cl or Br)] by reaction with a hydrazine of formula $NH_2NHR^1$ in the presence of excess $NH_2NHR^1$ or a base (such as pyridine). Suitable temperatures for the aforesaid reaction are typically between 0° C. and 120° C. Suitable reaction times are typically from 20 minutes to 48 hours. Suitable reaction solvents typically can be selected from pyridine, acetonitrile, dioxane, and other organic solvents. A compound of Formula II can be prepared by reaction of a compound of Formula III [where each of $Lg^1$ and $Lg^2$ is independently a suitable leaving group such as triazolyl or halo (e.g., Cl or Br) or triflate] with about 1 molar equivalent of a primary or secondary amine compound of formula $HR^2$ [wherein $R^2$ is $N(R^3)_2$ or $HNR^3$], optionally in the presence of a base such as cesium carbonate or N,N-diisopropyl amine or triethylamine, in a suitable organic solvent such as acetonitrile or N,N-dimethylformamide. Suitable temperatures for the aforesaid reaction are typically between 0° C. and 100° C. Suitable reaction times are typically from 20 minutes to 48 hours. Compounds of Formula III are commercially available or can be made by methods described herein or other methods well known to those skilled in the art.

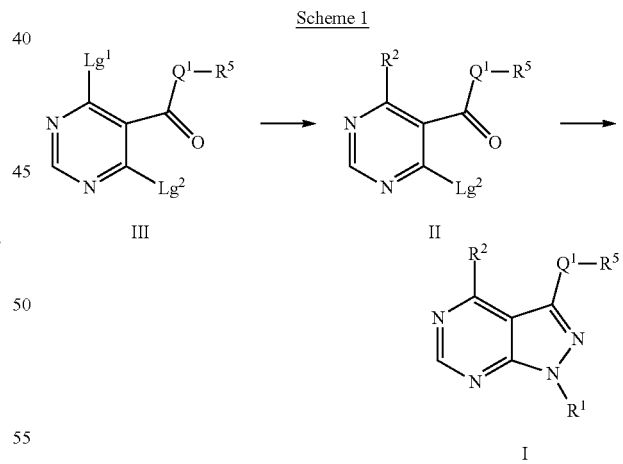

Scheme 2 refers to an alternative method for preparation of compounds of Formula I. Referring to Scheme 2, a compound of Formula I can be prepared by reaction of a compound of Formula IV [where $Lg^1$ is a suitable leaving group such as triazolyl or halo (e.g., Cl or Br)] with a primary or secondary amine compound of formula $HR^2$ [wherein $R^2$ is $N(R^3)_2$ or $HNR^3$], optionally in the presence of a base (such as cesium carbonate, diisopropylethylamine, or triethylamine), in a suitable organic solvent such as dichloromethane, acetonitrile, or N,N-dimethylformamide. Suitable temperatures for the aforesaid reaction are typically between 0° C. and 120° C. Suitable reaction times are typically from 20 minutes to 48 hours. A compound of Formula IV can be prepared by reacting a compound of Formula III [where each of $Lg^1$ and $Lg^2$ is independently a suitable leaving group such as triazolyl, halo (e.g., Cl or Br), or triflate] with about 1 molar equivalent of a hydrazine of formula $NH_2NHR^1$ in the presence of excess $NH_2NHR^1$ or a base (such as pyridine). Suitable temperatures for the aforesaid reaction are typically between 0° C. and 120° C. Suitable reaction times are typically from 20 minutes to 48 hours. Suitable reaction solvents typically can be selected from one or more of polar, aprotic organic solvents (such as acetonitrile or dioxane).

Scheme 2

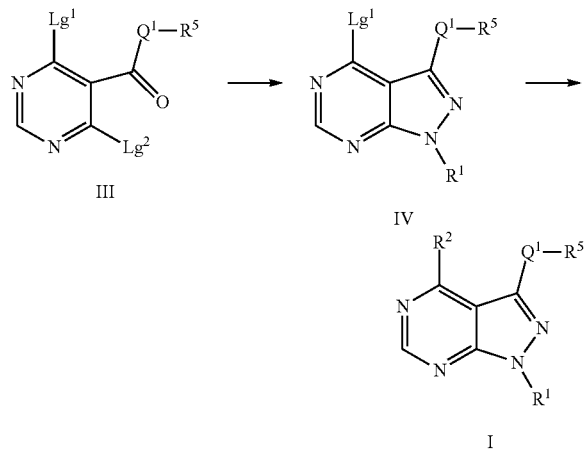

Scheme 3 refers to another alternative method for preparation of compounds of Formula I (including Formula Ia or Ib). Referring to Scheme 3, a compound of Formula I can be prepared by reacting a compound of Formula V [wherein $X^1$ is H, a halogen (Cl, Br, or I), triflate, or the like] with a compound of formula $R^5$—$Z^1$ [wherein $Z^1$ can be Br; B(OH)$_2$; or B(OR)$_2$ where each R is H or $C_{1-6}$ alkyl, or wherein two (OR) groups, together with the B atom to which they are attached, form a 5- to 10-membered heterocyclic ring optionally substituted with one or more $C_{1-6}$ alkyl; a trialkyltin moiety; or the like] by a palladium-catalyzed coupling reaction. The type of reaction employed depends on the selection of $X^1$ and $Z^1$. For example, when $X^1$ is halogen or triflate and the $R^5$—$Z^1$ reagent is a boronic acid or boronic ester, a Suzuki reaction may be used [A. Suzuki, *J. Organomet. Chem.* 1999, 576, 147-168; N. Miyaura and A. Suzuki, *Chem. Rev.* 1995, 95, 2457-2483; A. F. Littke et al., *J. Am. Chem. Soc.* 2000, 122, 4020-4028]. In some specific embodiments, a heteroaromatic iodide, bromide, or triflate of Formula V is combined with 1 to 3 equivalents of an aryl or heteroaryl boronic acid or boronic ester of formula $R^5$—$Z^1$ and a suitable base, such as 2 to 5 equivalents of sodium carbonate, in a suitable organic solvent such as ethanol. A palladium catalyst is added, such as 0.01 equivalents of tetrakis(triphenylphosphine)palladium (0), and the reaction mixture is heated to temperatures ranging from 60 to 100° C. for 1 to 24 hours. In some cases, it may be advantageous to employ 1 to 2 equivalents of copper(I) chloride and 1 to 2 equivalents of potassium bromide in the Suzuki reaction, in 1,2-dimethoxyethane as solvent. Alternatively, the coupling reaction may be carried out by reaction of a compound of Formula V (wherein $X^1$ is H) with 1 to 3 equivalents of a compound of formula $R^5$—$Z^1$ (wherein $Z^1$ is Br), in the presence of 0.01 to 0.5 equivalents of allylpalladium chloride dimer and a suitable base, such as 2 to 4 equivalents of potassium carbonate, in a suitable solvent such as 1,4-dioxane or toluene. The reaction typically may be carried out at temperatures ranging from 0 to 180° C. for 24 to 72 hours. When $X^1$ is halogen or triflate and $Z^1$ is trialkyltin, a Stille coupling may be employed [V. Farina et al., *Organic Reactions* 1997, 50, 1-652]. More specifically, a compound of Formula V (wherein $X^1$ is bromide, iodide, or triflate) may be combined with 1.5 to 3 equivalents of a compound of formula $R^5$—$Z^1$ (wherein the $R^5$—$Z^1$ compound is an $R^5$ stannane compound) in the presence of a palladium catalyst, such as 0.05 equivalents of dichlorobis(triphenylphosphine)palladium(II), in a suitable organic solvent such as toluene, and the reaction may be heated to temperatures ranging from 100 to 130° C. for 12 to 36 hours. Where $X^1$ is Br, I or, triflate and $Z^1$ is Br or I, a Negishi coupling may be used [E. Erdik, *Tetrahedron* 1992, 48, 9577-9648]. More specifically, a compound of Formula V (wherein $X^1$ is bromide, iodide, or triflate) may be transmetallated by treatment with 1 to 1.1 equivalents of an alkyllithium reagent followed by a solution of 1.2 to 1.4 equivalents of zinc chloride in an appropriate solvent such as tetrahydrofuran at a temperature ranging from –80 to –65° C. After warming to a temperature between 10 and 30° C., the reaction may be treated with a compound of formula $R^5$—$Z^1$ (wherein $Z^1$ is Br or I), and heated at 50 to 70° C. with addition of a catalyst such as tetrakis(triphenylphosphine)palladium (0). The reaction may be carried out for times ranging from 1 to 24 hours. None of these reactions are limited to the employment of the solvent, base, or catalyst described above, as many other conditions may be used.

As shown in Scheme 3, a compound of Formula Ia or Ib can be made by one or more methods described herein for making a compound of Formula I, starting from a compound of Formula Va or Vb, respectively.

Scheme 3

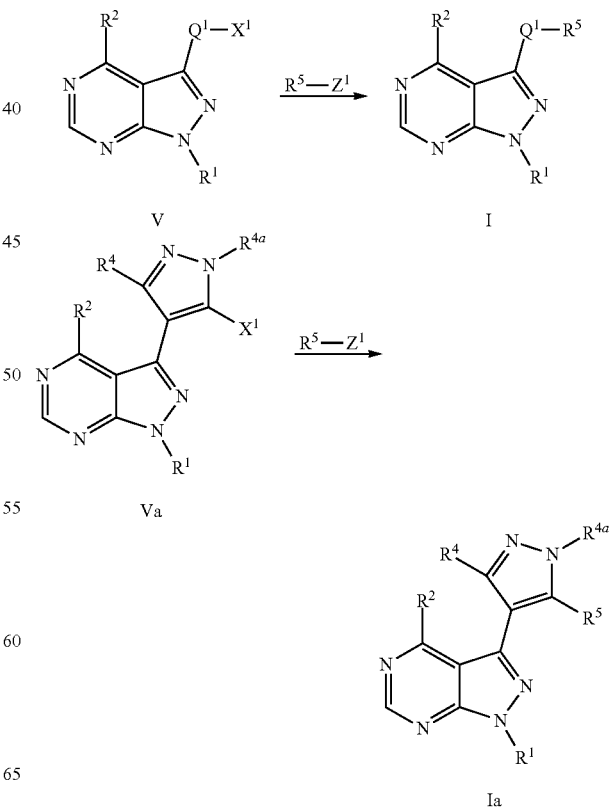

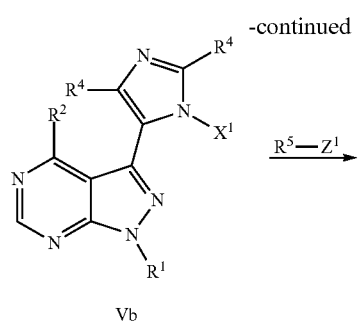

Vb

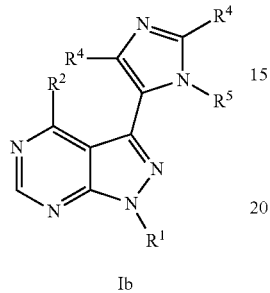

Ib

Scheme 4 refers to a preparation of compounds of Formula III, which can be used in Schemes 1 and/or 2. Referring to Scheme 4, a compound of Formula III can be made by oxidation of an alcohol of Formula VI, by employing a suitable oxidizing reagent (such as Dess-Martin reagent). Suitable temperatures for the aforesaid reaction are typically between 0° C. and 100° C. Suitable reaction times typically are from 20 minutes to 48 hours. Suitable reaction solvents typically can be selected from chloroform, dichloromethane, or acetonitrile. An alcohol compound of Formula VI can be prepared by reacting a pyrimidine of Formula VIII [where each of $Lg^1$ and $Lg^2$ is independently a suitable leaving group such as triazolyl, halo (e.g., Cl or Br), or triflate] with a heteroaryl-aldehyde of Formula VII, in the presence of a strong base such as an alkali metal dialkylamide (e.g., lithium diisopropylamide) and in a suitable organic solvent (such as tetrahydrofuran). Suitable temperatures for the aforesaid reaction typically are between –100° C. and 0° C. Suitable reaction times typically are from 20 minutes to 48 hours.

Scheme 4

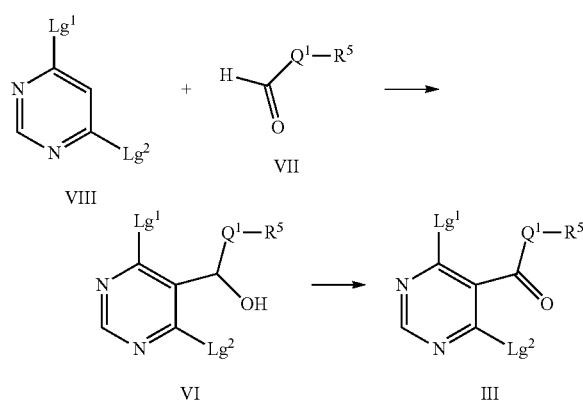

Scheme 5 refers to a preparation of compounds of Formula VII (including VIIa), which can be used in Scheme 4. Referring to Scheme 5, a heteroaryl-aldehyde of Formula VII can be prepared by subjecting a heteroaryl compound of Formula IX to Vilsmeier-Haack reaction conditions [e.g., in the presence of $POCl_3$ and N,N-dimethylformamide (DMF)]. See, e.g., A. Vilsmeier and A. Haack, *Ber.* 1927, 60, 119-122; and W. G. Jackson et al., *J. Am. Chem. Soc.* 1981, 103, 533-540. Suitable temperatures for the aforesaid reaction typically are between 0° C. and 160° C. Suitable reaction times typically are from 20 minutes to 48 hours. Similarly, the pyrazole-aldehyde of Formula VIIa can be made from a pyrazole of Formula IXa.

Scheme 5

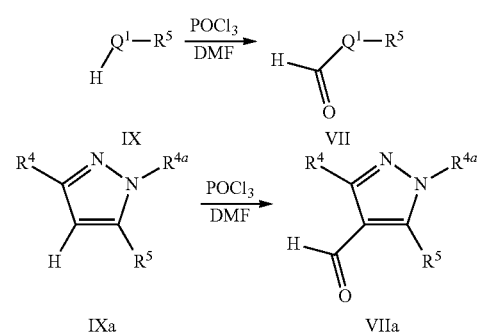

Scheme 6 refers to preparation of the compound of Formula VIIb, which can be used as a compound of Formula VII in Scheme 4. Referring to Scheme 6, a compound of Formula VIIb (an aldehyde) can be prepared by oxidizing an alcohol of Formula X in the presence of a suitable oxidizing reagent [such as Dess-Martin reagent, manganese dioxide, or PCC (pyridinium chlorochromate)] or by subjecting the alcohol of Formula X to Swern oxidation conditions [oxalyl chloride, dimethyl sulfoxide (DMSO) and an organic base such as triethylamine]. Suitable temperatures for the aforesaid reaction typically are between 0° C. and 100° C. Suitable reaction times typically are from 20 minutes to 48 hours. Suitable reaction solvents typically can be selected from dichloromethane, chloroform, or tetrahydrofuran (or another polar, aprotic organic solvent). An alcohol of Formula X can be prepared by reducing an imidazole-ester of Formula XI in the presence of a suitable reducing reagent such as diisobutylaluminum hydride (DIBAL) or lithium aluminum hydride. Suitable temperatures for the aforesaid reaction typically are between –100° C. and 40° C. Suitable reaction times are from 20 minutes to 48 hours. Suitable reaction solvents typically can be selected from a polar aprotic solvent such as tetrahydrofuran. An imidazole-ester of Formula XI can be prepared by reacting an ester of Formula XII-0 with an optionally substituted toluenesulphonylmethyl isocyanide of Formula XII-1 such as isocyanomethyl 4-methylphenyl sulfone. Suitable temperatures for the aforesaid reaction typically are between 0° C. and 120° C. Suitable reaction times typically are from 20 minutes to 48 hours. Suitable reaction solvents typically can be selected from alcoholic solvents such as ethanol or isopropyl alcohol. See e.g. A. M. van Leusen, J. Wildeman, O. H. Oldenziel, *J. Org. Chem.* 1977, 42, 1153; B.-C Chen et al., *Tetrahedron Lett.* 2000, 41, 5453-5456; J. Sisko et al., *J. Org. Chem.* 2000, 65, 1516-1524] An ester of Formula XII-0 can be prepared by reacting an aryl-amine or heteroaryl-amine of formula $R^5$—$NH_2$ (for example, an aniline optionally substituted with 1-3 substituents each independently selected from F, Cl, Br, and $C_{1-4}$ alkyl) with ethyl 2-oxoacetate in solvent such as methanol (alternatively, the ester of Formula XII-0 can be generated in situ and reacted with the compound of Formula II-1). Suitable temperatures for the aforesaid reaction typically are between 0° C. and 100° C. Suitable reaction times typically are from 20 minutes to 48 hours. Suitable reaction solvents typically can be selected from methanol, ethanol, and isopropyl alcohol.

Scheme 6

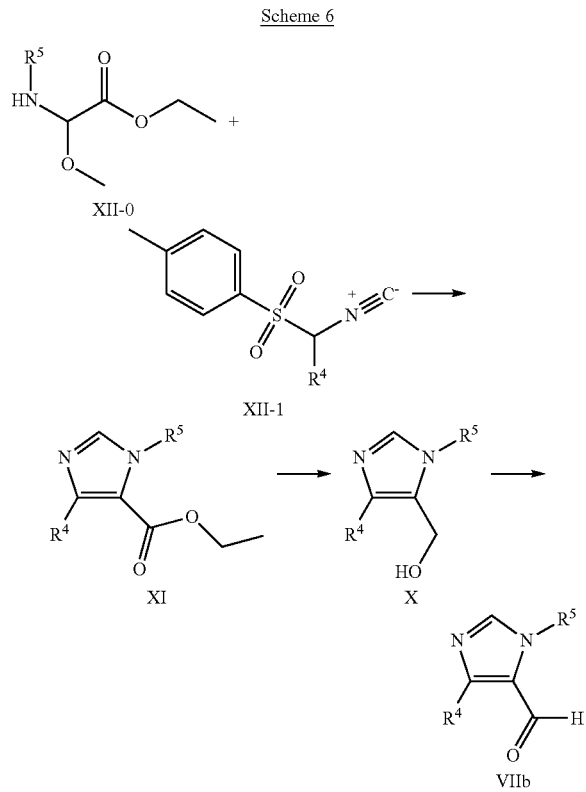

Scheme 7 refers to a preparation of compounds of Formula IXa, which can be used in Scheme 5. Referring to Scheme 7, a compound of Formula IXa can be prepared by reacting a compound of Formula XIII [wherein $Z^2$ can be Br; $B(OH)_2$; or $B(OR)_2$ where each R is H or $C_{1-6}$ alkyl, or two (OR) groups, together with the B atom to which they are attached, form a 4- to 10-membered heterocyclic ring optionally substituted with one or more $C_{1-6}$ alkyl; a trialkyltin moiety; or the like] with a compound of formula $R^5$—$X^2$ [wherein $X^2$ is H; a halogen (Cl, Br, or I), triflate, or the like] by a palladium-catalyzed coupling reaction. The type of reaction employed depends on the selection of $X^2$ and $Z^2$. The mechanism and types of the coupling reaction that can be used in Scheme 7 are similar to those described in Scheme 3. For example, when $X^2$ is halogen (e.g., Br or I) and the compound of Formula XIII is a boronic acid or boronic ester [i.e., wherein $Z^2$ is $B(OH)_2$ or $B(OR)_2$ where each R is H or $C_{1-6}$ alkyl, or two (OR) groups, together with the B atom to which they are attached, form a 4- to 10-membered heterocyclic ring optionally substituted with one or more $C_{1-6}$ alkyl], a Suzuki reaction may be used.

Scheme 7

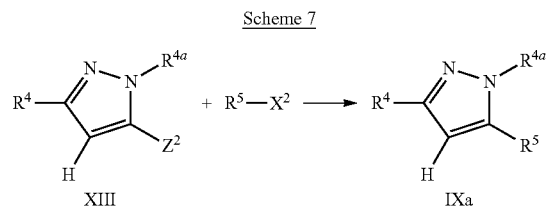

Scheme 8 refers to a preparation of a compound of Formula XIIIa (an example of a compound of Formula XIII in Scheme 7). Referring to Scheme 8, a pyrazole-boronic acid of Formula XIIIa can be prepared by reacting a pyrazole of Formula XIVa with a trialkyl borate (e.g., triisopropyl borate) in the presence of a strong base such as RLi (wherein R can be an alkyl, for example, n-butyl). Suitable temperatures for the aforesaid reaction typically are between −100° C. and 40° C. Suitable reaction times typically are from 20 minutes to 48 hours. Suitable reaction solvents typically can be selected from polar aprotic solvents such as tetrahydrofuran.

Scheme 8

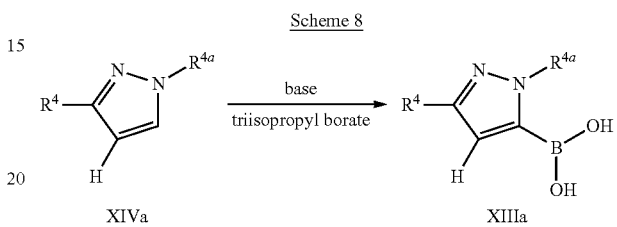

Scheme 9 refers to a preparation of a pyrazole of Formula XVII (an example of a compound of Formula IXa in Scheme 5). Referring to Scheme 9, a pyrazole of Formula XVII can be prepared by reacting a compound of Formula XVI with a hydrazine of formula $R^{4a}NH$—$NH_2$ (e.g., methylhydrazine). Suitable temperatures for the aforesaid reaction typically are between 0° C. and 160° C. Suitable reaction times typically are from 20 minutes to 48 hours. Suitable reaction solvents typically can be selected from polar aprotic solvents such as N,N-dimethylformamide or 1,4-dioxane. A compound of Formula XVI can be prepared by reacting an aryl-methyl ketone or a heteroaryl-methyl ketone of Formula XV (for example, wherein $R^5$ is a 4-methylphenyl or 4-ethylphenyl) with N,N-dimethylformamide dimethylacetal (DMF-DMA). Suitable temperatures for the aforesaid reaction typically are between 0° C. and 160° C. Suitable reaction times typically are from 20 minutes to 48 hours. Suitable reaction solvents can be selected from N,N-dimethylformamide (which is also a reagent).

Scheme 9

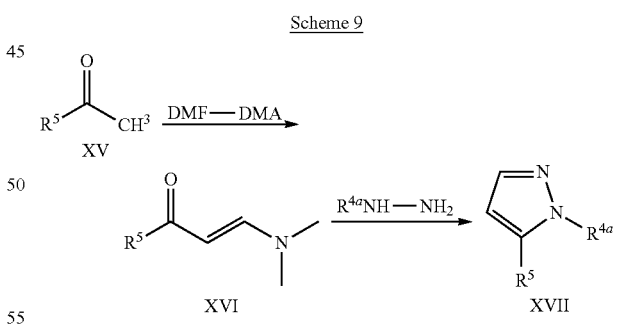

Scheme 10 refers to an alternative method for preparation of compounds of Formula Ia. Referring to Scheme 10, a compound of Formula Ia can be prepared by reaction of a compound of Formula XXIII with an aryl or heteroaryl compound of formula $R^5$—$X^2$ [wherein $X^2$ can be a leaving group such as halo (e.g., Br or I) or triflate] in the presence of a palladium catalyst [e.g. palladium(II) acetate] and a suitable base (e.g., an alkali carbonate such as potassium carbonate or tetra-n-butylammonium acetate). The palladium-catalyzed reactions that can be employed depend on the selection of $X^2$; the mechanism and types of the coupling reactions that can be employed are similar to those described in Scheme 3. Suitable temperatures for the aforesaid reaction typically are between 0° C. and 180° C. Suitable reaction times typically are from 20 minutes to 120 hours. Suitable reaction solvents typically can be selected from organic solvents such as 1,4-dioxane or toluene. A compound of Formula XXIII can be prepared by reacting an iodide compound of Formula XXI with a boronic acid or a boronic ester compound of Formula XXII [where each R is H or $C_{1-6}$ alkyl, or wherein two (OR) groups, together with the B atom to which they are attached, form a 4- to 10-membered heterocyclic ring optionally substituted with one or more $C_{1-6}$ alkyl] in the presence of a palladium catalyst [e.g., tris(dibenzylideneacetone)dipalladium(0)] and a suitable base (e.g. potassium phosphate). Suitable temperatures for the aforesaid reaction typically are between 0° C. and 200° C. Suitable reaction times typically are from 20 minutes to 48 hours. Suitable reaction solvents typically can be selected from 1,4-dioxane/aqueous potassium phosphate mixture.

Still referring to Scheme 10, a compound of Formula XXI can be prepared by reacting a chloride compound of Formula XX with a primary or secondary amine compound of formula $HR^2$ [wherein $R^2$ is $N(R^3)_2$ or $HNR^3$], optionally in the presence of a base such as aqueous sodium bicarbonate or triethylamine, in a suitable organic solvent such as a polar organic solvent [e.g. tetrahydrofuran (THF)]. Suitable temperatures for the aforesaid reaction typically are between 0° C. and 100° C. Suitable reaction times typically are from 20 minutes to 48 hours. A compound of Formula XX can be prepared by reacting a hydroxyl compound of Formula XIX with a chlorination reagent (such as phosphorus oxychloride) in a suitable organic solvent such as a polar, aprotic organic solvent (e.g. acetonitrile or 1,2-dichloroethane). Suitable temperatures for the aforesaid reaction typically are between 0° C. and 150° C. Suitable reaction times typically are from 20 minutes to 48 hours. A compound of Formula XIX can be prepared by reacting a pyrazolopyrimidine of Formula XVIII with an iodination reagent (such as N-iodosuccinimide) in a suitable organic solvent such as a polar, aprotic organic solvent (e.g. acetonitrile or 1,2-dichloroethane) with the optional use of an acid such as tetrafluoroboric acid. Suitable temperatures for the aforesaid reaction typically are between 0° C. and 130° C. Suitable reaction times typically are from 20 minutes to 48 hours.

Scheme 10

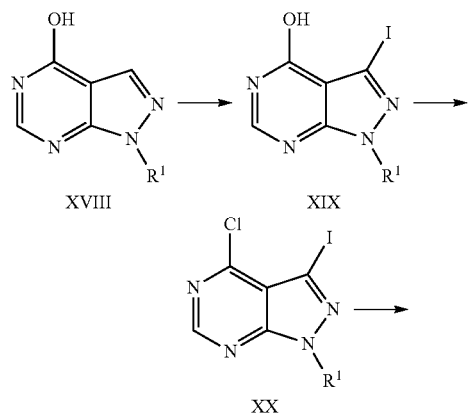

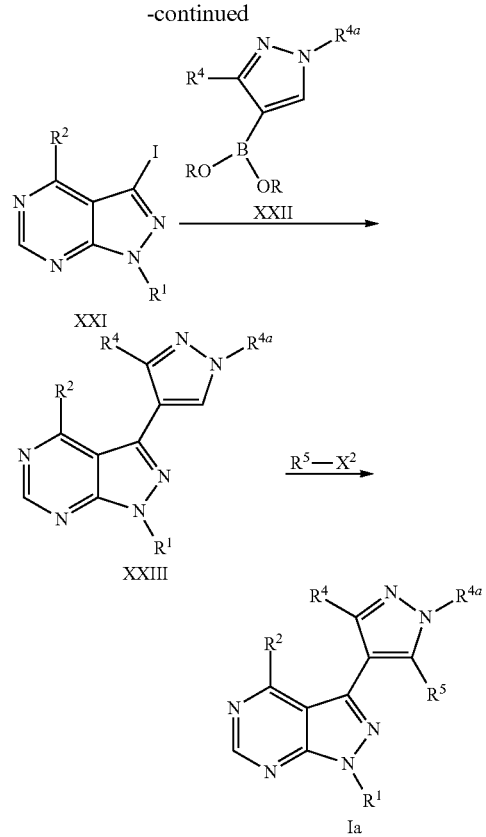

Scheme 11 refers to an alternative method for preparation of compounds of Formula Ia. Referring to Scheme 11, a compound of Formula Ia can be prepared by reacting a ketone of Formula XXIX [where $Lg^2$ is a suitable leaving group such as triazolyl, halo (e.g., Cl or Br), or triflate] with about 1 molar equivalent of a hydrazine of formula $NH_2NHR^1$ in the presence of excess $NH_2NHR^1$ or a base (such as pyridine). Suitable temperatures for the aforesaid reaction typically are between 0° C. and 100° C. Suitable reaction times typically are from 20 minutes to 48 hours. Suitable reaction solvents typically can be selected from a polar, aprotic solvent such as 1,4-dioxane. A ketone of Formula XXIX can be made by oxidation of an alcohol of Formula XXVIII by employing a suitable oxidizing reagent (such as Dess-Martin reagent). Suitable temperatures for the aforesaid reaction typically are between −20° C. and 100° C. Suitable reaction times typically are from 20 minutes to 48 hours. Suitable reaction solvents typically can be selected from a polar solvent such as dichloromethane. An alcohol of Formula XXVIII can be prepared by reacting an aldehyde of Formula XXV and a halogenated compound such as an iodinated compound of Formula XXVII in the presence of a reagent (such as an organolithium compound, for example n-butyllithium; or an organomagesium compound, for example iso-propyl magnesium bromide or iso-propyl magnesium chloride) suitable for metal-halogen exchange. Suitable temperatures for the aforesaid reaction typically are between −100° C. and 50° C. Suitable reaction times typically are from 20 minutes to 48 hours. Suitable reaction solvents typically can be selected from polar, aprotic solvents such as tetrahydrofuran.

Still referring to Scheme 11, a compound of Formula XXV can be prepared by reaction of a compound of Formula XXIV [where $Lg^1$ is a suitable leaving group such as triazolyl or halo (e.g., Cl or Br)] with a primary or secondary amine compound of formula HR² [wherein R² is N(R³)₂ or HNR³], optionally in the presence of a base such as cesium carbonate, diisopropylethylamine, or triethylamine, in a suitable organic solvent such as dichloromethane, chloroform or N,N-dimethylformamide. Suitable temperatures for the aforesaid reaction typically are between 0° C. and 100° C. Suitable reaction times typically are from 20 minutes to 48 hours. A halogenated pyrazole such as an iodinated pyrazole of Formula XXVII can be prepared by reacting a pyrazole of Formula XXVI with an iodination reagent (such as N-iodosuccinimide) in a suitable organic solvent such as a polar organic solvent (e.g. acetic acid). Suitable temperatures for the aforesaid reaction typically are between 0° C. and 120° C. Suitable reaction times typically are from 20 minutes to 48 hours.

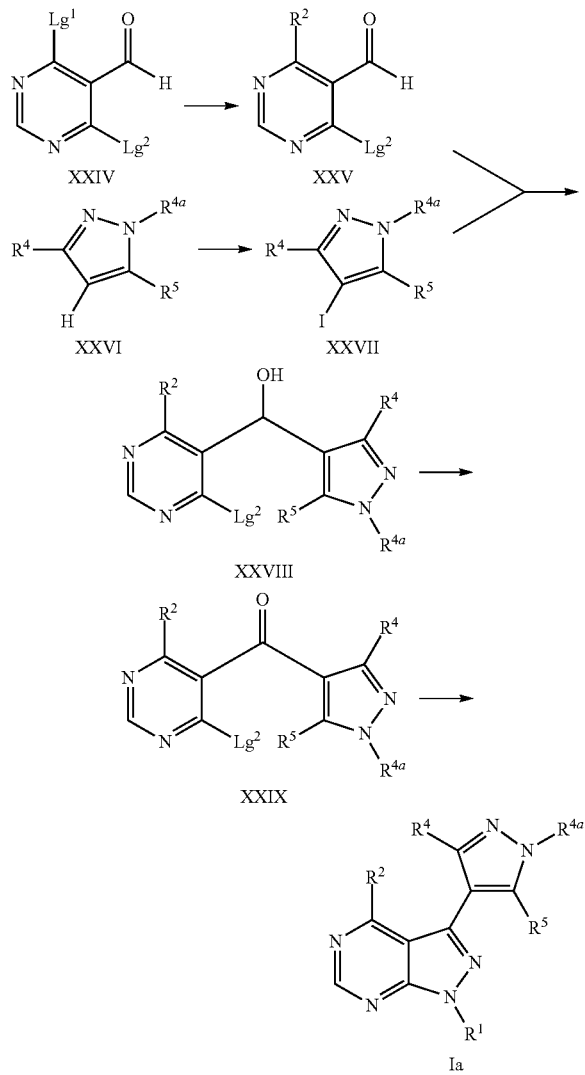

Additional starting materials and intermediates useful for making the compounds of the present invention can be obtained from chemical vendors such as Sigma-Aldrich or can be made according to methods described in the chemical art.

Those skilled in the art can recognize that in all of the Schemes described herein, if there are functional (reactive) groups present on a substituent group such as $R^3$, $R^5$, etc., further modification can be made if appropriate and/or desired, using methods well known to those skilled in the art. For example, a CN group can be hydrolyzed to afford an amide group; a carboxylic acid can be converted to an amide; a carboxylic acid can be converted to an ester, which in turn can be reduced to an alcohol, which in turn can be further modified. For another example, an OH group can be converted into a better leaving group such as a mesylate, which in turn is suitable for nucleophilic substitution, such as by a cyanide ion (CN⁻). For another example, an —S— can be oxidized to —S(=O)— and/or —S(=O)₂—. For yet another example, an unsaturated bond such as C=C or C≡C can be reduced to a saturated bond by hydrogenation. In some embodiments, a primary amine or a secondary amine moiety (present on a substituent group such as $R^3$, $R^5$, etc.) can be converted to an amide, sulfonamide, urea, or thiourea moiety by reacting it with an appropriate reagent such as an acid chloride, a sulfonyl chloride, an isocyanate, or a thioisocyanate compound. One skilled in the art will recognize further such modifications. Thus, a compound of Formula I having a substituent which contains a functional group can be converted to another compound of Formula I having a different substituent group.

Similarly, those skilled in the art can also recognize that in all of the schemes described herein, if there are functional (reactive) groups present on a substituent group such as $R^3$, $R^5$, etc., these functional groups can be protected/deprotected in the course of the synthetic scheme described here, if appropriate and/or desired. For example, an OH group can be protected by a benzyloxycarbonyl group, which can be deprotected and converted back to the OH group in a later stage of the synthetic process. For another example, an NH₂ group can be protected by a Boc group, which can be deprotected and converted back to the NH₂ group in a later stage of the synthetic process.

As used herein, the term "reacting" (or "reaction" or "reacted") refers to the bringing together of designated chemical reactants such that a chemical transformation takes place generating a compound different from any initially introduced into the system. Reactions can take place in the presence or absence of solvent.

Compounds of Formula I that have chiral centers may exist as stereoisomers, such as racemates, enantiomers, or diastereomers. Conventional techniques for the preparation/isolation of individual enantiomers include chiral synthesis from a suitable optically pure precursor or resolution of the racemate using, for example, chiral high pressure liquid chromatography (HPLC). Alternatively, the racemate (or a racemic precursor) may be reacted with a suitable optically active compound, for example, an alcohol, or, in the case where the compound contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to one skilled in the art. Chiral compounds of Formula I (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture. Stereoisomeric conglomerates may be separated by conventional techniques known to those skilled in the art. See, e.g. "Stereochemistry of Organic Compounds" by E. L. Eliel (Wiley, New York, 1994), the disclosure of which is incorporated herein by reference in its entirety. Suitable stereoselective techniques are well-known to those of ordinary skill in the art.

Where a compound of Formula I contains an alkenyl or alkenylene (alkylidene) group, geometric cis/trans (or Z/E) isomers are possible. Cis/trans isomers may be separated by conventional techniques well known to those skilled in the art, for example, chromatography and fractional crystallization. Salts of the present invention can be prepared according to methods known to those of skill in the art.

The compounds of Formula I that are basic in nature are capable of forming a wide variety of salts with various inorganic and organic acids. Although such salts must be pharmaceutically acceptable for administration to animals, it is often desirable in practice to initially isolate the compound of the present invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention can be prepared by treating the base compound with a substantially equivalent amount of the selected mineral or organic acid in an aqueous solvent medium or in a suitable organic solvent, such as methanol or ethanol. Upon evaporation of the solvent, the desired solid salt is obtained. The desired acid salt can also be precipitated from a solution of the free base in an organic solvent by adding an appropriate mineral or organic acid to the solution.

If the inventive compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, isonicotinic acid, acetic acid, lactic acid, pantothenic acid, bitartric acid, ascorbic acid, 2,5-dihydroxybenzoic acid, fumaric acid, gluconic acid, saccharic acid, formic acid, methanesulfonic acid, ethanesulfonic acid, benzenesulfonic acid, p-toluenesulfonic acid and pamoic [i.e., 1,1'-methylene-bis-(2-hydroxy-3-naphthoate)] acids, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

Those compounds of Formula I that are acidic in nature are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the acidic compounds of Formula I. These salts may be prepared by any suitable method, for example, treatment of the free acid with an inorganic or organic base, such as an amine (primary, secondary or tertiary), an alkali metal hydroxide or alkaline earth metal hydroxide, or the like. These salts can also be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

The invention also includes isotopically labeled compounds of Formula I, wherein one or more atoms is replaced by an atom having the same atomic number, but an atomic mass or mass number different from the atomic mass or mass number usually found in nature. Isotopically labeled compounds of Formula I can generally be prepared by conventional techniques known to those skilled in the art or by processes analogous to those described herein, using an appropriate isotopically labeled reagent in place of the non-labeled reagent otherwise employed.

The invention will be described in greater detail by way of specific examples. The following examples are offered for illustrative purposes, and are not intended to limit the invention in any manner. Those of skill in the art will readily recognize a variety of non-critical parameters that can be changed or modified to yield essentially the same results. In the following Examples and Preparations, "DMSO" means dimethyl sulfoxide, "N" where referring to concentration means Normal, "M" means molar, "mL" means milliliter, "mmol" means millimoles, "µmol" means micromoles, "eq." means equivalent, "° C." means degrees Celsius, "MHz" means megahertz, "HPLC" means high-performance liquid chromatography.

EXAMPLES

Experiments were generally carried out under inert atmosphere (nitrogen or argon), particularly in cases where oxygen- or moisture-sensitive reagents or intermediates were employed. Commercial solvents and reagents were generally used without further purification, including anhydrous solvents where appropriate (for examples, generally Sure-Seal™ products from the Aldrich Chemical Company, Milwaukee, Wis., USA; for another examples, commercial solvents and reagents can be obtained from Sigma Aldrich, St. Louis, Mo., USA, or from Fisher Scientific, Pittsburgh, Pa., USA). Products were generally dried under vacuum before being carried on to further reactions or submitted for biological testing. Mass spectrometry data is reported from either liquid chromatography-mass spectrometry (LCMS), atmospheric pressure chemical ionization (APCI) or gas chromatography-mass spectrometry (GCMS) instrumentation. Chemical shifts for nuclear magnetic resonance (NMR) data are expressed in parts per million (ppm, δ) referenced to residual peaks from the deuterated solvents employed.

For syntheses referencing procedures in other Examples or Methods, reaction conditions (length of reaction and temperature) may vary. In general, reactions were followed by thin layer chromatography or mass spectrometry, and subjected to work-up when appropriate. Purifications may vary between experiments: in general, solvents and the solvent ratios used for eluents/gradients were chosen to provide appropriate $R_f$s or retention times.

Example 1

4-(Azetidin-1-yl)-1-methyl-3-[1-methyl-5-(4-methylphenyl)-1H-pyrazol-4-yl]-1H-pyrazolo[3,4-d]pyrimidine

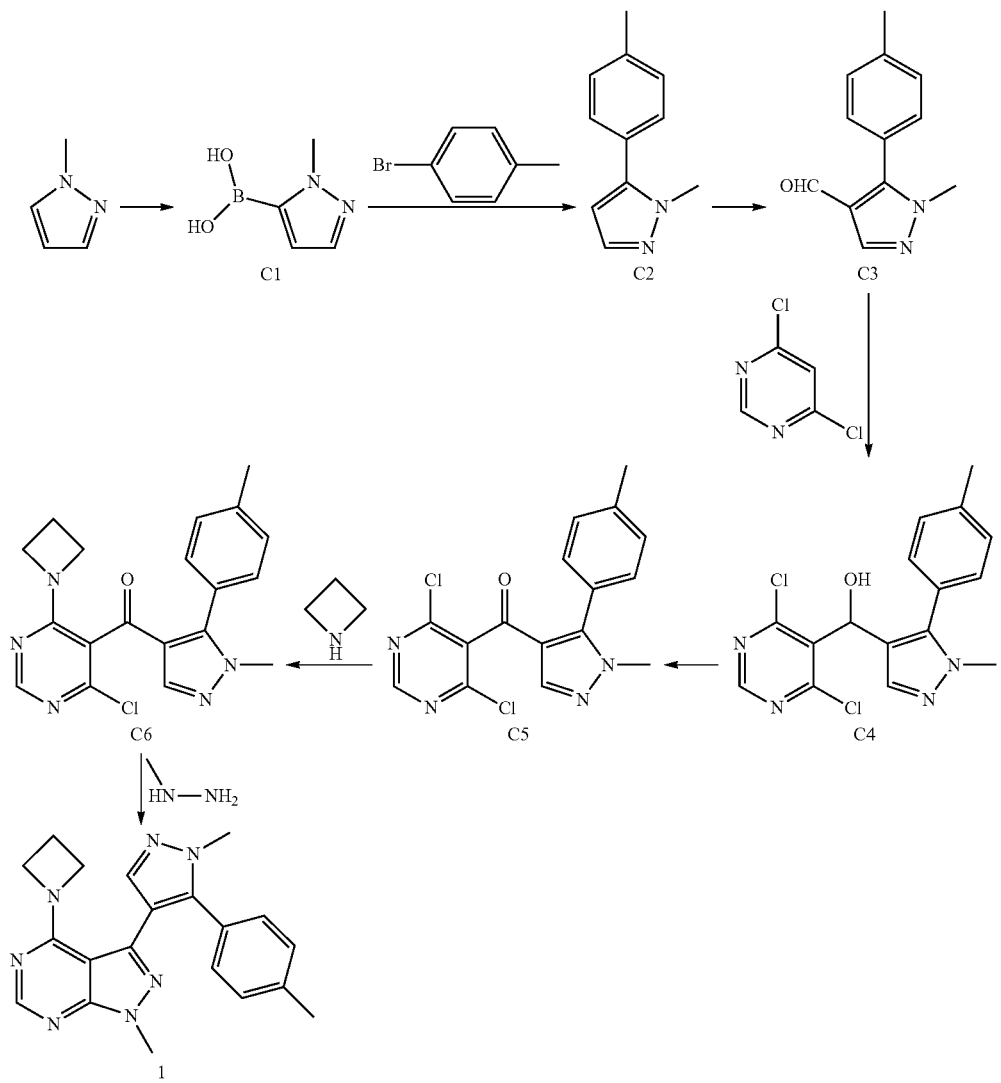

Step 1: Synthesis of (1-methyl-1H-pyrazol-5-yl)boronic acid (C1)

To a solution of 1-methyl-1H-pyrazole (110 g, 1.34 mol) in anhydrous tetrahydrofuran (2 L), with stirring, was added drop-wise n-butyllithium (2.5 M, 590 mL, 1.47 mol) at −78° C. After completion of the addition, the mixture was stirred for 1.5 hours at −78° C. Then triisopropyl borate (277 g, 1.47 mol) was added and the mixture was gradually warmed to room temperature and stirred overnight. Saturated aqueous ammonium chloride solution (1 L) was added drop-wise, while keeping the temperature of the reaction mixture below 10° C. The resulting mixture was acidified to a pH of approximately 6 with 1 N aqueous hydrochloric acid. The organic phase was separated and the aqueous phase was extracted with ethyl acetate (3×1 L). The combined organic layers were washed with saturated aqueous sodium chloride solution, dried over sodium sulfate, and filtered; and the solvent was removed under reduced pressure. The residue was washed with petroleum ether (3×300 mL) and the resulting solid was dried under vacuum to afford the product as a white solid. Yield: 157 g, 1.25 mol, 93%. $^1$H NMR (400 MHz, DMSO-$d_6$) δ 3.97 (s, 3H), 6.72-6.74 (m, 1H), 7.34-7.36 (m, 1H), 8.35 (br s, 2H).

Step 2: Synthesis of 5-(4-methylphenyl)-1-methyl-1H-pyrazole (C2)

A mixture of (1-methyl-1H-pyrazol-5-yl)boronic acid (C1) (60.0 g, 0.476 mol) and 1-bromo-4-methylbenzene (75.0 g, 0.438 mol) in a mixture of 1,2-dimethoxyethane (1.2 L) and 2 M aqueous sodium carbonate solution (550 mL) was degassed and purged with $N_2$; this procedure was then repeated twice. Dichlorobis(triphenylphosphine)palladium (II) (3.1 g, 4.4 mmol) was added and the mixture was purged twice with $N_2$. The reaction mixture was heated to reflux and stirred under N$_2$ for 3 hours. The mixture was cooled and 1,2-dimethoxyethane was removed under reduced pressure; water (500 mL) was added to the residue, and the resulting mixture was extracted with dichloromethane (3×500 mL). The combined organic layers were washed with saturated aqueous sodium chloride solution, dried over sodium sulfate, filtered, and concentrated in vacuo. Purification via silica gel chromatography (Eluent: 100:1 petroleum ether/ethyl acetate) provided the product as a yellow liquid. Yield: 55.0 g, 319 mmol, 73%. $^1$H NMR (400 MHz, CDCl$_3$) δ 2.42 (s, 3H), 3.89 (s, 3H), 6.29 (d, J=1.8 Hz, 1H), 7.29 (br AB quartet, J$_{AB}$=8 Hz, Δν$_{AB}$=18 Hz, 4H), 7.52 (d, J=2.0 Hz, 1H).

Step 3: Synthesis of 5-(4-methylphenyl)-1-methyl-1H-pyrazole-4-carbaldehyde)(C3)

N,N-Dimethylformamide (300 mL) was cooled to 0° C. and treated with phosphorus oxychloride (80 g, 0.52 mol). After completion of the addition, the resulting mixture was warmed to room temperature and stirred for 1 hour. 5-(4-Methylphenyl)-1-methyl-1H-pyrazole (C2) (30.0 g, 174 mmol) was added and the reaction mixture was heated to 120° C. and stirred overnight. The mixture was cooled to room temperature and concentrated in vacuo. The residue was poured into ice-water (700 mL), then adjusted to a pH of approximately 8 with saturated aqueous sodium carbonate solution. The resulting mixture was extracted with dichloromethane (4×300 mL); the combined organic layers were washed with saturated aqueous sodium chloride solution, dried over sodium sulfate, filtered, and concentrated under reduced pressure. Purification by silica gel chromatography (Gradient: 1:100 to 1:30 ethyl acetate in petroleum ether) afforded the product as a yellow solid. Yield: 28.2 g, 141 mmol, 81%. $^1$H NMR (400 MHz, CDCl$_3$) δ 2.46 (s, 3H), 3.81 (s, 3H), 7.33 (br AB quartet, J$_{AB}$=8 Hz, Δν$_{AB}$=17 Hz, 4H), 8.04 (s, 1H), 9.60 (s, 1H).

Step 4: Synthesis of (4,6-dichloropyrimidin-5-yl)[1-methyl-5-(4-methylphenyl)-1H-pyrazol-4-yl]methanol (C4)

n-Butyllithium (2.5 M in hexanes, 240 mL, 0.60 mol) was added drop-wise to a solution of diisopropylamine (85.2 mL, 0.60 mol) in tetrahydrofuran (600 mL) at −78° C. After the reaction had stirred for 30 minutes at −78° C., a solution of 4,6-dichloropyrimidine (89.4 g, 0.600 mol) in tetrahydrofuran (600 mL) was added drop-wise at about −90° C., and stirring was continued for 1 hour. To this mixture was added drop-wise a solution of 5-(4-methylphenyl)-1-methyl-1H-pyrazole-4-carbaldehyde (C3) (60.0 g, 300 mmol) in tetrahydrofuran (600 mL) at about −90° C. After completion of the addition, the reaction mixture was stirred at this temperature for 2 hours. The reaction mixture was quenched with acetic acid (60 g); the mixture was warmed to room temperature, and then concentrated under reduced pressure to remove tetrahydrofuran. The residue was dissolved in ethyl acetate (2 L) and washed with saturated aqueous sodium bicarbonate solution (1 L). The organic layer was washed with saturated aqueous sodium chloride solution, dried over sodium sulfate, and concentrated in vacuo. Recrystallization from ethyl acetate yielded the product as a white solid. Yield: 82.0 g, 235 mmol, 78%. $^1$H NMR (400 MHz, CDCl$_3$) δ 2.39 (s, 3H), 3.72 (s, 3H), 6.26 (s, 1H), 7.17 (br AB quartet, J$_{AB}$=8 Hz, Δν$_{AB}$=32 Hz, 4H), 7.66 (s, 1H), 8.55 (s, 1H).

Step 5: Synthesis of (4,6-dichloropyrimidin-5-yl)[1-methyl-5-(4-methylphenyl)-1H-pyrazol-4-yl]methanone (C5)

To a mixture of (4,6-dichloropyrimidin-5-yl)[1-methyl-5-(4-methylphenyl)-1H-pyrazol-4-yl]methanol (C4) (60 g, 170 mmol) and chloroform (1.8 L) was added Dess-Martin periodinane (110 g, 258 mmol) in portions at room temperature. After the addition was complete, the reaction mixture was stirred at room temperature for 2 hours, and then concentrated in vacuo. The residue was taken up in ethyl acetate and washed with aqueous sodium hydroxide solution (0.5 N, 2×800 mL), then with saturated aqueous sodium chloride solution, dried over sodium sulfate, and concentrated under reduced pressure. Recrystallization from methanol afforded the product as a light yellow solid. Yield: 31.3 g, 90.1 mmol, 53%. LCMS m/z 346.9 (M+1). $^1$H NMR (400 MHz, CDCl$_3$) δ 2.33 (s, 3H), 3.69 (s, 3H), 7.07-7.15 (br AB quartet, J$_{AB}$=8 Hz, Δν$_{AB}$=8 Hz, 4H), 8.15 (s, 1H), 8.49 (s, 1H).

Step 6: Synthesis of [4-(azetidin-1-yl)-6-chloropyrimidin-5-yl][1-methyl-5-(4-methylphenyl)-1H-pyrazol-4-yl]methanone (C6)

To a solution of (4,6-dichloropyrimidin-5-yl)[1-methyl-5-(4-methylphenyl)-1H-pyrazol-4-yl]methanone (C5) (200 mg, 0.576 mmol) in acetonitrile (6.0 mL) were added azetidine (39.0 µL, 0.576 mmol) and N,N-diisopropylethylamine (151 µL, 0.867 mmol). The reaction mixture was stirred at room temperature overnight and then concentrated in vacuo. The product was carried to Step 7 without further purification. LCMS m/z 368.4 (M+1).

Step 7: Synthesis of 4-(azetidin-1-yl)-1-methyl-3-[1-methyl-5-(4-methylphenyl)-1H-pyrazol-4-yl]-1H-pyrazolo[3,4-d]pyrimidine (1)

To a solution of [4-(azetidin-1-yl)-6-chloropyrimidin-5-yl][1-methyl-5-(4-methylphenyl)-1H-pyrazol-4-yl]methanone (C6) (from Step 6, ≤0.576 mmol) in pyridine (5.0 mL) was added methylhydrazine (0.302 mL, 5.74 mmol), and the reaction was stirred at 85° C. for 4 hours. The reaction mixture was concentrated under reduced pressure, and the residue was purified via silica gel chromatography (Gradient: 0 to 30% methanol in dichloromethane) to provide the title product as a colorless oil. Yield: 200 mg, 0.556 mmol, 97% over two steps. LCMS m/z 360.5 (M+1). $^1$H NMR (400 MHz, CDCl$_3$) δ 2.21-2.30 (m, 2H), 2.34 (br s, 3H), 3.75-4.04 (br m, 4H), 3.91 (s, 3H), 3.99 (s, 3H), 7.20 (br AB quartet, J$_{AB}$=8.1 Hz, Δν$_{AB}$=33 Hz, 4H), 7.67 (s, 1H), 8.32 (s, 1H).

Example 2

1-Methyl-3-[1-methyl-5-(4-methylphenyl)-1H-pyrazol-4-yl]-4-[(3S)-3-(piperidin-1-yl)pyrrolidin-1-yl]-1H-pyrazolo[3,4-d]pyrimidine

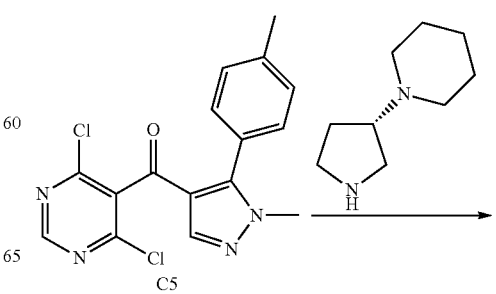

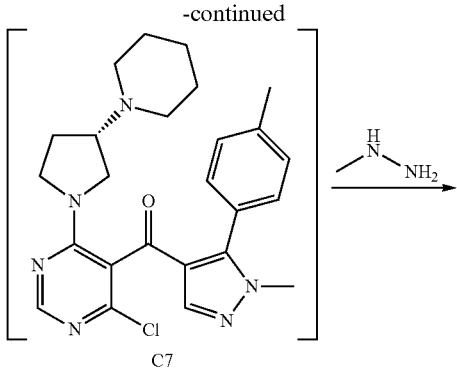

To a mixture of (4,6-dichloropyrimidin-5-yl)[1-methyl-5-(4-methylphenyl)-1H-pyrazol-4-yl]methanone (C5) (7.3 g, 21 mmol) and N,N-diisopropylethylamine (13.56 g, 104.9 mmol) in acetonitrile (100 mL) was added 1-[(3S)-pyrrolidin-3-yl]piperidine (4.8 g, 31 mmol), and the resulting reaction mixture was stirred at room temperature for 3 hours. To this solution of {4-chloro-6-[(3S)-3-(piperidin-1-yl)pyrrolidin-1-yl]pyrimidin-5-yl}[1-methyl-5-(4-methylphenyl)-1H-pyrazol-4-yl]methanone (C7) was added drop-wise a solution of methylhydrazine (12.1 g, 262 mol) in acetonitrile (20 mL). After being stirred overnight at room temperature, the reaction mixture was concentrated in vacuo and partitioned between dichloromethane (100 mL) and water (100 mL). The aqueous layer was extracted with dichloromethane (2×100 mL). The combined organic layers were dried over sodium sulfate, filtered and concentrated; purification via silica gel chromatography (Gradient: 10% to 50% ethyl acetate in petroleum ether) afforded the product as a white solid. Yield: 8.64 g, 18.9 mmol, 90% yield. LCMS m/z 457.3 (M+1). $^1$H NMR (400 MHz, CDCl$_3$) δ 1.39-1.49 (br m, 2H), 1.53-1.73 and 2.00-2.25 (br multiplets, presumed 8H), 2.31 (s, 3H), 2.32-2.45 (br m, 2H), 2.56-2.68 (br m, 1H), 2.90-3.16 (v br m, 1H), 3.26-3.78 (br m, 3H), 3.87 (s, 3H), 4.00 (s, 3H), 7.16 (br AB quartet, J$_{AB}$=8 Hz, Δν$_{AB}$=26 Hz, 4H), 7.66 (s, 1H), 8.29 (s, 1H).

Example 3

3-[5-(4-Cyclopropylphenyl)-1-methyl-1H-pyrazol-4-yl]-4-(3-fluoroazetidin-1-yl)-1-methyl-1H-pyrazolo[3,4-d]pyrimidine

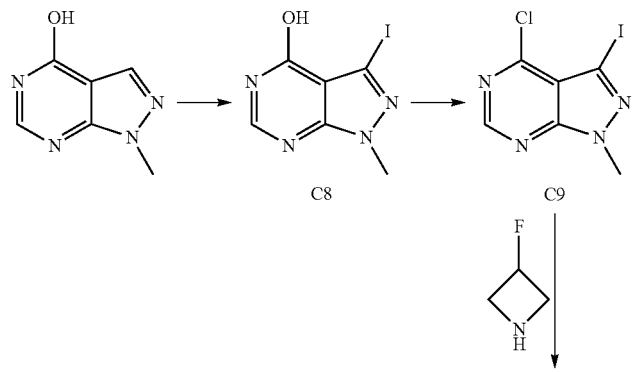

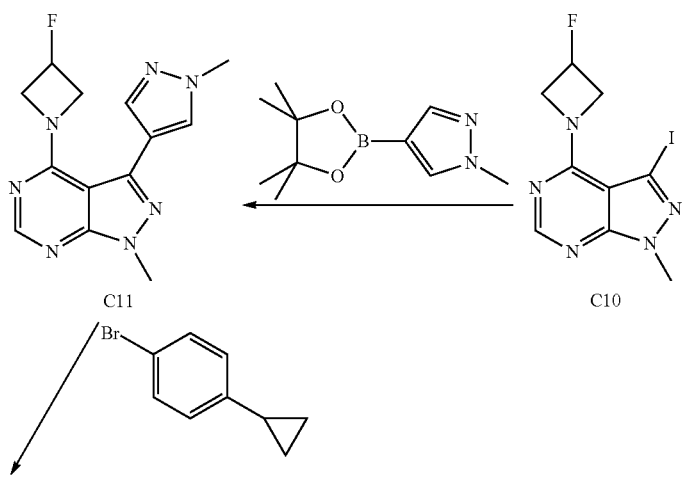

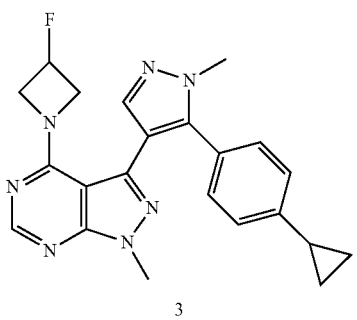

3

Step 1: Synthesis of 3-iodo-1-methyl-1H-pyrazolo[3,4-d]pyrimidin-4-ol (C8)

1-Methyl-1H-pyrazolo[3,4-d]pyrimidin-4-ol (5.50 g, 36.6 mmol) was combined with N-iodosuccinimide (97%, 12.7 g, 54.8 mmol) and tetrafluoroboric acid (50% solution in water, 23.0 mL, 183 mmol) in acetonitrile (50 mL) and the reaction mixture was heated to reflux for 5 hours. After cooling to room temperature, the reaction mixture was poured portion-wise into water (50 mL) containing sodium bicarbonate (18.6 g, 220 mmol). When gas evolution had ceased, the mixture was filtered, and the dark solid was washed successively with saturated aqueous sodium thiosulfate solution (25 mL) and water (2×25 mL). The resulting solid was dried under vacuum overnight at 50° C. to afford the product as a cream-colored solid. Yield: 9.35 g, 33.9 mmol, 93%. LCMS m/z 277.0 (M+1). $^1$H NMR (500 MHz, DMSO-$d_6$) δ 3.87 (s, 3H), 8.07 (s, 1H), 12.08 (v br s, 1H).

Step 2: Synthesis of 4-chloro-3-iodo-1-methyl-1H-pyrazolo[3,4-d]pyrimidine (C9)

3-Iodo-1-methyl-1H-pyrazolo[3,4-d]pyrimidin-4-ol (C8) (9.35 g, 33.9 mmol), N,N-dimethylformamide (10.5 mL, 135 mmol) and phosphorus oxychloride (9.57 mL, 102 mmol) were combined in 1,2-dichloroethane (90 mL), and the mixture was heated to 80° C. for 2 hours. After cooling to room temperature, it was added portion-wise with vigorous stirring to a beaker containing a chilled mixture (0 to 5° C.) of sodium bicarbonate (28.7 g, 339 mmol) in 2-propanol (90 mL) and water (90 mL). The resulting mixture was stirred at 0 to 5° C. for 6 hours, and then concentrated in vacuo. The resulting solid was collected via filtration, and washed with water to provide the product as a yellow solid. Yield: 8.45 g, 28.7 mmol, 85%. $^1$H NMR (500 MHz, DMSO-$d_6$) δ 4.04 (s, 3H), 8.82 (s, 1H).

Step 3: Synthesis of 4-(3-fluoroazetidin-1-yl)-3-iodo-1-methyl-1H-pyrazolo[3,4-d]pyrimidine (C10)

4-Chloro-3-iodo-1-methyl-1H-pyrazolo[3,4-d]pyrimidine (C9) (2.00 g, 6.79 mmol), 3-fluoroazetidine (833 mg, 7.46 mmol), saturated aqueous sodium bicarbonate solution (30 mL), and tetrahydrofuran (40 mL) were combined and allowed to stir at room temperature for 18 hours. After removal of volatiles in vacuo, the residue was diluted with water. Filtration provided the product as a tan solid. Yield: 1.91 g, 5.73 mmol, 84%. LCMS m/z 334.0 (M+1). $^1$H NMR (400 MHz, DMSO-$d_6$) δ 3.91 (s, 3H), 4.47-4.63 (m, 2H), 4.75-4.90 (m, 2H), 5.44-5.64 (m, 1H, $J_{HF}$=58.0 Hz), 8.31 (s, 1H).

Step 4: Synthesis of 4-(3-fluoroazetidin-1-yl)-1-methyl-3-(1-methyl-1H-pyrazol-4-yl)-1H-pyrazolo[3,4-d]pyrimidine (C11)

4-(3-Fluoroazetidin-1-yl)-3-iodo-1-methyl-1H-pyrazolo[3,4-d]pyrimidine (C10) (500 mg, 1.50 mmol), 1-methyl-4-(4,4,5,5-tetramethyl-1,3,2-dioxaborolan-2-yl)-1H-pyrazole (910 mg, 2.63 mmol), tris(dibenzylideneacetone)dipalladium(0) (98%, 56 mg, 0.060 mmol), and tricyclohexylphosphine (96%, 35.1 mg, 0.120 mmol) were combined in 1,4-dioxane (10 mL). An aqueous solution of potassium phosphate (97%, 657 mg, 3.00 mmol) in water (5 mL) was added, and the reaction mixture was subjected to microwave irradiation at 150° C. and 200 W for 90 minutes. The reaction mixture was partitioned between ethyl acetate (20 mL) and aqueous phosphate buffer (20 mL), and the aqueous layer was extracted with ethyl acetate (2×20 mL) and dichloromethane (2×20 mL). The combined organic layers were dried over sodium sulfate, filtered, and concentrated in vacuo. Purification via silica gel chromatography [Gradient: 35% to 100% (10% methanol in ethyl acetate) in heptane] afforded the product as a glass. Yield: 302.3 mg, 1.05 mmol, 70%. LCMS m/z 288.1 (M+1). $^1$H NMR (400 MHz, DMSO-$d_6$) δ 3.83-3.92 (m, 2H), 3.93 (s, 6H), 4.14-4.26 (m, 2H), 5.23-5.43 (m, 1H, $J_{HF}$=58.0 Hz), 7.63 (d, J=0.6 Hz, 1H), 7.99 (br s, 1H), 8.35 (s, 1H).

Step 5: Synthesis of 3-[5-(4-cyclopropylphenyl)-1-methyl-1H-pyrazol-4-yl]-4-(3-fluoroazetidin-1-yl)-1-methyl-1H-pyrazolo[3,4-d]pyrimidine)

4-(3-Fluoroazetidin-1-yl)-1-methyl-3-(1-methyl-1H-pyrazol-4-yl)-1H-pyrazolo[3,4-d]pyrimidine (C11) (300 mg, 1.04 mmol), 1-bromo-4-cyclopropylbenzene (617 mg, 3.13 mmol), and potassium carbonate (289 mg, 2.09 mmol) were combined in 1,4-dioxane (7 mL). Palladium(II) acetate (98%, 50.2 mg, 0.219 mmol) was added, and the reaction mixture was heated at 100° C. for 48 hours. Solids were removed via filtration, and the filtrate was concentrated in vacuo. Purification using silica gel chromatography [Gradient: 25% to 50% (10% methanol in ethyl acetate) in heptane] provided the product as a glass. Yield: 205.3 mg, 0.509 mmol, 49%. LCMS m/z 404.2 (M+1). $^1$H NMR (400 MHz, CD$_3$OD) δ 0.61-0.66 (m, 2H), 0.91-0.97 (m, 2H), 1.81-1.89 (m, 1H), 3.77-3.95 (br m, 2H), 3.91 (s, 3H), 3.95 (s, 3H), 4.07-4.26 (br m, 2H), 5.15-5.36 (m, 1H, $J_{HF}$=57.5 Hz), 7.05 (br d, J=8.2 Hz, 2H), 7.23 (br d, J=8.4 Hz, 2H), 7.71 (s, 1H), 8.20 (s, 1H).

Example 4
4-(Azetidin-1-yl)-1-methyl-3-{1-methyl-5-[5-(trifluoromethyl)pyridin-2-yl]-1H-pyrazol-4-yl}-1H-pyrazolo[3,4-d]pyrimidine
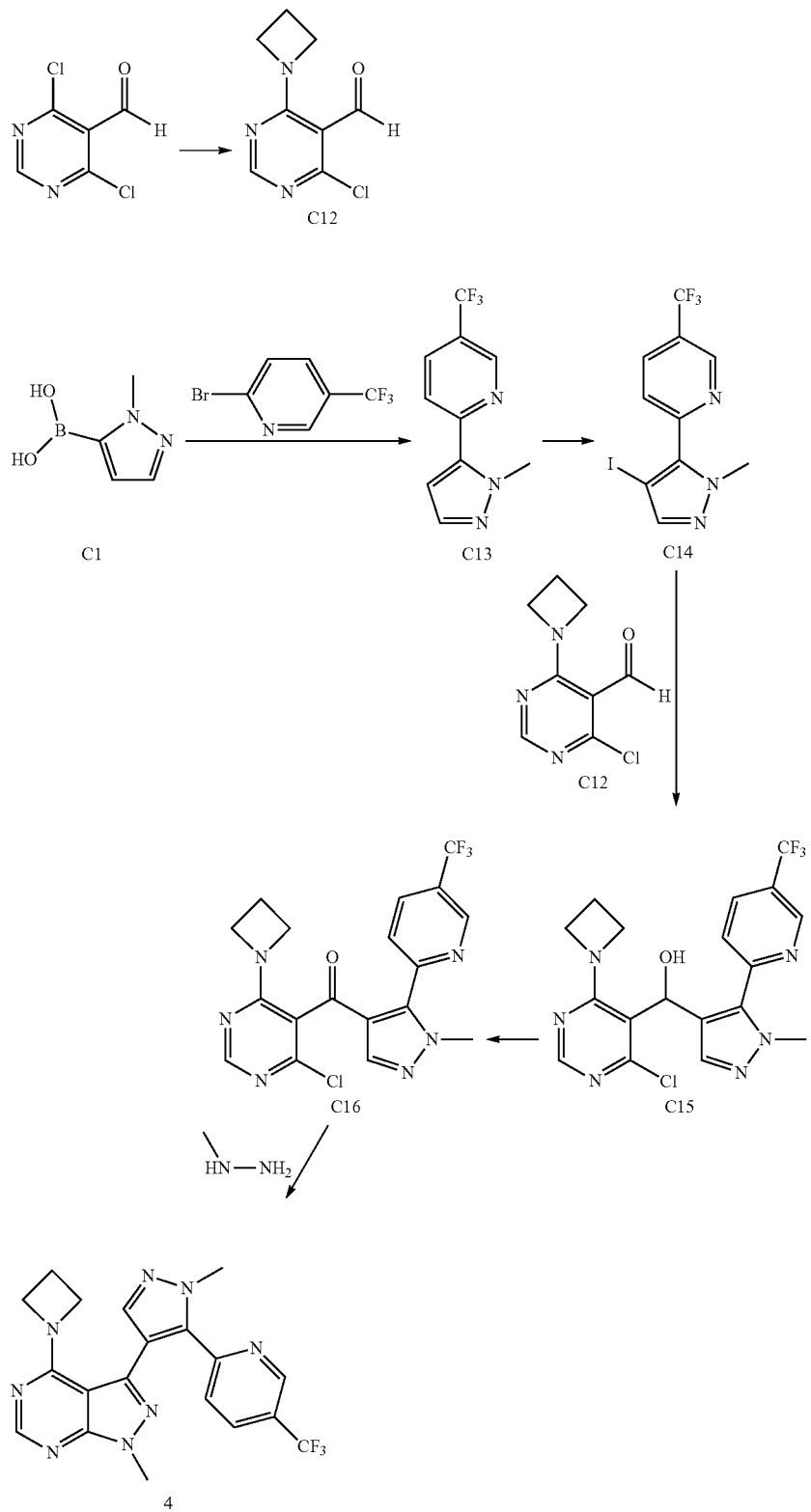

Step 1: Synthesis of 4-(azetidin-1-yl)-6-chloropyrimidine-5-carbaldehyde (C12)

To a solution of 4,6-dichloropyrimidine-5-carbaldehyde (1.00 g, 5.65 mmol) in chloroform at 0° C. were added azetidine (99%, 0.392 mL, 5.71 mmol) and triethylamine (5 drops). The reaction mixture was allowed to warm to room temperature and then stirred for 18 hours. The reaction mixture was filtered, and the filtrate was purified by silica gel chromatography (Gradient: 0% to 100% ethyl acetate in heptane) to provide the product. Yield: 880 mg, 4.45 mmol, 79%. LCMS m/z 198.1, 200.1 (M+1). $^1$H NMR (400 MHz, CD$_3$OD) δ 2.34-2.43 (m, 2H), 4.12-4.33 (br m, 4H), 8.30 (s, 1H), 10.28 (s, 1H).

Step 2: Synthesis of 2-(1-methyl-1H-pyrazol-5-yl)-5-(trifluoromethyl)pyridine (C13)

(1-Methyl-1H-pyrazol-5-yl)boronic acid (C1) (1.00 g, 7.94 mmol), 2-bromo-5-(trifluoromethyl)pyridine (1.79 g, 7.92 mmol), dichlorobis(triphenylphosphine)palladium(II) (279 mg, 0.397 mmol), and sodium carbonate (3.37 g, 31.8 mmol) were combined in 1,2-dimethoxyethane (30 mL) and water (3 mL), and the reaction mixture was heated at reflux for 18 hours. After the reaction had cooled to room temperature, it was concentrated in vacuo, diluted with additional water, and extracted with ethyl acetate (2×300 mL). The combined organic layers were washed with saturated aqueous sodium chloride solution, dried over sodium sulfate, filtered, and concentrated under reduced pressure. Purification via silica gel chromatography (Gradient: 0% to 100% ethyl acetate in heptane) provided the product. Yield: 630 mg, 2.77 mmol, 35%. $^1$H NMR (400 MHz, CD$_3$OD) δ 3.95 (s, 3H), 6.60 (d, J=2.2 Hz, 1H), 7.58 (d, J=2.0 Hz, 1H), 7.94 (br d, J=8.2 Hz, 1H), 8.19-8.23 (m, 1H), 8.89 (br d, J=2 Hz, 1H).

Step 3: Synthesis of 2-(4-iodo-1-methyl-1H-pyrazol-5-yl)-5-(trifluoromethyl)pyridine (C14)

N-Iodosuccinimide (95%, 427 mg, 1.80 mmol) was added to a mixture of 2-(1-methyl-1H-pyrazol-5-yl)-5-(trifluoromethyl)pyridine (C13) (390 mg, 1.72 mmol) and acetic acid (4 mL), and the reaction mixture was heated at 70° C. for 1 hour. The mixture was concentrated in vacuo and subjected to silica gel chromatography (Gradient: 0% to 100% ethyl acetate in heptane) to afford the product as a white solid. Yield: 524 mg, 1.48 mmol, 86%. APCI m/z 353.8 (M+1). $^1$H NMR (400 MHz, CD$_3$OD) δ 3.89 (s, 3H), 7.66 (s, 1H), 8.00 (br d, J=8 Hz, 1H), 8.17 (br dd, J=8, 2 Hz, 1H), 8.83 (br d, J=2 Hz, 1H).

Step 4: Synthesis of [4-(azetidin-1-yl)-6-chloropyrimidin-5-yl]{1-methyl-5-[5-(trifluoromethyl)pyridin-2-yl]-1H-pyrazol-4-yl}methanol (C15)

n-Butyllithium (2.5 M solution in hexanes, 74 μL, 0.185 mmol) was slowly added drop-wise to a −78° C. solution of 2-(4-iodo-1-methyl-1H-pyrazol-5-yl)-5-(trifluoromethyl)pyridine (C14) (50 mg, 0.14 mmol) in tetrahydrofuran (2 mL). The reaction mixture was allowed to stir at −78° C. for 1 hour, and then a solution of 4-(azetidin-1-yl)-6-chloropyrimidine-5-carbaldehyde (C12) (28.1 mg, 0.142 mmol) in tetrahydrofuran (1 mL) was added. Stirring was continued for 1.5 hours at −78° C., then water was added, and the reaction mixture was removed from the cooling bath. The aqueous layer was extracted with ethyl acetate and the combined organic layers were washed with saturated aqueous sodium chloride solution, dried, filtered, and concentrated in vacuo. Purification using silica gel chromatography (Eluent: 94:5:1 dichloromethane/methanol/triethylamine) provided the product. Yield: 40 mg, 0.094 mmol, 67%. LCMS m/z 425.2, 427.2 (M+1). $^1$H NMR (400 MHz, CD$_3$OD) δ 2.17-2.26 (m, 2H), 3.72 (s, 3H), 3.89-3.97 (m, 2H), 4.23-4.31 (m, 2H), 6.32 (s, 1H), 7.58 (s, 1H), 7.79 (br d, J=8 Hz, 1H), 7.85 (s, 1H), 7.92 (br dd, J=8, 2 Hz, 1H), 8.58 (br d, J=2 Hz, 1H).

Step 5: Synthesis of [4-(azetidin-1-yl)-6-chloropyrimidin-5-yl]{1-methyl-5-[5-(trifluoromethyl)pyridin-2-yl]-1H-pyrazol-4-yl}methanone (C16)

A solution of [4-(azetidin-1-yl)-6-chloropyrimidin-5-yl]{1-methyl-5-[5-(trifluoromethyl)pyridin-2-yl]-1H-pyrazol-4-yl}methanol (C15) (30 mg, 0.071 mmol) in dichloromethane (3 mL) was cooled to 0° C. and Dess-Martin periodinane (33.1 mg, 0.078 mmol) was added portion-wise. After completion of the addition, the reaction mixture was stirred for 1 hour at 0° C., then warmed to room temperature and stirred for an additional 18 hours. The reaction mixture was diluted with dichloromethane, and then quenched with aqueous sodium bicarbonate solution (1 mL) and aqueous sodium thiosulfate solution (1 mL). The organic layer was dried over sodium sulfate, filtered, and concentrated under reduced pressure. Chromatographic purification using silica gel [Gradient: 0% to 100% (95:2.5:2.5 ethyl acetate/methanol/triethylamine) in heptane] afforded the product. Yield: 29 mg, 0.069 mmol, 97%. LCMS m/z 423.1, 425.2 (M+1). $^1$H NMR (400 MHz, CD$_3$OD) δ 2.30-2.39 (m, 2H), 3.78 (s, 3H), 3.99-4.07 (m, 4H), 7.89 (d, J=8.2 Hz, 1H), 8.00-8.13 (m, 3H), 8.72 (br s, 1H).

Step 6: Synthesis of 4-(azetidin-1-yl)-1-methyl-3-{1-methyl-5-[5-(trifluoromethyl)pyridin-2-yl]-1H-pyrazol-4-yl}-1H-pyrazolo[3,4-d]pyrimidine Methylhydrazine (98%, 0.254 mL, 4.73 mmol) was added to a solution of [4-(azetidin-1-yl)-6-chloropyrimidin-5-yl]{1-methyl-5-[5-(trifluoromethyl)pyridin-2-yl]-1H-pyrazol-4-yl}methanone (C16) (200 mg, 0.473 mmol) in 1,4-dioxane (4 mL), and the reaction mixture was allowed to stir for 18 hours at room temperature. After removal of solvent in vacuo, the residue was chromatographed on silica gel to provide the product as a solid. Yield: 120 mg, 0.290 mmol, 61%. LCMS m/z 415.0 (M+1). $^1$H NMR (400 MHz, CD$_3$OD) δ 2.25-2.34 (m, 2H), 3.79-4.04 (br m, 4H), 3.94 (s, 3H), 3.98 (s, 3H), 7.80 (s, 1H), 7.85 (d, J=8.2 Hz, 1H), 8.12-8.16 (m, 1H), 8.17 (s, 1H), 8.77-8.79 (m, 1H).

Example 5
(3R)-1-{3-[1-(4-Ethylphenyl)-1H-imidazol-5-yl]-1-methyl-1H-pyrazolo[3,4-d]pyrimidin-4-yl}-N,N-dimethylpyrrolidin-3-amine
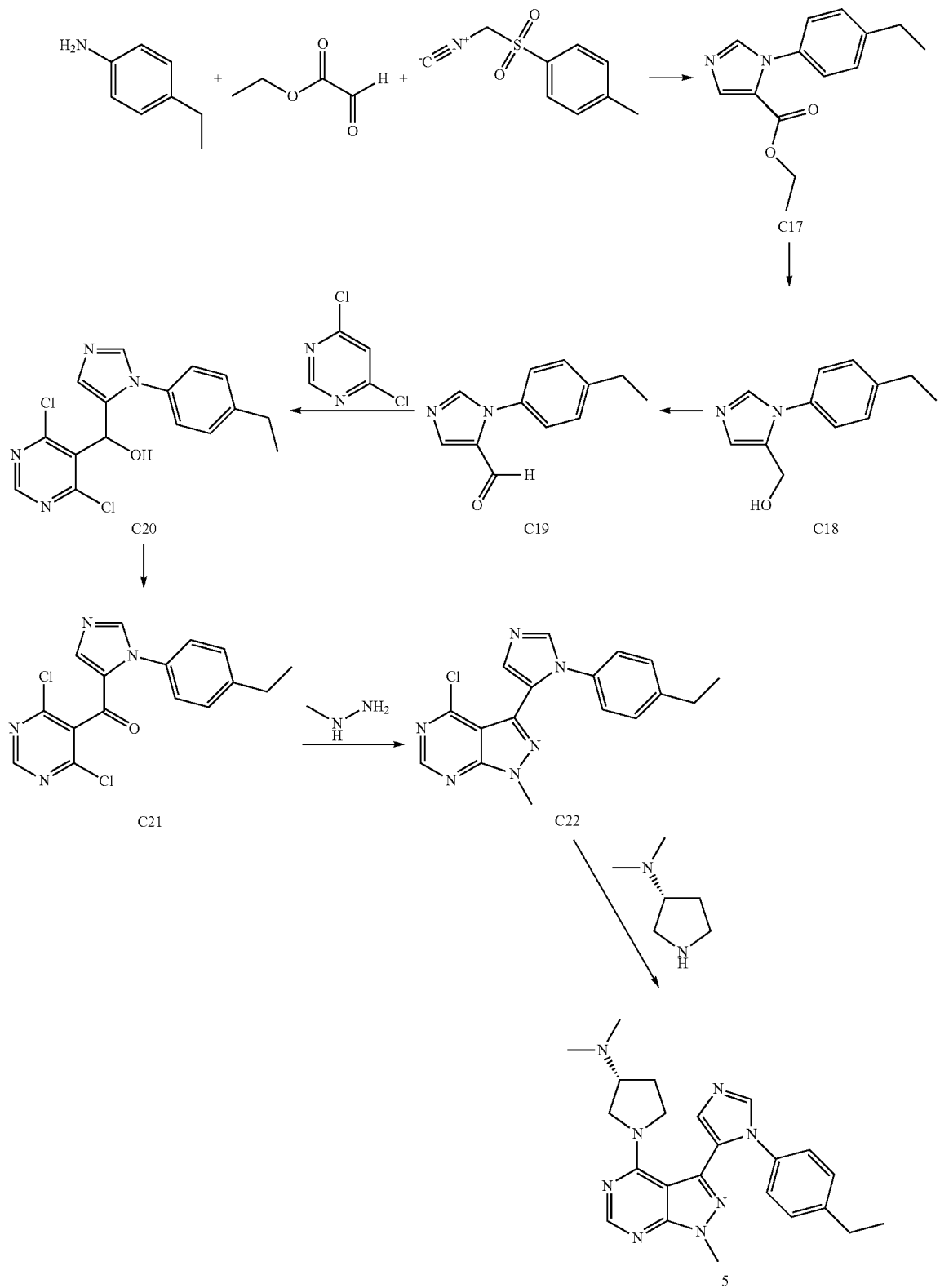

Step 1: Synthesis of ethyl 1-(4-ethylphenyl)-1H-imidazole-5-carboxylate (C17)

4-Ethylaniline (2.08 mL, 16.6 mmol) and ethyl oxoacetate (50% solution in toluene, 3.30 mL, 16.6 mmol) were combined in ethanol (40 mL) and stirred at room temperature for 3 hours. Potassium carbonate (5.75 g, 41.6 mmol) and isocyanomethyl 4-methylphenyl sulfone (98%, 3.98 g, 20.0 mmol) were added and the reaction mixture was heated to reflux for 3 hours. After cooling to room temperature, the reaction mixture was filtered through Celite. The filtrate was concentrated in vacuo, dissolved in ethyl acetate, washed with water, dried over magnesium sulfate, filtered, and concentrated under reduced pressure. Purification via silica gel chromatography (Gradient: 0% to 33% ethyl acetate in heptane) afforded the product as a clear brown oil that solidified upon standing. Yield: 3.03 g, 12.4 mmol, 75%. LCMS m/z 245.0 (M+1). $^1$H NMR (400 MHz, CDCl$_3$) δ 1.24 (t, J=7.1 Hz, 3H), 1.29 (t, J=7.6 Hz, 3H), 2.73 (q, J=7.6 Hz, 2H), 4.21 (q, J=7.1 Hz, 2H), 7.27 (br AB quartet, $J_{AB}$=8.6 Hz, $\Delta v_{AB}$=24 Hz, 4H), 7.66 (d, J=1.1 Hz, 1H), 7.85 (d, J=1.1 Hz, 1H).

Step 2: Synthesis of [1-(4-ethylphenyl)-1H-imidazol-5-yl]methanol (C18)

To a −78° C. solution of ethyl 1-(4-ethylphenyl)-1H-imidazole-5-carboxylate (C17) (6.5 g, 27 mmol) in tetrahydrofuran (45 mL) was added lithium aluminum hydride (1 M solution in tetrahydrofuran, 27 mL, 27 mmol), and the reaction mixture was stirred at −78° C. for 0.5 hours, then warmed to room temperature and stirred for an additional 2 hours. Saturated aqueous potassium tartrate solution was added to quench the reaction. The aqueous layer was extracted with ethyl acetate (10 mL), and the combined organic layers were dried over sodium sulfate, filtered, and concentrated in vacuo. Purification of the resulting pale yellow oil using silica gel chromatography (Gradient: 0% to 5% methanol in ethyl acetate) provided the product. Yield: 3.8 g, 18.8 mmol, 70%. LCMS m/z 203.0 (M+1). $^1$H NMR (500 MHz, CDCl$_3$) δ 1.29 (t, J=7.6 Hz, 3H), 2.73 (q, J=7.6 Hz, 2H), 4.57 (s, 2H), 2.35-2.53 (br s, 1H), 7.13-7.14 (br s, 1H), 7.35 (br AB quartet, $J_{AB}$=8.5 Hz, $\Delta v_{AB}$=27 Hz, 4H), 7.62 (br s, 1H).

Step 3: Synthesis of 1-(4-ethylphenyl)-1H-imidazole-5-carbaldehyde (C19)

A solution of [1-(4-ethylphenyl)-1H-imidazol-5-yl]methanol (C18) (2.50 g, 12.4 mmol) in dichloromethane (15 mL) was treated with activated manganese(IV) oxide (96%, 11.1 g, 123 mmol), and the mixture was stirred at room temperature for 24 hours. The reaction mixture was then filtered through Celite and the filter pad was washed with dichloromethane. The combined filtrates were dried over magnesium sulfate, filtered, and concentrated in vacuo. Purification was carried out by chromatography on silica gel (Gradient: 30% to 80% ethyl acetate in heptane) to afford the product. Yield: 1.8 g, 9.0 mmol, 73%. LCMS m/z 201.0 (M+1). $^1$H NMR (400 MHz, CDCl$_3$) δ 1.31 (t, J=7.6 Hz, 3H), 2.75 (q, J=7.6 Hz, 2H), 7.26-7.30 (m, 2H, assumed; partially obscured by solvent peak), 7.32-7.36 (m, 2H), 7.77 (dd, J=0.8, 0.8 Hz, 1H), 7.94 (d, J=0.9 Hz, 1H), 9.76 (d, J=0.8 Hz, 1H).

Step 4: Synthesis of (4,6-dichloropyrimidin-5-yl)[1-(4-ethylphenyl)-1H-imidazol-5-yl]methanol (C20)

1-(4-Ethylphenyl)-1H-imidazole-5-carbaldehyde (C19) was converted to the product using a procedure analogous to that described for the synthesis of (4,6-dichloropyrimidin-5-yl)[1-methyl-5-(4-methylphenyl)-1H-pyrazol-4-yl]methanol (C4) in Example 1, step 4. The crude product, a yellow solid, was washed with a 1:1 mixture of heptane and ethyl acetate to afford the product. Yield: 473 mg, 1.35 mmol, 74%. LCMS m/z 348.9 (M+1). $^1$H NMR (500 MHz, CDCl$_3$) δ 1.29 (t, J=7.6 Hz, 3H), 2.73 (q, J=7.6 Hz, 2H), 6.27 (br s, 1H), 7.14-7.15 (m, 1H), 7.28-7.33 (m, 4H), 7.69 (d, J=0.7 Hz, 1H), 8.68 (s, 1H).

Step 5: Synthesis of (4,6-dichloropyrimidin-5-yl)[1-(4-ethylphenyl)-1H-imidazol-5-yl]methanone (C21)

(4,6-Dichloropyrimidin-5-yl)[1-(4-ethylphenyl)-1H-imidazol-5-yl]methanol (C20) was converted to the product using a procedure analogous to that described for the synthesis of (4,6-dichloropyrimidin-5-yl)[1-methyl-5-(4-methylphenyl)-1H-pyrazol-4-yl]methanone (C5) in Example 1, step 5, except that the ethyl acetate layer was washed with aqueous sodium bicarbonate solution rather than aqueous sodium hydroxide solution. Recrystallization was not carried out in this case; the product was obtained as a solid. Yield: 701 mg, 2.02 mmol, 94%. LCMS m/z 346.9 (M+1). $^1$H NMR (500 MHz, CDCl$_3$) δ 1.31 (t, J=7.6 Hz, 3H), 2.75 (q, J=7.6 Hz, 2H), 7.30-7.36 (m, 4H), 7.61 (br s, 1H), 7.85 (d, J=0.8 Hz, 1H), 8.85 (s, 1H).

Step 6: Synthesis of 4-chloro-3-[1-(4-ethylphenyl)-1H-imidazol-5-yl]-1-methyl-1H-pyrazolo[3,4-d]pyrimidine (C22)

A solution of (4,6-dichloropyrimidin-5-yl)[1-(4-ethylphenyl)-1H-imidazol-5-yl]methanone (C21) (136 mg, 0.392 mmol) in acetonitrile (3 mL) was added to a solution of methylhydrazine (18.1 mg, 0.393 mmol) in acetonitrile (3 mL). After addition of pyridine (41 mg, 0.52 mmol), the reaction mixture was stirred at room temperature for 1 hour and then concentrated in vacuo. Purification via silica gel chromatography (Gradient: 0% to 20% ethyl acetate in heptane) afforded the product, along with recovered starting material (35 mg, 0.10 mmol). Yield: 81 mg, 0.24 mmol, 61% (82% based on recovered starting material). LCMS m/z 339.0 (M+1). $^1$H NMR (500 MHz, CDCl$_3$) δ 1.21 (t, J=7.6 Hz, 3H), 2.62 (q, J=7.6 Hz, 2H), 4.11 (s, 3H), 7.11-7.15 (m, 4H), 7.52 (d, J=0.8 Hz, 1H), 7.85 (d, J=1.0 Hz, 1H), 8.73 (s, 1H).

Step 7: Synthesis of (3R)-1-{3-[1-(4-ethylphenyl)-1H-imidazol-5-yl]-1-methyl-1H-pyrazolo[3,4-d]pyrimidin-4-yl}-N,N-dimethylpyrrolidin-3-amine (5)

(3R)—N,N-Dimethylpyrrolidin-3-amine (12.4 mg, 0.109 mmol) and N,N-diisopropylethylamine (14.5 mg, 0.109 mmol) were added to a solution of 4-chloro-3-[1-(4-ethylphenyl)-1H-imidazol-5-yl]-1-methyl-1H-pyrazolo[3,4-d]pyrimidine (C22) (37 mg, 0.11 mmol) in acetonitrile (1 mL), and the reaction mixture was stirred at room temperature for 2 hours. After removal of volatiles in vacuo, the residue was chromatographed on silica gel (Gradient: 0% to 15% ethyl acetate in methanol) to afford the product as a glass. Yield: 13 mg, 0.031 mmol, 28%. LCMS m/z 417.1 (M+1). $^1$H NMR (500 MHz, CDCl$_3$), characteristic peaks: δ 1.17 (t, J=7.6 Hz, 3H), 2.49-2.65 (m, 8H), 3.51-3.61 (br m, 1H), 3.72-3.81 (br m, 1H), 4.08 (s, 3H), 7.10 (br d, J=8.3 Hz, 2H), 7.22-7.29 (m, 2H, assumed; partially obscured by solvent peak), 7.40 (br s, 1H), 7.90 (br s, 1H), 8.29 (s, 1H).

Example 6

4-(Azetidin-1-yl)-3-{5-[4-(difluoromethyl)phenyl]-1-methyl-1H-pyrazol-4-yl}-1-methyl-1H-pyrazolo[3,4-d]pyrimidine

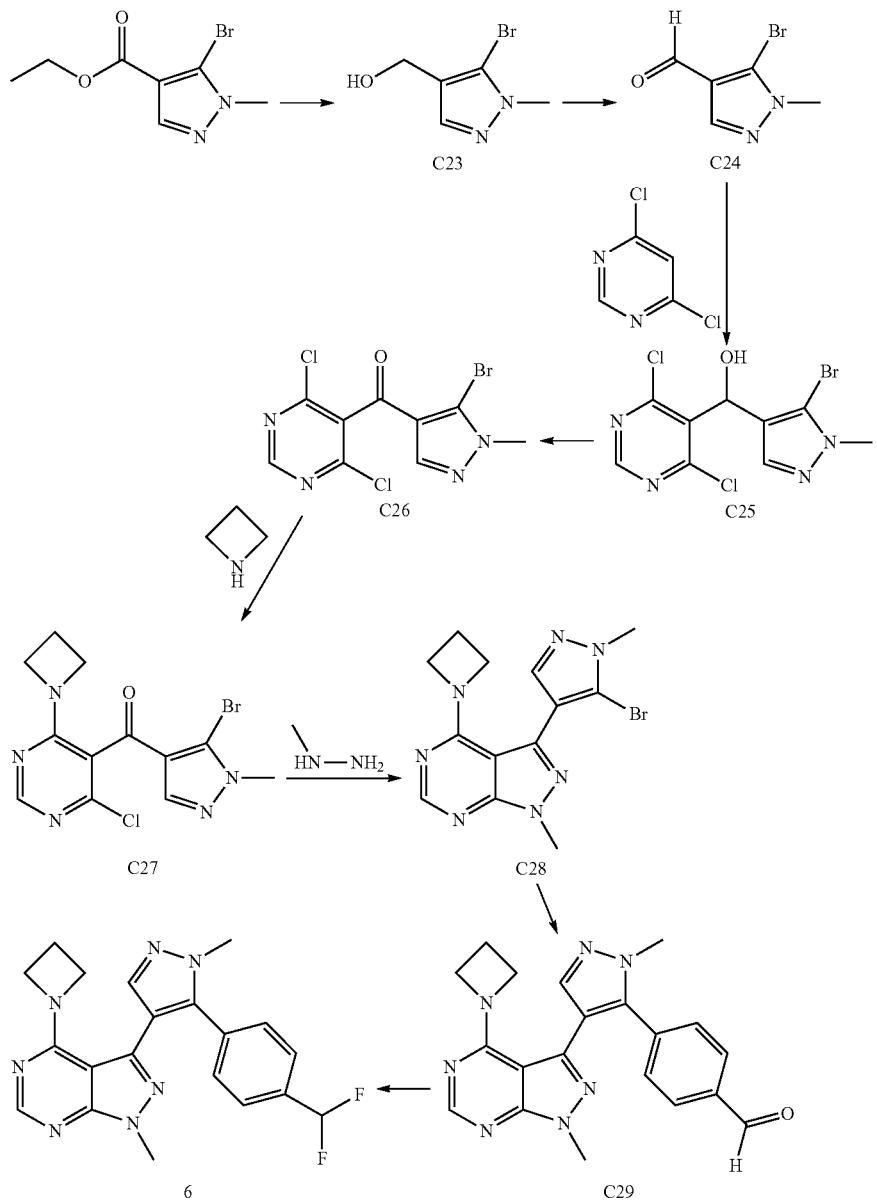

Step 1: Synthesis of (5-bromo-1-methyl-1H-pyrazol-4-yl)methanol (C23)

A solution of ethyl 5-bromo-1-methyl-1H-pyrazole-4-carboxylate (2.00 g, 8.58 mmol) in tetrahydrofuran (30 mL) at 0° C. was treated with diisobutylaluminum hydride (1 M solution in tetrahydrofuran, 18.9 mL, 18.9 mmol), and the mixture was allowed to warm to room temperature and stir for 18 hours. Saturated aqueous sodium potassium tartrate solution was added, and stirring was continued for 4 hours. The aqueous layer was extracted with ethyl acetate, and the combined organic layers were dried over magnesium sulfate, filtered, and concentrated under reduced pressure. Purification via silica gel chromatography (Eluent: 100:1 ethyl acetate/methanol) afforded the product. Yield: 1.63 g, 8.53 mmol, 99%. LCMS m/z 192.9 (M+1). $^1$H NMR (400 MHz, CDCl$_3$) δ 2.44 (s, 1H), 3.84 (s, 3H), 4.48 (s, 2H), 7.51 (s, 1H).

Step 2: Synthesis of 5-bromo-1-methyl-1H-pyrazole-4-carbaldehyde (C24)

(5-Bromo-1-methyl-1H-pyrazol-4-yl)methanol (C23) was converted to the product using a procedure analogous to that described for the synthesis of 1-(4-ethylphenyl)-1H-imidazole-5-carbaldehyde (C19) in Example 5, step 3. In this case, no chromatography was carried out. Yield: 1.46 g, 7.72 mmol, 92%. LCMS m/z 191.2 (M+1). $^1$H NMR (400 MHz, CDCl$_3$) δ 3.93 (s, 3H), 7.96 (s, 1H), 9.76 (s, 1H).

Step 3: Synthesis of (5-bromo-1-methyl-1H-pyrazol-4-yl)(4,6-dichloropyrimidin-5-yl)methanol (C25)

5-Bromo-1-methyl-1H-pyrazole-4-carbaldehyde (C24) was converted to the product using a procedure analogous to that described for the synthesis of (4,6-dichloropyrimidin-5-yl)[1-methyl-5-(4-methylphenyl)-1H-pyrazol-4-yl]methanol (C4) in Example 1, step 4. In this case the product was purified not by recrystallization, but using silica gel chromatography (Eluent: 10:1 heptane/ethyl acetate, then 2:1 heptane/ethyl acetate). Yield: 1.26 g, 3.73 mmol, 70%. LCMS m/z 339.1 (M+1). $^1$H NMR (400 MHz, CDCl$_3$) δ 2.4-3.0 (v br s, 1H), 3.88 (s, 3H), 6.36 (s, 1H), 7.56 (s, 1H), 8.74 (s, 1H).

Step 4: Synthesis of (5-bromo-1-methyl-1H-pyrazol-4-yl)(4,6-dichloropyrimidin-5-yl)methanone (C26)

Dess-Martin periodinane (2.26 g, 5.33 mmol) was added in portions to a solution of (5-bromo-1-methyl-1H-pyrazol-4-yl)(4,6-dichloropyrimidin-5-yl)methanol (C25) (1.20 g, 3.55 mmol) in chloroform (30 mL), and the mixture was stirred for 2 hours. After filtration, the filtrate was concentrated in vacuo, diluted with ethyl acetate (300 mL), washed with saturated aqueous sodium hydrogen sulfite solution (3×150 mL), and washed with saturated aqueous sodium carbonate solution. The organic layer was dried over magnesium sulfate, filtered, and concentrated under reduced pressure. Purification using silica gel chromatography (Eluent: 5:1 heptane/ethyl acetate) provided the product. Yield: 1.16 g, 3.45 mmol, 97%. LCMS m/z 337.1 (M+1). $^1$H NMR (400 MHz, CDCl$_3$) δ 3.97 (s, 3H), 7.92 (s, 1H), 8.90 (s, 1H).

Step 5: Synthesis of [4-(azetidin-1-yl)-6-chloropyrimidin-5-yl](5-bromo-1-methyl-1H-pyrazol-4-yl)methanone (C27)

(5-Bromo-1-methyl-1H-pyrazol-4-yl)(4,6-dichloropyrimidin-5-yl)methanone (C26) (1.14 g, 3.39 mmol) was combined with azetidine (98%, 0.212 mL, 3.08 mmol) and N,N-diisopropylethylamine (0.645 mL, 3.70 mmol) in acetonitrile (30 mL) at 0° C. The mixture was then allowed to warm to room temperature and stir for 18 hours. After removal of volatiles in vacuo, the residue was purificed via silica gel chromatography (Eluent: 100:1 ethyl acetate/methanol) to afford the product. Yield: 1.07 g, 3.00 mmol, 97%. LCMS m/z 356.2, 358.2, 360.2 (M+1). $^1$H NMR (400 MHz, CDCl$_3$) δ 2.25-2.36 (m, 2H), 3.94 (s, 3H), 3.96-4.09 (br m, 4H), 7.85 (br s, 1H), 8.37 (s, 1H).

Step 6: Synthesis of 4-(azetidin-1-yl)-3-(5-bromo-1-methyl-1H-pyrazol-4-yl)-1-methyl-1H-pyrazolo[3,4-d]pyrimidine (C28)

A mixture of methylhydrazine (98%, 1.57 mL, 29.2 mmol) and [4-(azetidin-1-yl)-6-chloropyrimidin-5-yl](5-bromo-1-methyl-1H-pyrazol-4-yl)methanone (C27) (1.04 g, 2.92 mmol) in pyridine (15 mL) was heated to 85° C. for 16 hours. Volatiles were removed in vacuo and the residue was purified using silica gel chromatography (Gradient: 0.5% to 5% methanol in ethyl acetate) to provide the product as a solid. Yield: 960 mg, 2.76 mmol, 94%. LCMS m/z 348.3, 350.2 (M+1). $^1$H NMR (400 MHz, CDCl$_3$) δ 2.25-2.34 (m, 2H), 3.84-4.04 (br m, 4H), 3.97 (s, 3H), 4.05 (s, 3H), 7.67 (s, 1H), 8.39 (s, 1H).

Step 7: Synthesis of 4-{4-[4-(azetidin-1-yl)-1-methyl-1H-pyrazolo[3,4-d]pyrimidin-3-yl]-1-methyl-1H-pyrazol-5-yl}benzaldehyde (C29)

4-(Azetidin-1-yl)-3-(5-bromo-1-methyl-1H-pyrazol-4-yl)-1-methyl-1H-pyrazolo[3,4-d]pyrimidine (C28) (345 mg, 0.991 mmol), (4-formylphenyl)boronic acid (163 mg, 1.09 mmol), tetrakis(triphenylphosphine)palladium(0) (11.6 mg, 0.0100 mmol), and sodium carbonate (210 mg, 1.98 mmol) were combined in ethanol (10 mL). Water (2 mL) was added, and the reaction mixture was allowed to stir for 18 hours at 100° C. The reaction mixture was concentrated in vacuo and diluted with water. The aqueous layer was extracted with ethyl acetate (3×100 mL), and the combined organic layers were dried over sodium sulfate, filtered, concentrated under reduced pressure, and subjected to silica gel chromatography [Gradient: 0% to 100% (90:5:5 ethyl acetate/methanol/triethylamine) in heptane]. The product was obtained as a mixture with some impurities, and was used in the next step without additional purification. Yield: 270 mg, 0.723 mmol, 73%. APCI m/z 374.0 (M+1). $^1$H NMR (400 MHz, CD$_3$OD), product peaks only: δ 2.25-2.34 (m, 2H), 3.8-4.0 (br m, 4H), 3.95 (s, 3H), 3.96 (s, 3H), 7.61 (br d, J=8.2 Hz, 2H), 7.76 (s, 1H), 7.92 (br d, J=8.4 Hz, 2H), 8.16 (s, 1H), 9.97 (s, 1H).

Step 8: Synthesis of 4-(azetidin-1-yl)-3-{5-[4-(difluoromethyl)phenyl]-1-methyl-1H-pyrazol-4-yl}-1-methyl-1H-pyrazolo[3,4-d]pyrimidine (Diethylamino)sulfur trifluoride (0.116 mL, 0.885 mmol) was added to a solution of 4-{4-[4-(azetidin-1-yl)-1-methyl-1H-pyrazolo[3,4-d]pyrimidin-3-yl]-1-methyl-1H-pyrazol-5-yl}benzaldehyde (C29) (220 mg, 0.589 mmol) in dichloromethane, and the reaction mixture was allowed to stir for 18 hours at room temperature. Additional (diethylamino)sulfur trifluoride (0.05 mL, 0.4 mmol) was introduced into the reaction, and stirring was continued for 1 hour. Solid sodium carbonate was added to the reaction, and the resulting reaction mixture was directly applied to a silica gel column for chromatographic purification [Gradient: 0% to 100% (90:5:5 ethyl acetate/methanol/triethylamine) in heptane], which afforded the product as a white solid. Yield: 130 mg, 0.329 mmol, 56%. LCMS m/z 396.5 (M+1). $^1$H NMR (400 MHz, CD$_3$OD) δ 2.24-2.34 (m, 2H), 3.80-4.02 (m, 4H), 3.93 (s, 3H), 3.95 (s, 3H), 6.75 (t, $J_{HF}$=56.0 Hz, 1H), 7.54 (br AB quartet, $J_{AB}$=8.3 Hz, $\Delta\nu_{AB}$=15 Hz, 4H), 7.74 (s, 1H), 8.16 (s, 1H)

Method A

Preparation of 3-Substituted 1-R$^1$-Substituted 1H-pyrazolo[3,4-d]pyrimidin-4-amines from (4,6-dichloropyrimidin-5-yl)ketones via Amine Addition Followed by Hydrazine Cyclization

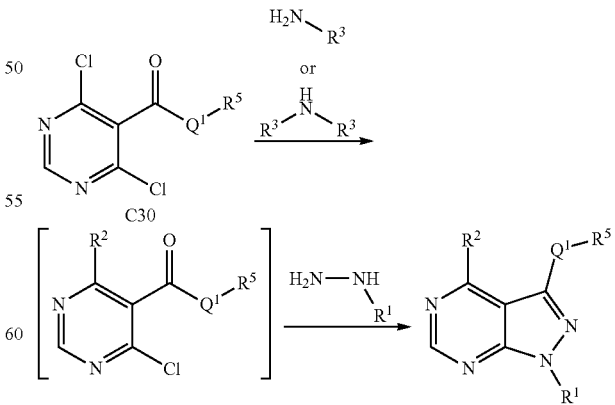

N,N-Diisopropylethylamine (35.2 µL, 200 µmol) was added to a vial containing a solution of 4,6-dichloropyrimidine C30 in acetonitrile (0.333 M, 300 µL, 100 µmol). The requisite amine [H$_2$NR$^3$ or HN(R$^3$)$_2$] (0.333 M, 300 µL, 100

μmol) was then added, and the reaction mixture was capped and shaken at 30° C. for 1.5 hours. When the reaction was deemed complete, as assessed by LCMS, the appropriate hydrazine ($NH_2NHR^1$) (50 μL) was added, followed by additional N,N-diisopropylethylamine (50 μL, 290 μmol), and the mixture was capped and shaken at 70° C. for 16 hours. When the cyclization was complete, as assessed by LCMS, the reaction mixture was filtered and purified by preparative HPLC using an appropriate gradient in one of the following systems: a) Phenomenex Luna C18 column; Mobile phase A: water containing 0.1% trifluoroacetic acid; Mobile phase B: acetonitrile containing 0.1% trifluoroacetic acid; b) Phenomenex Luna C18 AXIA column; Mobile phase A: 20 mM aqueous ammonium bicarbonate; Mobile phase B: 10% water in acetonitrile.

Method B

Preparation of 4-(azetidin-1-yl)-1-methyl-3-(1-methyl-5-Substituted-1H-pyrazol-4-yl)-1H-pyrazolo[3,4-d]pyrimidines via Suzuki Reaction

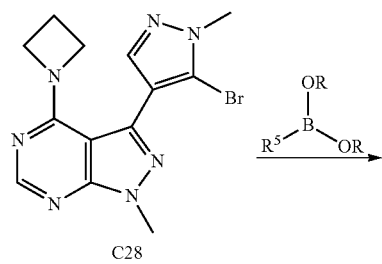

C28

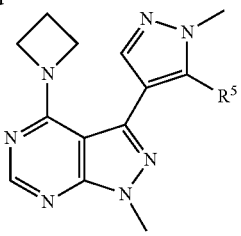

A vial was charged with a solution of the appropriate boronic acid or boronate ester (150 μmol, wherein each R is H or $C_{1-6}$ alkyl, or the two (OR) groups, together with the B atom to which they are attached, form a 5- to 10-membered heterocyclic ring optionally substituted with one or more $C_{1-6}$ alkyl) in 1,4-dioxane (450 μL). 4-(Azetidin-1-yl)-3-(5-bromo-1-methyl-1H-pyrazol-4-yl)-1-methyl-1H-pyrazolo[3,4-d]pyrimidine (C28) in degassed 1,4-dioxane (0.167 M, 450 μL, 75 μmol) was added, followed by sodium carbonate (15.9 mg, 150 μmol). Water (150 μL) was then added, followed by [1,1-bis(di-tert-butylphosphino)ferrocene]dichloropalladium(II) (2.5 mg, 3.8 μmol), and nitrogen was bubbled through the solution for approximately 1 minute. The vial was capped and shaken at 100° C. for 16 hours. After removal of solvent, purification was carried out by preparative HPLC using a Phenomenex Gemini C18 column and an appropriate gradient composed of aqueous ammonium hydroxide (pH 10) and acetonitrile.

Examples 7-60 were prepared using methods substantially analogous to Method A or B or those described for the synthesis of any one of Examples 1-6.

TABLE 1

Examples 7-60

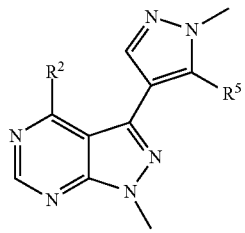

| Example Number | Method | $R^2$ | $R^5$ | Compound Name | $^1$H NMR (400 MHz, $CDCl_3$), δ (ppm); Mass spectrum, observed ion m/z (M + 1) or HPLC retention time (minutes); Mass spectrum m/z (M + 1) (unless otherwise indicated) |
|---|---|---|---|---|---|
| 7 | Ex 1[1] | ![N-methyl pyrrolidine] | ![ethylphenyl] | (3R)-1-{3-[5-(4-ethylphenyl)-1-methyl-1H-pyrazol-4-yl]-1-methyl-1H-pyrazolo[3,4-d]pyrimldin-4-yl}-N,N-dimethylpyrrolidin-3-amine | 1.22 (t, J = 7.6 Hz, 3H), 1.60-1.73 (m, 1H), 2.02-2.11 (m, 1H), 2.17 (br s, 6H), 2.48-2.58 (br m, 1H), 2.63 (q, J = 7.6 Hz, 2H), 2.96-3.12 (br m, 1H), 3.28-3.67 (br m, 3H), 3.89 (s, 3H), 4.02 (s, 3H), 7.18 (br AB quartet, $J_{AB}$ = 8 Hz, $\Delta v_{AB}$ = 22 Hz, 4H), 7.69 (s, 1H), 8.30 (s, 1H); 431.2 |

TABLE 1-continued

Examples 7-60

| Example Number | Method | R² | R⁵ | Compound Name | ¹H NMR (400 MHz, CDCl₃), δ (ppm); Mass spectrum, observed ion m/z (M + 1) or HPLC retention time (minutes); Mass spectrum m/z (M + 1) (unless otherwise indicated) |
|---|---|---|---|---|---|
| 8 | Method A | 3-fluoroazetidin-1-yl | 4-ethylphenyl | 3-[5-(4-ethylphenyl)-1-methyl-1H-pyrazol-4-yl]-4-(3-fluoroazetidin-1-yl)-1-methyl-1H-pyrazolo[3,4-d]pyrimidine | 1.33 min²; 391.9 |
| 9 | Ex 1¹ | azetidin-1-yl | 4-ethylphenyl | 4-(azetidin-1-yl)-3-[5-(4-ethylphenyl)-1-methyl-1H-pyrazol-4-yl]-1-methyl-1H-pyrazolo[3,4-d]pyrimidine | 1.23 (t, J = 7.6 Hz, 3H), 2.21-2.30 (m, 2H), 2.64 (q, J = 7.6 Hz, 2H), 3.78-4.01 (br m, 4H), 3.92 (s, 3H), 4.00 (s, 3H), 7.23 (br AB quartet, J_{AB} = 8.4 Hz, Δv_{AB} = 36 Hz, 4H), 7.67 (s, 1H), 8.32 (s, 1H); 374.2 |
| 10 | Method A³ | 3-(1-methyl-1H-pyrazol-3-yl)azetidin-1-yl | 4-methylphenyl | 1-methyl-3-[1-methyl-5-(4-methylphenyl)-1H-pyrazol-4-yl]-4-[3-(1-methyl-1H-pyrazol-3-yl)azetidin-1-yl]-1H-pyrazolo[3,4-d]pyrimidine | 1.05 min²; 440.5 |
| 11 | Method A | 3-[(cyclopropylmethyl)sulfonyl]pyrrolidin-1-yl | 4-methylphenyl | 4-{3-[(cyclopropylmethyl)sulfonyl]pyrrolidin-1-yl}-1-methyl-3-[1-methyl-5-(4-methylphenyl)-1H-pyrazol-4-yl]-1H-pyrazolo[3,4-d]pyrimidine | 1.31 min²; 492.4 |

TABLE 1-continued

Examples 7-60

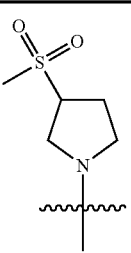

| Example Number | Method | R² | R⁵ | Compound Name | ¹H NMR (400 MHz, CDCl₃), δ (ppm); Mass spectrum, observed ion m/z (M + 1) or HPLC retention time (minutes); Mass spectrum m/z (M + 1) (unless otherwise indicated) |
|---|---|---|---|---|---|
| 12 | Method A | 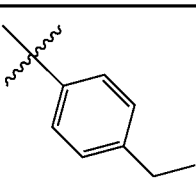 | 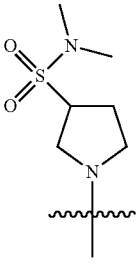 [SMILES: *N1CCC(S(=O)(=O)N(C)C)C1] | 3-[5-(4-ethylphenyl)-1-methyl-1H-pyrazol-4-yl]-1-methyl-4-[3-(methylsulfonyl)pyrrolidin-1-yl]-1H-pyrazolo[3,4-d]pyrimidine | 1.24 min²; 466.4 |
| 13 | Method A | 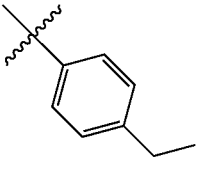 [SMILES: *c1ccc(CC)cc1] | 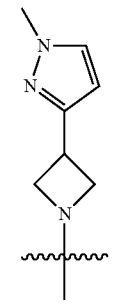 [SMILES: *N1CC(c2ccn(C)n2)C1] | 1-{3-[5-(4-ethylphenyl)-1-methyl-1H-pyrazol-4-yl]-1-methyl-1H-pyrazolo[3,4-d]pyrimidin-4-yl}-N,N-dimethylpyrrolidine-3-sulfonamide | 1.37 min²; 495.4 |
| 14 | Method A³ | 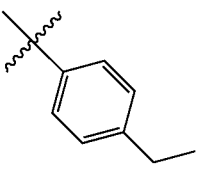 [SMILES: *c1ccc(CC)cc1] | 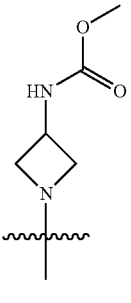 [SMILES: *N1CC(NC(=O)OC)C1] | 3-[5-(4-ethylphenyl)-1-methyl-1H-pyrazol-4-yl]-1-methyl-4-[3-(1-methyl-1H-pyrazol-3-yl)azetidin-1-yl]-1H-pyrazolo[3,4-d]pyrimidine | 1.17 min²; 454.3 |
| 15 | Ex 1⁴ | 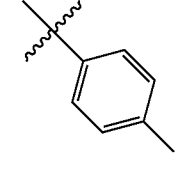 [SMILES: *c1ccc(C)cc1] | 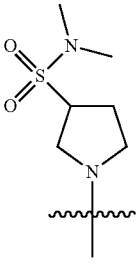 [SMILES: *N1CCC(S(=O)(=O)N(C)C)C1] | methyl (1-{1-methyl-3-[1-methyl-5-(4-methylphenyl)-1H-pyrazol-4-yl]-1H-pyrazolo[3,4-d]pyrimidin-4-yl}azetidin-3-yl)carbamate | 2.35 (s, 3H), 3.64-3.75 (br m, 2H), 3.69 (s, 3H), 3.92 (s, 3H), 4.01 (s, 3H), 4.08-4.21 (br m, 2H), 4.43-4.55 (br m, 1H), 4.96-5.06 (br m, 1H), 7.15-7.19 (m, 2H), 7.23-7.27 (m, 2H), 7.66 (s, 1H), 8.34 (s, 1H); 433.6 |

TABLE 1-continued

Examples 7-60

| Example Number | Method | R² | R⁵ | Compound Name | ¹H NMR (400 MHz, CDCl₃), δ (ppm); Mass spectrum, observed ion m/z (M + 1) or HPLC retention time (minutes); Mass spectrum m/z (M + 1) (unless otherwise indicated) |
|---|---|---|---|---|---|
| 16 | Method A | (3R)-3-acetamido-pyrrolidin-1-yl | 4-ethylphenyl | N-[(3R)-1-{3-[5-(4-ethylphenyl)-1-methyl-1H-pyrazol-4-yl]-1-methyl-1H-pyrazolo[3,4-d]pyrimidin-4-yl}pyrrolidin-3-yl]acetamide | 1.01 min²; 445.3 |
| 17 | Method A⁴ | 3-(methoxycarbonylamino)azetidin-1-yl | 4-ethylphenyl | methyl (1-{3-[5-(4-ethylphenyl)-1-methyl-1H-pyrazol-4-yl]-1-methyl-1H-pyrazolo[3,4-d]pyrimidin-4-yl}azetidin-3-yl)carbamate | 1.17 min²; 447.2 |
| 18 | Method A | 3-(tert-butoxycarbonylamino)azetidin-1-yl | 4-methoxyphenyl | tert-butyl (1-{3-[5-(4-methoxyphenyl)-1-methyl-1H-pyrazol-4-yl]-1-methyl-1H-pyrazolo[3,4-d]pyrimidin-4-yl}azetidin-3-yl)carbamate | 1.23 min²; 491.3 |

TABLE 1-continued

Examples 7-60

| Example Number | Method | R² | R⁵ | Compound Name | ¹H NMR (400 MHz, CDCl₃), δ (ppm); Mass spectrum, observed ion m/z (M + 1) or HPLC retention time (minutes); Mass spectrum m/z (M + 1) (unless otherwise indicated) |
|---|---|---|---|---|---|
| 19 | Ex 1³ | 1-methyl-1H-pyrazol-3-yl azetidine | 4-chloro-3-fluorophenyl | 3-[5-(4-chloro-3-fluorophenyl)-1-methyl-1H-pyrazol-4-yl]-1-methyl-4-[3-(1-methyl-1H-pyrazol-3-yl)azetidin-1-yl]-1H-pyrazolo[3,4-d]pyrimidine | (characteristic peaks) 3.87 (s, 3H), 3.89 (s, 3H), 4.02 (s, 3H), 6.09 (d, J = 2.2 Hz, 1H), 7.10 (ddd, J = 8.2, 2.0, 1.0 Hz, 1H), 7.24-7.28 (m, 1H, assumed; partially obscured by solvent peak), 7.31 (d, J = 2.2 Hz, 1H), 7.37 (dd, J = 8.2, 7.6 Hz, 1H), 7.70 (s, 1H), 8.36 (s, 1H); 478.6, 480.6 |
| 20 | Method A | N,N-dimethylsulfamoyl pyrrolidine | 4-chloro-3-fluorophenyl | 1-{3-[5-(4-chloro-3-fluorophenyl)-1-methyl-1H-pyrazol-4-yl]-1-methyl-1H-pyrazolo[3,4-d]pyrimidin-4-yl}-N,N-dimethylpyrrolidine-3-sulfonamide | 2.90 min⁵; 519 |
| 21 | Method A³ | 1-methyl-1H-pyrazol-3-yl azetidine | 3-fluoro-4-methoxyphenyl | 3-[5-(3-fluoro-4-methoxyphenyl)-1-methyl-1H-pyrazol-4-yl]-1-methyl-4-[3-(1-methyl-1H-pyrazol-3-yl)azetidin-1-yl]-1H-pyrazolo[3,4-d]pyrimidine | 2.514 min⁵; 474 |
| 22 | Method A | (cyclopropylmethyl)sulfonyl pyrrolidine | 4-chloro-3-fluorophenyl | 3-[5-(4-chloro-3-fluorophenyl)-1-methyl-1H-pyrazol-4-yl]-4-{3-[(cyclopropylmethyl)sulfonyl]pyrrolidin-1-yl}-1-methyl-1H-pyrazolo[3,4-d]pyrimidine | 2.966 min⁵; 530 |

TABLE 1-continued

Examples 7-60

|                   |                                                                                                                                                                                                                                                      |
|-------------------|------------------------------------------------------------------------------------------------------------------------------------------------------------------------------------------------------------------------------------------------------|
|                   | $^{1}$H NMR (400 MHz, CDCl$_3$), δ (ppm); Mass spectrum, observed ion m/z (M + 1) or HPLC retention time (minutes); Mass spectrum m/z (M + 1) (unless otherwise indicated) |

| Example Number | Method | R² | R⁵ | Compound Name | (M + 1) (unless otherwise indicated) |
|---|---|---|---|---|---|
| 23 | Ex 1[4] | (methyl carbamate azetidine structure) | (4-cyclopropylphenyl structure) | methyl (1-{3-[5-(4-cyclopropylphenyl)-1-methyl-1H-pyrazol-4-yl]-1-methyl-1H-pyrazolo[3,4-d]pyrimidin-4-yl}azetidin-3-yl)carbamate | 0.67-0.72 (m, 2H), 0.97-1.02 (m, 2H), 1.84-1.91 (m, 1H), 3.62-3.76 (br m, 2H), 3.69 (s, 3H), 3.92 (s, 3H), 4.01 (s, 3H), 4.07-4.21 (br m, 2H), 4.43-4.55 (br m, 1H), 4.97-5.07 (br m, 1H), 7.04 (br d, J = 8.4 Hz, 2H), 7.25 (br d, J = 8.2 Hz, 2H), 7.65 (s, 1H), 8.34 (s, 1H); 459.7 |
| 24 | Method A | (N,N-dimethyl pyrrolidine structure) | (4-cyclopropylphenyl structure) | (3R)-1-{3-[5-(4-cyclopropylphenyl)-1-methyl-1H-pyrazol-4-yl]-1-methyl-1H-pyrazolo[3,4-d]pyrimidin-4-yl}-N,N-dimethylpyrrolidin-3-amine, trifluoroacetate salt | 2.425 min[5]; 443 |
| 25 | Method A | (N,N-dimethylsulfonamide pyrrolidine structure) | (4-cyclopropylphenyl structure) | 1-{3-[5-(4-cyclopropylphenyl)-1-methyl-1H-pyrazol-4-yl]-1-methyl-1H-pyrazolo[3,4-d]pyrimidin-4-yl}-N,N-dimethylpyrrolidine-3-sulfonamide | 2.905 min[5]; 507 |
| 26 | Method A | (N-methylacetamide pyrrolidine structure) | (4-cyclopropylphenyl structure) | N-(1-{3-[5-(4-cyclopropylphenyl)-1-methyl-1H-pyrazol-4-yl]-1-methyl-1H-pyrazolo[3,4-d]pyrimidin-4-yl}pyrrolidin-3-yl)-N-methylacetamide | 2.649 min[5]; 471 |

TABLE 1-continued

Examples 7-60

| Example Number | Method | R² | R⁵ | Compound Name | ¹H NMR (400 MHz, CDCl₃), δ (ppm); Mass spectrum, observed ion m/z (M + 1) or HPLC retention time (minutes); Mass spectrum m/z (M + 1) (unless otherwise indicated) |
|---|---|---|---|---|---|
| 27 | Ex 1 | 3-(methylsulfonyl)pyrrolidin-1-yl | 4-cyclopropylphenyl | 3-[5-(4-cyclopropylphenyl)-1-methyl-1H-pyrazol-4-yl]-1-methyl-4-[3-(methylsulfonyl)pyrrolidin-1-yl]-1H-pyrazolo[3,4-d]pyrimidine | 0.65-0.70 (m, 2H), 0.95-1.00 (m, 2H), 1.81-1.89 (m, 1H), 2.24-2.36 (m, 2H), 2.83 (s, 3H), 3.45-3.74 (m, 5H), 3.91 (s, 3H), 4.06 (s, 3H), 7.01 (br d, J = 8.4 Hz, 2H), 7.25 (br d, J = 8.2 Hz, 2H), 7.68 (s, 1H), 8.31 (s, 1H); 478.6 |
| 28 | Method A⁶ | 3-(1,2-oxazol-5-yl)azetidin-1-yl | 4-cyclopropylphenyl | 3-[5-(4-cyclopropylphenyl)-1-methyl-1H-pyrazol-4-yl]-1-methyl-4-[3-(1,2-oxazol-5-yl)azetidin-1-yl]-1H-pyrazolo[3,4-d]pyrimidine | 2.845 min⁵; 453 |
| 29 | Method A | 3-[(cyclopropylmethyl)sulfonyl]pyrrolidin-1-yl | 4-cyclopropylphenyl | 4-{3-[(cyclopropylmethyl)sulfonyl]pyrrolidin-1-yl}-3-[5-(4-cyclopropylphenyl)-1-methyl-1H-pyrazol-4-yl]-1-methyl-1H-pyrazolo[3,4-d]pyrimidine | 2.973 min⁵; 518 |
| 30 | Method A | pyrrolidin-1-yl | 4-cyclopropylphenyl | 3-[5-(4-cyclopropylphenyl)-1-methyl-1H-pyrazol-4-yl]-1-methyl-4-(pyrrolidin-1-yl)-1H-pyrazolo[3,4-d]pyrimidine | 2.453 min⁷; 400 |

TABLE 1-continued

Examples 7-60

| Example Number | Method | R² | R⁵ | Compound Name | ¹H NMR (400 MHz, CDCl₃), δ (ppm); Mass spectrum, observed ion m/z (M + 1) or HPLC retention time (minutes); Mass spectrum m/z (M + 1) (unless otherwise indicated) |
|---|---|---|---|---|---|
| 31 | Method A | (R)-3-acetamidopyrrolidin-1-yl | 4-cyclopropylphenyl | N-[(3R)-1-{3-[5-(4-cyclopropylphenyl)-1-methyl-1H-pyrazol-4-yl]-1-methyl-1H-pyrazolo[3,4-d]pyrimidin-4-yl}pyrrolidin-3-yl]acetamide | 2.305 min⁷; 457 |
| 32 | Ex 1³ | 3-(1-methyl-1H-pyrazol-3-yl)azetidin-1-yl | 4-cyclopropylphenyl | 3-[5-(4-cyclopropylphenyl)-1-methyl-1H-pyrazol-4-yl]-1-methyl-4-[3-(1-methyl-1H-pyrazol-3-yl)azetidin-1-yl]-1H-pyrazolo[3,4-d]pyrimidine | (characteristic peaks) 0.67-0.72 (m, 2H), 0.96-1.02 (m, 2H), 1.83-1.91 (m, 1H), 3.86 (s, 3H), 3.87 (s, 3H), 4.01 (s, 3H), 6.10 (d, J = 2.2 Hz, 1H), 7.02 (br d, J = 8.1 Hz, 2H), 7.23 (br d, J = 8.4 Hz, 2H), 7.30 (d, J = 2.2 Hz, 1H), 7.67 (s, 1H), 8.35 (s, 1H); 466.7 |
| 33 | Ex 1 | azetidin-1-yl | 4-cyclopropylphenyl | 4-(azetidin-1-yl)-3-[5-(4-cyclopropylphenyl)-1-methyl-1H-pyrazol-4-yl]-1-methyl-1H-pyrazolo[3,4-d]pyrimidine | (characteristic peaks) 0.66-0.71 (m, 2H), 0.94-1.00 (m, 2H), 1.82-1.90 (m, 1H), 2.20-2.29 (m, 2H), 3.89 (s, 3H), 3.99 (s, 3H), 7.03 (br d, J = 8.2 Hz, 2H), 7.23 (br d, J = 8.4 Hz, 2H), 7.65 (s, 1H), 8.31 (s, 1H); 386.1 |
| 34 | Ex 1¹ | azetidin-1-yl | 3-fluoro-4-methoxyphenyl | 4-(azetidin-1-yl)-3-[5-(3-fluoro-4-methoxyphenyl)-1-methyl-7H-pyrazol-4-yl]-1-methyl-1H-pyrazolo[3,4-d]pyrimidine | 2.23-2.32 (m, 2H), 3.76-4.04 (br m, 4H), 3.89 (s, 3H), 3.92 (s, 3H), 4.01 (s, 3H), 6.93 (dd, J = 8.6, 8.6 Hz, 1H), 7.08 (ddd, J = 8.4, 2.2, 1.3 Hz, 1H), 7.14 (dd, J = 11.8, 2.2 Hz, 1H), 7.67 (s, 1H), 8.34 (s, 1H); 394.1 |
| 35 | Ex 1 | azetidin-1-yl | 4-(trifluoromethyl)phenyl | 4-(azetidin-1-yl)-1-methyl-3-{1-methyl-5-[4-(trifluoromethyl)phenyl]-1H-pyrazol-4-yl}-1H-pyrazolo[3,4-d]pyrimidine | 2.22-2.31 (m, 2H), 3.78-4.03 (br m, 4H), 3.93 (s, 3H), 3.99 (s, 3H), 7.57 (br AB quartet, J_{AB} = 8.1 Hz, Δν_{AB} = 44 Hz, 4H), 7.70 (s, 1H), 8.33 (s, 1H); 414.4 |

TABLE 1-continued

Examples 7-60

|Example Number|Method|R²|R⁵|Compound Name|¹H NMR (400 MHz, CDCl₃), δ (ppm); Mass spectrum, observed ion m/z (M + 1) or HPLC retention time (minutes); Mass spectrum m/z (M + 1) (unless otherwise indicated)|
|---|---|---|---|---|---|
|36|Ex 1[8]|methylsulfonyl pyrrolidinyl (3S)|4-cyclopropylphenyl|3-[5-(4-cyclopropylphenyl)-1-methyl-1H-pyrazol-4-yl]-1-methyl-4-[(3S)-3-(methylsulfonyl)pyrrolidin-1-yl]-1H-pyrazolo[3,4-d]pyrimidine|0.65-0.70 (m, 2H), 0.95-1.01 (m, 2H), 1.81-1.89 (m, 1H), 2.24-2.36 (m, 2H), 2.83 (s, 3H), 3.45-3.74 (m, 5H), 3.91 (s, 3H), 4.06 (s, 3H), 7.01 (br d, J = 8.4 Hz, 2H), 7.25 (br d, J = 8.4 Hz, 2H), 7.68 (s, 1H), 8.31 (s, 1H); 478.6|
|37|Ex 4|azetidin-1-yl|5-cyclopropylpyridin-2-yl|4-(azetidin-1-yl)-3-[5-(5-cyclopropylpyridin-2-yl)-1-methyl-1H-pyrazol-4-yl]-1-methyl-1H-pyrazolo[3,4-d]pyrimidine|¹H NMR (400 MHz, CD₃OD) δ 0.70-0.75 (m, 2H), 1.01-1.07 (m, 2H), 1.90-1.98 (m, 1H), 2.18-2.27 (m, 2H), 3.74-3.96 (br m, 4H), 3.97 (s, 3H), 4.06 (s, 3H), 7.11 (d, J = 8.2 Hz, 1H), 7.26 (dd, J = 8.2, 2.3 Hz, 1H), 7.70 (s, 1H), 8.15 (s, 1H), 8.52 (d, J = 2.2 Hz, 1H); 387.2|
|38|Ex 1|3,3-difluoroazetidin-1-yl|4-(trifluoromethyl)phenyl|4-(3,3-difluoroazetidin-1-yl)-1-methyl-3-{1-methyl-5-[4-(trifluoromethyl)phenyl]-1H-pyrazol-4-yl}-1H-pyrazolo[3,4-d]pyrimidine|¹H NMR (400 MHz, CD₃OD) δ 3.97 (s, 3H), 3.99 (s, 3H), 4.20 (br dd, J = 12.3, 12.1, 4H), 7.66 (br AB quartet, J_{AB} = 8.2 Hz, Δv_{AB} = 35 Hz, 4H), 7.79 (s, 1H), 8.32 (s, 1H); 450.5|
|39|Ex 1|3-fluoroazetidin-1-yl|4-(trifluoromethyl)phenyl|4-(3-fluoroazetidin-1-yl)-1-methyl-3-{1-methyl-5-[4-(trifluoromethyl)phenyl]-1H-pyrazol-4-yl}-1H-pyrazolo[3,4-d]pyrimidine|¹H NMR (400 MHz, CD₃OD) δ 3.81-3.96 (br m, 2H), 3.96 (s, 3H), 3.97 (s, 3H), 4.11-4.27 (br m, 2H), 5.17-5.37 (m, 1H), 7.66 (br AB quartet, J_{AB} = 8.4 Hz, Δv_{AB} = 34 Hz, 4H), 7.78 (s, 1H), 8.24 (s, 1H); 432.4|
|40|Ex 1[1]|3-methoxyazetidin-1-yl|4-ethylphenyl|3-[5-(4-ethylphenyl)-1-methyl-1H-pyrazol-4-yl]-4-(3-methoxyazetidin-1-yl)-1-methyl-1H-pyrazolo[3,4-d]pyrimidine|1.19 (t, J = 7.6 Hz, 3H), 2.61 (q, J = 7.6 Hz, 2H), 3.22 (s, 3H), 3.64-3.83 (br m, 2H), 3.89 (s, 3H), 3.91-4.08 (br m, 2H), 3.98 (s, 3H), 4.08-4.14 (m, 1H), 7.19 (br AB quartet, J_{AB} = 8.2 Hz, Δv_{AB} = 34 Hz, 4H), 7.65 (s, 1H), 8.30 (s, 1H); 404.2|

TABLE 1-continued

Examples 7-60

| Example Number | Method | R² | R⁵ | Compound Name | ¹H NMR (400 MHz, CDCl₃), δ (ppm); Mass spectrum, observed ion m/z (M + 1) or HPLC retention time (minutes); Mass spectrum m/z (M + 1) (unless otherwise indicated) |
|---|---|---|---|---|---|
| 41 | Ex 1 | azetidin-1-yl | 4-bromophenyl | 4-(azetidin-1-yl)-3-[5-(4-bromophenyl)-1-methyl]-1H-pyrazol-4-yl]-1-methyl-1H-pyrazolo[3,4-d]pyrimidine | 2.21-2.31 (m, 2H), 3.76-4.00 (br m, 4H), 3.90 (s, 3H), 3.99 (s, 3H), 7.24 (br d, J = 8.2 Hz, 2H), 7.50 (br d, J = 8.4 Hz, 2H), 7.68 (s, 1H), 8.33 (s, 1H); 424.5 |
| 42 | Ex 1 | 3-methoxyazetidin-1-yl | 4-(trifluoromethyl)phenyl | 4-(3-methoxyazetidin-1-yl)-1-methyl-3-{1-methyl-5-[4-(trifluoromethyl)phenyl]-1H-pyrazol-4-yl}-1H-pyrazolo[3,4-d]pyrimidine | ¹H NMR (400 MHz, CD₃OD) δ 3.25 (s, 3H), 3.58-3.77 (br m, 2H), 3.95 (s, 3H), 3.95 (s, 3H), 3.97-4.13 (br m, 2H), 4.14-4.20 (m, 1H), 7.64 (br AB quartet, J_{AB} = 8.2 Hz, Δ_{AB} = 37 Hz, 4H), 7.77 (s, 1H), 8.18 (br s, 1H); 444.3 |
| 43 | Ex 1¹ | 3,3-difluoroazetidin-1-yl | 4-ethylphenyl | 4-(3,3-difluoroazetidin-1-yl)-3-[5-(4-ethylphenyl)-1-methyl-1H-pyrazol-4-yl]-1-methyl-1H-pyrazolo[3,4-d]pyrimidine | 1.22 (t, J = 7.6 Hz, 3H), 2.63 (q, J = 7.6 Hz, 2H), 3.94 (s, 3H), 4.04 (s, 3H), 4.13 (br dd, J = 12.1, 12.1 Hz, 4H), 7.21 (br AB quartet, J_{AB} = 8.3 Hz, Δν_{AB} = 25 Hz, 4H), 7.70 (s, 1H), 8.38 (s, 1H); 410.2 |
| 44 | Ex 2 | 3-methylazetidin-1-yl | 4-(trifluoromethyl)phenyl | 1-methyl-4-(3-methylazetidin-1-yl)-3-{1-methyl-5-[4-(trifluoromethyl)phenyl]-1H-pyrazol-4-yl}-1H-pyrazolo[3,4-d]pyrimidine | ¹H NMR (400 MHz, CD₃OD) δ 1.17 (d, J = 6.9 Hz, 3H), 2.65-2.78 (m, 1H), 3.34-3.54 (br m, 2H), 3.94 (s, 3H), 3.95 (s, 3H), 3.86-4.11 (br m, 2H), 7.65 (br AB quartet, J_{AB} = 8.2 Hz, Δν_{AB} = 39 Hz, 4H), 7.76 (s, 1H), 8.16 (s, 1H); 428.5 |
| 45 | Ex 1 | 3,3-difluoroazetidin-1-yl | 4-cyclopropylphenyl | 3-[5-(4-cyclopropylphenyl)-1-methyl-1H-pyrazol-4-yl]-4-(3,3-difluoroazetidin-1-yl)-1-methyl-1H-pyrazolo[3,4-d]pyrimidine | 0.66-0.71 (m, 2H), 0.95-1.01 (m, 2H), 1.82-1.90 (m, 1H), 3.93 (s, 3H), 4.04 (s, 3H), 4.09-4.18 (m, 4H), 7.03 (br d, J = 8.2 Hz, 2H), 7.21 (br d, J = 8.3 Hz, 2H), 7.69 (s, 1H), 8.38 (s, 1H); 422.6 |

TABLE 1-continued

Examples 7-60

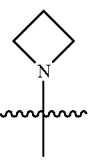 [SMILES: *N1CCC1]

| Example Number | Method | R² | R⁵ | Compound Name | ¹H NMR (400 MHz, CDCl₃), δ (ppm); Mass spectrum, observed ion m/z (M + 1) or HPLC retention time (minutes); Mass spectrum m/z (M + 1) (unless otherwise indicated) |
|---|---|---|---|---|---|
| 46 | Method B | 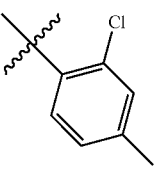 [SMILES: *c1ccc(C)cc1Cl] | 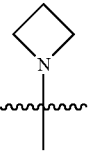 [SMILES: *N1CCC1] | 4-(azetidin-1-yl)-3-[5-(2-chloro-4-methylphenyl)-1-methyl-1H-pyrazol-4-yl]-1-methyl-1H-pyrazolo[3,4-d]pyrimidine | 2.729 min⁵; 394 |
| 47 | Method B | 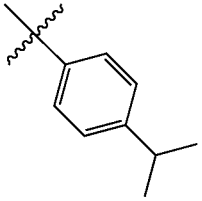 [SMILES: *c1ccc(C(C)C)cc1] | 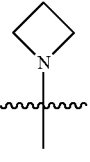 [SMILES: *N1CCC1] | 4-(azetidin-1-yl)-1-methyl-3-{1-methyl-5-[4-(propan-2-yl)phenyl]-1H-pyrazol-4-yl}-1H-pyrazolo[3,4-d]pyrimidine | 2.635 min⁵; 388 |
| 48 | Method B | 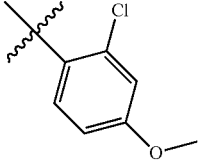 [SMILES: *c1ccc(OC)cc1Cl] | 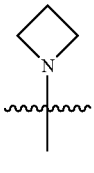 [SMILES: *N1CCC1] | 4-(azetidin-1-yl)-3-[5-(2-chloro-4-methoxyphenyl)-1-methyl-1H-pyrazol-4-yl]-1-methyl-1H-pyrazolo[3,4-d]pyrimidine | 2.492 min⁵; 410 |
| 49 | Method B | 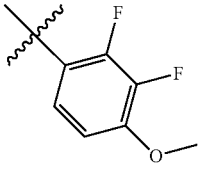 [SMILES: *c1ccc(OC)c(F)c1F] | 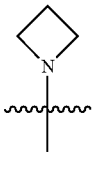 [SMILES: *N1CCC1] | 4-(azetidin-1-yl)-3-[5-(2,3-difluoro-4-methoxyphenyl)-1-methyl-1H-pyrazol-4-yl]-1-methyl-1H-pyrazolo[3,4-d]pyrimidine | 2.444 min⁵; 412 |
| 50 | Method B | 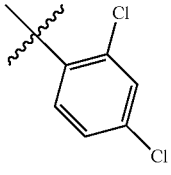 [SMILES: *c1ccc(Cl)cc1Cl] | 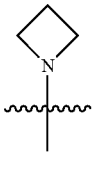 [SMILES: *N1CCC1] | 4-(azetidin-1-yl)-3-[5-(2,4-dichlorophenyl)-1-methyl-1H-pyrazol-4-yl]-1-methyl-1H-pyrazolo[3,4-d]pyrimidine | 2.65 min⁵; 414 |
| 51 | Method B | 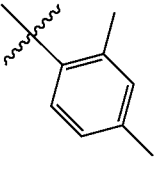 [SMILES: *c1ccc(C)cc1C] | | 4-(azetidin-1-yl)-3-[5-(2,4-dimethylphenyl)-1-methyl-1H-pyrazol-4-yl]-1-methyl-1H-pyrazolo[3,4-d]pyrimidine | 2.551 min⁵; 374 |

TABLE 1-continued

Examples 7-60

| Example Number | Method | R² | R⁵ | Compound Name | ¹H NMR (400 MHz, CDCl₃), δ (ppm); Mass spectrum, observed ion m/z (M + 1) or HPLC retention time (minutes); Mass spectrum m/z (M + 1) (unless otherwise indicated) |
|---|---|---|---|---|---|
| 52 | Ex 1¹ | N,N-dimethylamino | 4-cyclopropylphenyl | 3-[5-(4-cyclopropylphenyl)-1-methyl-1H-pyrazol-4-yl]-N,N,1-trimethyl-1H-pyrazolo[3,4-d]pyrimidin-4-amine | 0.62-0.68 (m, 2H), 0.92-0.99 (m, 2H), 1.80-1.88 (m, 1H), 2.81 (s, 6H), 3.88 (s, 3H), 4.00 (s, 3H), 7.04 (br AB quartet, J$_{AB}$ = 8.2 Hz, Δv$_{AB}$ = 53 Hz, 4H), 7.71 (s, 1H), 8.26 (s, 1H); 374.6 |
| 53 | Ex 5 | N,N-dimethylamino | 4-(trifluoromethyl)phenyl | N,N,1-trimethyl-3-{1-methyl-5-[4-(trifluoromethyl)phenyl]-1H-pyrazol-4-yl}-1H-pyrazolo[3,4-d]pyrimidin-4-amine | ¹H NMR (400 MHz, CD₃OD) δ 2.81 (s, 6H), 3.95 (s, 3H), 3.98 (s, 3H), 7.50 (br d, J = 8.1 Hz, 2H), 7.66 (br d, J = 8.1 Hz, 2H), 7.79 (s, 1H), 8.15 (s, 1H); 402.5 |
| 54 | Ex 6 | 3-fluoroazetidin-1-yl | 4-(difluoromethyl)phenyl | 3-{5-[4-(difluoromethyl)phenyl]-1-methyl-1H-pyrazol-4-yl}-4-(3-fluoroazetidin-1-yl)-1-methyl-1H-pyrazolo[3,4-d]pyrimidine | ¹H NMR (400 MHz, CD₃OD) δ 3.81-3.98 (br m, 2H), 3.95 (s, 3H), 3.97 (s, 3H), 4.11-4.26 (m, 2H), 5.17-5.37 (br m, 1H, J$_{HF}$ = 57 Hz), 6.75 (t, J$_{HF}$ = 56.0 Hz, 1H), 7.54 (br AB quartet, J$_{AB}$ = 8 Hz, Δv$_{AB}$ = 14 Hz, 4H), 7.76 (s, 1H), 8.23 (s, 1H); 414.5 |
| 55 | Ex 5⁹ | [²H₆]azetidin-1-yl | 4-(trifluoromethyl)phenyl | 4-([²H₆]azetidin-1-yl)-1-methyl-3-{1-methyl-5-[4-(trifluoromethyl)phenyl]-1H-pyrazol-4-yl}-1H-pyrazolo[3,4-d]pyrimidine | ¹H NMR (400 MHz, CD₃OD) δ 3.94 (br s, 6H), 7.65 (br AB quartet, J$_{AB}$ = 8.1 Hz, Δv$_{AB}$ =35 Hz, 4H), 7.75 (s, 1H), 8.16 (s, 1H); 420.6 |

TABLE 1-continued

Examples 7-60

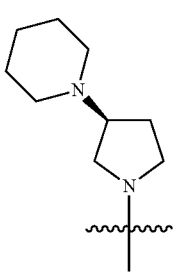 [SMILES: *N1CC[C@H](N2CCCCC2)C1]

| Example Number | Method | R² | R⁵ | Compound Name | ¹H NMR (400 MHz, CDCl₃), δ (ppm); Mass spectrum, observed ion m/z (M + 1) or HPLC retention time (minutes); Mass spectrum m/z (M + 1) (unless otherwise indicated) |
|---|---|---|---|---|---|
| 56 | Method A | 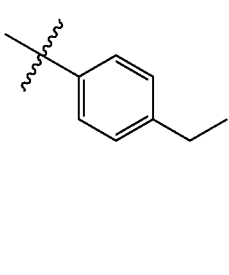 [SMILES: *c1ccc(CC)cc1] | 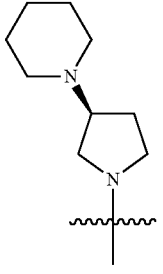 [SMILES: *N1CC[C@H](N2CCCCC2)C1] | 3-[5-(4-ethylphenyl)-1-methyl-1H-pyrazol-4-yl]-1-methyl-4-[(3S)-3-(piperidin-1-yl)pyrrolidin-1-yl]-1H-pyrazolo[3,4-d]pyrimidine | 0.66 min²; 471.45 |
| 57 | Ex 5¹⁰ | 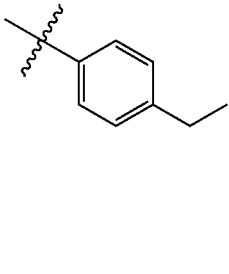 [SMILES: *c1ccc(CC)cc1] | 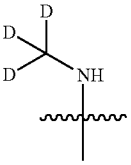 | 3-[5-(4-ethylphenyl)-1-methyl-1H-pyrazol-4-yl]-1-methyl-4-[(3S)-3-(piperidin-1-yl)pyrrolidin-1-yl]-1H-pyrazolo[3,4-d]pyrimidine, formate salt | 1.20 (t, J = 7.5 Hz, 3H), 1.51-1.63 (br m, 2H), 1.77-1.91 (br m, 4H), 2.15-2.32 (br m, 2H), 2.56-2.73 (br m, 4H), 2.78-2.96 (br m, 2H), 3.15-3.26 (br m, 1H), 3.31-3.47 (br m, 2H), 3.53-3.72 (br m, 2H), 3.94 (s, 3H), 4.04 (s, 3H), 7.14 (br d, J = 8 Hz, 2H), 7.23-7.28 (m, 2H, assumed; partially obscured by solvent peak), 7.69 (s, 1H), 8.30 (s, 1H), 8.32 (s, 1H); 471.3 |
| 58 | Ex 5 | 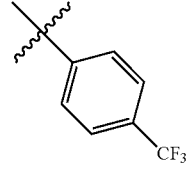 | 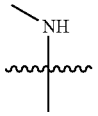 | 1-methyl-[²H₃]methyl-3-{1-methyl-5-[4-(trifluoromethyl)phenyl]-1H-pyrazol-4-yl}-1H-pyrazolo[3,4-d]pyrimidin-4-amine | ¹H NMR (400 MHz, CD₃OD) δ 3.94 (s, 3H), 3.95 (s, 3H), 7.56 (br d, J = 8.0 Hz, 2H), 7.70 (br d, J = 8.2 Hz, 2H), 7.79 (s, 1H), 8.20 (s, 1H); 391.2 |
| 59 | Ex 1¹ | 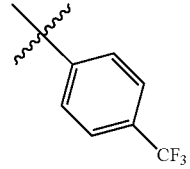 [SMILES: *c1ccc(C(F)(F)F)cc1] | 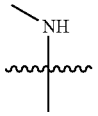 | N,1-dimethyl-3-{1-methyl-5-[4-(trifluoromethyl)phenyl]-1H-pyrazol-4-yl}-1H-pyrazolo[3,4-d]pyrimidin-4-amine | 3.00 (d, J = 4.9 Hz, 3H), 3.96 (s, 3H), 3.97 (s, 3H), 5.14-5.22 (br q, J = 5 Hz, 1H), 7.51-7.56 (m, 2H), 7.65-7.69 (m, 2H), 7.80 (s, 1H), 8.41 (br s, 1H); 388.1 |

TABLE 1-continued

Examples 7-60

| Example Number | Method | R² | R⁵ | Compound Name | ¹H NMR (400 MHz, CDCl₃), δ (ppm); Mass spectrum, observed ion m/z (M + 1) or HPLC retention time (minutes); Mass spectrum m/z (M + 1) (unless otherwise indicated) |
|---|---|---|---|---|---|
| 60 | Ex 1[1] | NH-azetidine (structure) | 4-(trifluoromethyl)phenyl (structure) | N-ethyl-1-methyl-3-{1-methyl-5-[4-(trifluoromethyl)phenyl]-1H-pyrazol-4-yl}-1H-pyrazolo[3,4-d]pyrimidin-4-amine | 1.17 (t, J = 7.2 Hz, 3H), 3.46-3.55 (m, 2H), 3.97 (s, 6H), 5.16-5.24 (m, 1H), 7.54 (br d, J = 8.0 Hz, 2H), 7.67 (br d, J = 8.2 Hz, 2H), 7.80 (s, 1H), 8.38 (br s, 1H); 402.1 |

[1]In this case, the final step was carried out under microwave conditions.
[2]HPLC conditions: Column: Agilent Prep-C18 scalar, 4.6 × 50 mm, 5 μm; Mobile phase A: 10 mM ammonium bicarbonate, pH 8.2; Mobile phase B: acetonitrile; Gradient: 0% to 100% B over 2.4 min (linear gradient); Flow rate: 3.75 mL/min.
[3]1-(tert-Butoxycarbonyl)azetidine-3-carboxylic acid was converted to tert-butyl 3-[(2E)-3-(dimethylamino)prop-2-enoyl]azetidine-1-carboxylate using chemistry similar to that described by A. B. Dounay et al., *Bioorg. Med. Chem. Lett.* 2009, 19, 1159-1163. Reaction with methylhydrazine provided the requisite pyrazole substituent, which was deprotected with trifluoroacetic acid to afford 3-(azetidin-3-yl)-1-methyl-1H-pyrazole.
[4]1-(Diphenylmethyl)azetidin-3-ol was converted to 1-(diphenylmethyl)azetidin-3-amine via a three-step procedure: mesylation was followed by displacement with sodium azide, and the resulting azide was reduced with triphenylphosphine. After carbamate formation with methyl chloroformate, deprotection via hydrogenation over palladium hydroxide provided the requisite methyl azetidin-3-ylcarbamate.
[5]HPLC conditions: Column: Welch XB-C18 2.1 × 50 mm, 5 μm; Mobile phase A: 0.0375% trifluoroacetic acid in water; Mobile phase B: 0.01875% trifluoroacetic acid in acetonitrile; Gradient: 1% to 5% B over 0.60 minutes, then 5% to 100% B over 3.40 minutes; Flow rate: 0.8 mL/min.
[6]tert-Butyl 3-[(2E)-3-(dimethylamino)prop-2-enoyl]azetidine-1-carboxylate (see footnote 3) was reacted with hydroxylamine to afford tert-butyl 3-(1,2-oxazol-5-yl)azetidine-1-carboxylate. Deprotection with trifluoroacetic acid gave the requisite 5-(azetidin-3-yl)-1,2-oxazole.
[7]HPLC conditions: Column: Welch XB-C18 2.1 × 50 mm, 5 μm; Mobile phase A: 0.0375% trifluoroacetic acid in water; Mobile phase B: 0.01875% trifluoroacetic acid in acetonitrile; Gradient: 10% B for 0.50 minutes, then 10% to 100% B over 3.50 minutes; Flow rate: 0.8 mL/min.
[8]The absolute stereochemistry was temporarily assigned.
[9]1-(Diphenylmethyl)(²H₅)azetidin-3-yl methanesulfonate was prepared from 2-[chloro(²H₂)methyl](²H₃)oxirane using the chemistry of M. E. Jung and Y. M. Choi, *J. Org. Chem.* 1991, 56, 6729-6730. Displacement of the methanesulfonate moiety was effected via treatment with sodium borodeuteride in N,N-dimethylformamide at elevated temperature, to afford 1-(diphenylmethyl)(²H₆)azetidine, which was deprotected to provide the requisite (2,2,3,3,4,4-²H₆)azetidine.
[10]This compound was obtained as the formate salt because the final purification was carried out using an HPLC gradient system composed of water and acetonitrile containing 0.225% formic acid.

Example AA

PDE2 Assays and Data

The compounds of Formula I (including compounds of any one of Formulae Ia, Ib, or Ic) are useful for modulating or inhibiting PDE2 activity. In some embodiments, compounds of the invention are selective modulators or inhibitors of PDE2 as compared to other PDE receptor subtypes. Accordingly, these compounds of the invention are useful for the prevention and/or treatment of a disease or condition of the central nervous system such as cognitive disorders, schizophrenia, and dementia in a mammal, preferably a human.

The term "inhibiting PDE 2", as used herein, means the prevention of, impediment of progression of, or therapeutically significant reduction in PDE2 activity. One of ordinary skill in the art is readily able to determine whether a compound inhibits PDE2 activity. For example, assays which may conveniently be used in order to assess the PDE2 inhibition may be found in U.S. Patent Application Publication No. 2006/0154931 (U.S. Ser. No. 11/326,221) published on Jul. 13, 2006. In general, a substance is considered to effectively inhibit PDE2 activity if it has an $IC_{50}$ of less than or about 10 μM, preferably less than or about 0.1 μM.

A "selective PDE2 inhibitor" can be identified, for example, by comparing the ability of a substance to inhibit PDE2 activity to its ability to inhibit PDE enzymes from the other PDE families. For example, a substance may be assayed for its ability to inhibit PDE2 activity, as well as PDE1A, PDE1B, PDE1C, PDE3A, PDE3B, PDE4A, PDE4B, PDE4C, PDE4D, PDE5, PDE6, PDE7, PDE8, PDE9, PDE10 and PDE11 activities. In one embodiment, a selective PDE2 inhibitor is a compound of the invention having a $K_i$ for inhibition of PDE2 that is less than or about one-tenth the $K_i$ that the substance has for inhibition of any other PDE enzyme, i.e., the compound inhibits PDE2 activity to the same degree at a concentration of about one-tenth or less than the concentration required for inhibition of any other PDE enzyme.

Measurement of Recombinant Human PDE2A3 Inhibition by SPA Technology

In the present assay, the activity of the test substances on human full-length PDE2A3 enzyme was determined using the [³H]-cGMP scintillation proximity assay (SPA) modified from the Amersham TRKQ7100 instructions (GE Healthcare, Arlington Heights, Ill., USA). PDE2A3 protein was obtained from FLAG purification of sf21 insect cells using standard affinity purification procedures for this tag (anti- FLAG M2, Sigma Aldrich, St. Louis, Mo., USA). Briefly, the SPA assays were performed using PDE SPA yttrium silicate beads (Perkin Elmer RPNQ0024; PerkinElmer, Inc., Waltham, Mass., USA) which bind preferentially to the linear nucleotide, GMP, compared to the cyclic nucleotide, cGMP. The, $^3$H-GMP product was detected using a Wallac Micro-Beta scintillation counter. The reaction time was chosen with respect to the amount of time in which 10-20% of substrate was hydrolyzed by the enzyme.

The assay was validated using PDE2-selective literature compounds, erythro-9-(2-hydroxy-3-nonyl) adenine (EHNA) and BAY 60-7550 as controls before testing the representative compounds of the present invention (Podzuweit et al., *Isozyme selective inhibition of cGMP-stimulated cyclic nucleotide phosphodiesterases by erythro-9-(2-hydroxy-3-nonyl)adenine*, Cell Signal, 7(7):733-8, 1995, Boess et al., *Inhibition of phosphodiesterase 2 increases neuronal cGMP, synaptic plasticity and memory performance*, Neuropharmacology, 47(7):1081-92, 2004). The $IC_{50}$ values obtained were within 3× of literature values, 1.7 µM for EHNA and 4.66 µM for BAY 60-7550. The corresponding $IC_{50}$ values of the compounds for the inhibition of PDE activities are determined from the concentration-effect curves by means of non-linear regression.

TABLE 2

| Example Number | PDE2A3 $IC_{50}$ (nM) or % inhibition; Geometric mean of 2-5 determinations, unless otherwise indicated |
|---|---|
| Example 1 | <6.79 |
| Example 2 | 31% inhibition at 316 nM[a] |
| Example 3 | <1.31 |
| Example 4 | 9.54 |
| Example 5 | 131[a] |
| Example 6 | 5.25 |
| Example 7 | <5.84 |
| Example 8 | 3.16 |
| Example 9 | 1.64[b] |
| Example 10 | 6.33 |
| Example 11 | 4.29 |
| Example 12 | 7.08 |
| Example 13 | 3.10 |
| Example 14 | 4.47 |
| Example 15 | 9.89 |
| Example 16 | 9.87 |
| Example 17 | 5.48 |
| Example 18 | 9.34 |
| Example 19 | <2.87 |
| Example 20 | 3.59 |
| Example 21 | 9.47 |
| Example 22 | 9.89 |
| Example 23 | <2.11 |
| Example 24 | 5.37 |
| Example 25 | 2.70 |
| Example 26 | 5.14 |
| Example 27 | 2.98 |
| Example 28 | 4.25 |
| Example 29 | 2.47 |
| Example 30 | 5.63 |
| Example 31 | 1.52 |
| Example 32 | 2.58 |
| Example 33 | 3.41 |
| Example 34 | <8.44 |
| Example 35 | 1.67[b] |
| Example 36 | 1.43[b] |
| Example 37 | 8.93 |
| Example 38 | 5.55 |
| Example 39 | 6.44 |
| Example 40 | 3.50 |
| Example 41 | 4.20 |
| Example 42 | 8.60 |
| Example 43 | 7.43 |
| Example 44 | 6.83 |

TABLE 2-continued

| Example Number | PDE2A3 $IC_{50}$ (nM) or % inhibition; Geometric mean of 2-5 determinations, unless otherwise indicated |
|---|---|
| Example 45 | 5.89 |
| Example 46 | 6.27 |
| Example 47 | 2.16 |
| Example 48 | 5.39 |
| Example 49 | 9.01[a] |
| Example 50 | 9.72 |
| Example 51 | 7.23 |
| Example 52 | 4.36 |
| Example 53 | 1.06[a] |
| Example 54 | 7.95[a] |
| Example 55 | 1.48 |
| Example 56 | 41% inhibition at 316 nM[a] |
| Example 57 | N.D.[c] |
| Example 58 | 27.0 |
| Example 59 | 13.7 |
| Example 60 | 126 |

[a]Single determination
[b]Geometric mean of 7-8 determinations
[c]Not determined Example BB CYP3A Assay and Data Validated CYP3A assays such as those described in Walsky and Obach, "Validated Assays For Human Cytochrome P450 Activities," *Drug Metabolism And Disposition*, Vol. 32, No 6, pp 647-660, 2004, can be used to measure CYP3A4 $IC_{50}$ and CYP3A5 $IC_{50}$ of compounds of Formula Id. A practical method for utilizing compounds of Formula Id for chemical inhibition phenotyping, a two-step time-dependent inactivation kinetic assessment was made. Due to the ability of compounds of Formula Id to inactivate CYP3A4 to the $IC_{85}$ in a short time period, an additional non-undilution method (see below) was also available for compounds which have low clearance, but require an assessment of CYP3A5 contribution to their metabolism. The time dependent experiment consisted of three legs, one with a compound of Formula Id, and a vehicle control to establish an activity benchmark, and finally one using ketoconazole [CAS number: 65277-42-1; chemical name: 1-[4-(4-{[(2R,4S)-2-(2,4-dichlorophenyl)-2-(1H-imidazol-1-ylmethyl)-1,3-dioxolan-4-yl]methoxy}phenyl)piperazin-1-yl]ethan-1-one] as a competitive pan-CYP3A inhibitor. For the compound of Formula Id and vehicle legs, the first step of the assessment consisted of the inactivation reaction, wherein human liver microsomes from single donor genotyped for CYP3A5 (i.e CYP3A5 *1/*1, *1/*3, *3/*3) or liver microsomes pooled from multiple individual donors were added to the compound of Formula Id or vehicle. After 5 minutes of preincubation at 37° C. to allow for equilibrium, the inactivation reaction was initiated with 0.01 mL of 10 mM NADPH regeneration system (final concentration: 5 mM glucose-6-phosphate, 1 mM NADP+, and 1 U/mL glucose-6-phosphate dehydrogenase in 100 mM potassium phosphate buffer, in the presence of 1 mM $MgCl_2$; or 1 mM NADPH) was delivered to the compound of Formula Id and the vehicle control legs. After 5 minutes of incubation, an aliquot from the inactivation or vehicle control reaction was taken and added to a CYP3A substrate for measurement of activity. To establish a baseline CYP3A contribution for a test compound, ketoconazole was utilized as a competitive pan-inhibitor. This was then compared to the CYP3A4 specific inhibitor results with the difference presumed to be the remaining unaffected CYP3A5 activity. A similar method was also used to test the ability of a compound of Formula Id with low clearance test compounds in an undiluted inactivation reaction. In the ketoconzole study, 100 μM ketoconazole was introduced to liver microsomes of CYP3A5 genotyped single donor HLMs and CYP3A substrate, after a 5 minute preincubation, NADPH regeneration system or NADPH was added to initiate the reaction. The activity was measured by monitoring the consumption of the CYP3A substrate and/or generation of its metabolite(s)

TABLE 3

| Example Number | CYP3A4 $IC_{50}$ (μM); Midazolam | CYP3A5 $IC_{50}$ (μM); Midazolam | Fold selectivity |
|---|---|---|---|
| 2 | 0.06532 | 9.692 | 148 |
| 56 | 0.03972 | 3.468 | 87 |

TABLE 4

| Example Number | CYP3A4 $IC_{50}$ (μM); Testoterone | CYP3A5 $IC_{50}$ (μM); Testoterone | Fold selectivity |
|---|---|---|---|
| 2 | 0.1222 | 0.93 | 172 |
| 56 | 0.07106 | 6.965 | 98 |

Various modifications of the invention, in addition to those described herein, will be apparent to those skilled in the art from the foregoing description. Such modifications are also intended to fall within the scope of the appendant claims. Each reference (including all patents, patent applications, journal articles, books, and any other publications) cited in the present application is herein incorporated by reference in its entirety.

What is claimed is:
1. A compound of Formula I:

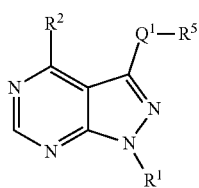

or a pharmaceutically acceptable salt thereof, wherein:
"-$Q^1$-$R^5$" is $Q^{1a}R^5$, $Q^{1b}R^5$, or $Q^{1c}R^5$:

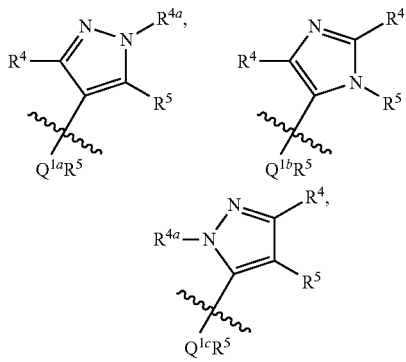

$R^1$ is hydrogen, $(C_1$-$C_6)$alkyl, $(C_3$-$C_4)$alkenyl, $(C_3$-$C_4)$alkynyl, —$CF_3$, —$CHF_2$, —$CH_2F$, or $(C_3$-$C_{15})$cycloalkyl;
$R^2$ is —$NHR^3$ or —$N(R^3)_2$;
each $R^3$ is independently selected from the group consisting of $(C_1$-$C_6)$alkyl, $(C_1$-$C_6)$haloalkyl, $(C_2$-$C_6)$alkenyl, $(C_2$-$C_6)$alkynyl, and $(C_3$-$C_{15})$cycloalkyl, each optionally substituted with 1, 2, 3, 4, or 5 independently selected $R^9$;
or when $R^2$ is —$N(R^3)_2$ both of said $R^3$ may be taken together with the nitrogen atom to which they are attached to form a 4- to 6-membered heterocyclic ring optionally containing one or two oxo groups (O=) and optionally substituted with one to three substituents each independently selected from the group consisting of fluoro, chloro, bromo, —CN, —$CF_3$, —$CHF_2$, —$CH_2F$, —OH, —O—$(C_1$-$C_6)$alkyl, $NH_2$, —NH—$(C_1$-$C_6)$alkyl, —N$[(C_1$-$C_6)$alkyl$]_2$, $(C_1$-$C_6)$alkyl, $(C_2$-$C_6)$alkenyl, $(C_2$-$C_6)$alkynyl, —(C=O)—$R^8$, —(C=O)—$OR^8$, —(C=O)—$N(R^8)_2$, —O—(C=O)—$R^8$, —$OR^8$, —O—(C=O)—$OR^8$, —$SR^8$, —$S(O)R^8$, —$S(O)_2R^8$, —$S(O)_2N(R^8)_2$, —NH—(C=O)—$R^8$, —NH—(C=O)—$OR^8$, —O—(C=O)—$N(R^8)_2$, —NH—(C=O)—$N(R^8)_2$, —N$[(C_1$-$C_6)$alkyl](C=O)—$R^8$, —N$[(C_1$-$C_6)$alkyl](C=O)—$OR^8$, —N$[(C_1$-$C_6)$alkyl](C=O)—$N(R^8)_2$, $(C_3$-$C_{15})$cycloalkyl, $(C_6$-$C_{10})$aryl, $(C_1$-$C_{14})$heterocyclic, and $(C_1$-$C_{13})$heteroaryl; wherein each of said $(C_3$-$C_{15})$cycloalkyl and $(C_1$-$C_{14})$heterocyclic may optionally contain one double or triple bond and may optionally contain one to two oxo (O=) groups, and wherein each of said $(C_3$-$C_{15})$cycloalkyl, $(C_6$-$C_{10})$aryl, $(C_1$-$C_{14})$heterocyclic, and $(C_1$-$C_{13})$heteroaryl is optionally substituted with one to three substituents each independently selected from fluoro, chloro, bromo, —CN, —$CF_3$, —$CHF_2$, —$CH_2F$, —OH, —O—$(C_1$-$C_6)$alkyl, —O—$(C_1$-$C_6)$haloalkyl, $NH_2$, —NH—$(C_1$-$C_6)$alkyl, —N$[(C_1$-$C_6)$alkyl$]_2$, $(C_1$-$C_6)$alkyl, $(C_1$-$C_6)$haloalkyl, $(C_2$-$C_6)$alkenyl, and $(C_2$-$C_6)$alkynyl;
each $R^4$ is independently selected from the group consisting of hydrogen, halo, $(C_1$-$C_6)$alkyl, $(C_2$-$C_6)$alkenyl, $(C_2$-$C_6)$alkynyl, —$CF_3$, —$CHF_2$, —$CH_2F$, and $(C_3$-$C_{15})$cycloalkyl;
$R^{4a}$ is hydrogen, $(C_1$-$C_6)$alkyl, $(C_3$-$C_4)$alkenyl, $(C_3$-$C_4)$alkynyl, —$CF_3$, —$CHF_2$, —$CH_2F$, or $(C_3$-$C_{15})$cycloalkyl;
$R^5$ is $R^{5a}$, $R^{5b}$, $R^{5c}$, $R^{5d}$, $R^{5e}$, $R^{5f}$, or $R^{5g}$:

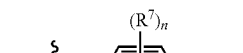

R5a

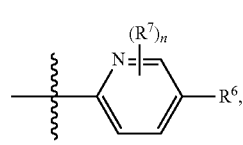

R5b

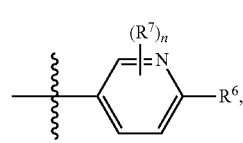

R5c

-continued

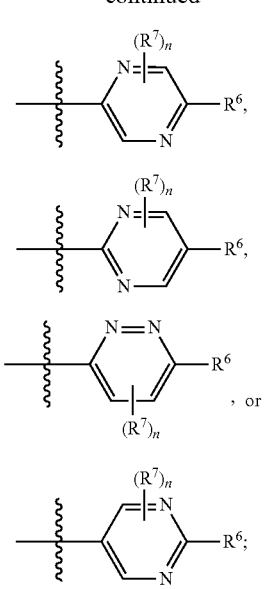

where n is 0, 1, 2, 3, or 4;

$R^6$ is selected from the group consisting of hydrogen, halo, $(C_1-C_6)$alkyl, —$CF_3$, —$CHF_2$, —$CH_2F$, —$CF_2$—$(C_1-C_6)$alkyl, —$SF_5$, —CN, —$(C_1-C_6)$alkyl-CN, —$NO_2$, —(C═O)—$R^8$, —(C═O)—$OR^8$, —$OR^8$, —O—(C═O)—$N(R^8)_2$, —$SR^8$, —$S(O)R^8$, —$S(O)_2R^8$, $NH_2$, —NH—$(C_1-C_6)$alkyl, —$N[(C_1-C_6)$alkyl$]_2$, —NH—(C═O)—$R^8$, —NH—(C═O)—$OR^8$, —$N[(C_1-C_6)$alkyl](C═O)—$R^8$, —$N[(C_1-C_6)$alkyl](C═O)—$OR^8$, $(C_2-C_6)$alkenyl, $(C_2-C_6)$alkynyl, $(C_3-C_{15})$cycloalkyl, $(C_1-C_{14})$heterocyclic, $(C_6-C_{10})$aryl, and $(C_1-C_{13})$heteroaryl; wherein each of said $(C_3-C_{15})$cycloalkyl and $(C_1-C_{14})$heterocyclic optionally contains one double or triple bond and optionally contains one to two oxo (O═) groups;

each $R^7$ is independently selected from the group consisting of halo, $(C_1-C_6)$alkyl, $(C_2-C_6)$alkenyl, $(C_2-C_6)$alkynyl, —CN, —$CF_3$, —$CHF_2$, —$CH_2F$, —O—$(C_1-C_6)$alkyl and $(C_3-C_{15})$cycloalkyl;

or $R^6$ and an adjacent $R^7$, together with the two carbon atoms to which they are attached, form a 5- or 6-membered heteroaryl or a 5- or 6-membered heterocyclic ring, each optionally substituted with one to three substituents each independently selected from fluoro, chloro, bromo, —CN, —$CF_3$, —$CHF_2$, —$CH_2F$, —OH, —O—$(C_1-C_6)$alkyl, —O—$(C_1-C_6)$haloalkyl, $(C_1-C_6)$alkyl, and $(C_1-C_6)$haloalkyl;

or two adjacent $R^7$, together with the two carbon atoms to which they are attached, form a 5- or 6-membered heteroaryl or a 5- or 6-membered heterocyclic ring, each optionally substituted with one to three substituents each independently selected from fluoro, chloro, bromo, —CN, —$CF_3$, —$CHF_2$, —$CH_2F$, —OH, —O—$(C_1-C_6)$alkyl, —O—$(C_1-C_6)$haloalkyl, $(C_1-C_6)$alkyl, and $(C_1-C_6)$haloalkyl;

each $R^8$ wherever it occurs is independently selected from the group consisting of hydrogen, $(C_1-C_6)$alkyl, $(C_3-C_{15})$cycloalkyl, —$(C_1-C_6)$alkyl-$(C_3-C_{15})$cycloalkyl, —$CF_3$, —$CH_2F$, and —$CHF_2$; and each $R^9$ is independently selected from the group consisting of halo, —$CF_3$, —$CHF_2$, —$CH_2F$, —$CF_2$—$(C_1-C_6)$alkyl, —CN, —$(C_1-C_6)$alkyl-CN, —$NO_2$, —(C═O)—$R^8$, —(C═O)—$OR^8$, —$OR^8$, —O—(C═O)—$N(R^8)_2$, —$SR^8$, —$S(O)R^8$, —$S(O)_2R^8$, $NH_2$, —NH—$(C_1-C_6)$alkyl, —$N[(C_1-C_6)$alkyl$]_2$, —NH—(C═O)—$R^8$, —NH—(C═O)—$OR^8$, —$N[(C_1-C_6)$alkyl](C═O)—$R^8$, —$N[(C_1-C_6)$alkyl](C═O)—$OR^8$, $(C_1-C_6)$alkyl, $(C_2-C_6)$alkenyl, $(C_2-C_6)$alkynyl, $(C_3-C_{15})$cycloalkyl, $(C_1-C_{14})$heterocyclic, $(C_6-C_{10})$aryl, and $(C_1-C_{13})$heteroaryl; wherein each of said $(C_3-C_{15})$cycloalkyl and $(C_1-C_{14})$heterocyclic may optionally contain one double or triple bond and one to two oxo (O═) groups; and wherein each of said $(C_3-C_{15})$cycloalkyl, $(C_1-C_{14})$heterocyclic, $(C_6-C_{10})$aryl, and $(C_1-C_{13})$heteroaryl moieties may be optionally substituted with one to three substituents independently selected from $(C_1-C_6)$alkyl, $(C_1-C_6)$alkoxy, halo, and —$CF_3$.

2. A compound according to claim 1, or a pharmaceutically acceptable salt thereof, wherein the compound is a compound of Formula Ia:

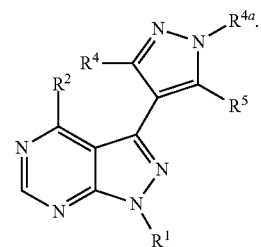

3. A compound according to claim 1, or a pharmaceutically acceptable salt thereof, wherein the compound is a compound of Formula Ib or Ic:

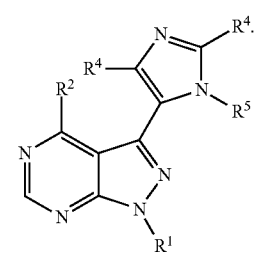

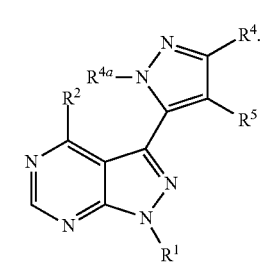

4. A compound according to claim 1, or a pharmaceutically acceptable salt thereof, wherein $R^1$ is $(C_1-C_6)$alkyl.

5. A compound according to claim 1, or a pharmaceutically acceptable salt thereof, wherein $R^1$ is methyl.

6. A compound according to claim 1, or a pharmaceutically acceptable salt thereof, wherein:

R² is —N(R³)₂;

each R³ is independently selected from (C₁-C₆)alkyl;

or both of said R³ may be taken together with the nitrogen atom to which they are attached to form a 4- to 6-membered heterocyclic ring optionally containing one or two oxo groups (O=) and optionally substituted with one to three substituents each independently selected from the group consisting of fluoro, chloro, bromo, —CN, —CF₃, —CHF₂, —CH₂F, —OH, —O—(C₁-C₆)alkyl, NH₂, —NH—(C₁-C₆)alkyl, —N[(C₁-C₆)alkyl]₂, (C₁-C₆)alkyl, (C₂-C₆)alkenyl, (C₂-C₆)alkynyl, —(C=O)—R⁸, —(C=O)—OR⁸, —(C=O)—N(R⁸)₂, —O—(C=O)—R⁸, —OR⁸, —O—(C=O)—OR⁸, —SR⁸, —S(O)R⁸, —S(O)₂R⁸, —S(O)₂N(R⁸)₂, —NH—(C=O)—R⁸, —NH—(C=O)—OR⁸, —O—(C=O)—N(R⁸)₂, —NH—(C=O)—N(R⁸)₂, —N[(C₁-C₆)alkyl](C=O)—R⁸, —N[(C₁-C₆)alkyl](C=O)—OR⁸, —N[(C₁-C₆)alkyl](C=O)—N(R⁸)₂, (C₃-C₁₅)cycloalkyl, (C₆-C₁₀)aryl, (C₁-C₁₄)heterocyclic, and (C₁-C₁₃)heteroaryl; wherein each of said (C₃-C₁₅)cycloalkyl and (C₁-C₁₄)heterocyclic may optionally contain one double or triple bond and may optionally contain one to two oxo (O=) groups, and wherein each of said (C₃-C₁₅)cycloalkyl, (C₆-C₁₀)aryl, (C₁-C₁₄)heterocyclic, and (C₁-C₁₃)heteroaryl is optionally substituted with one to three substituents each independently selected from fluoro, chloro, bromo, —CN, —CF₃, —CHF₂, —CH₂F, —OH, —O—(C₁-C₆)alkyl, —O—(C₁-C₆)haloalkyl, NH₂, —NH—(C₁-C₆)alkyl, —N[(C₁-C₆)alkyl]₂, (C₁-C₆)alkyl, (C₁-C₆)haloalkyl, (C₂-C₆)alkenyl, and (C₂-C₆)alkynyl.

7. A compound according to claim 1, or a pharmaceutically acceptable salt thereof, wherein R² is —N(R³)₂; and both of said R³ may be taken together with the nitrogen atom to which they are attached to form an azetidinyl, pyrrolidinyl, or piperidinyl ring, each optionally substituted with one to three substituents each independently selected from the group consisting of fluoro, —CN, —O—(C₁-C₆)alkyl, —N[(C₁-C₆)alkyl]₂, (C₁-C₆)alkyl, —S(O)₂R⁸, —S(O)₂N(R⁸)₂, —NH—(C=O)—R⁸, —NH—(C=O)—OR⁸, —N[(C₁-C₆)alkyl](C=O)—R⁸, (C₁-C₁₄)heterocyclic, and (C₁-C₁₃)heteroaryl; and wherein each of said (C₁-C₁₄)heterocyclic, and (C₁-C₁₃)heteroaryl is optionally substituted with one to three substituents each independently selected from (C₁-C₆)alkyl; and each R⁸ wherever it occurs is independently selected from the group consisting of (C₁-C₆)alkyl and —(C₁-C₆)alkyl-(C₃-C₁₅)cycloalkyl.

8. A compound according to claim 1, or a pharmaceutical acceptable salt thereof, wherein each R⁴ is hydrogen and R⁴ᵃ is (C₁-C₆)alkyl.

9. A compound according to claim 1, or a pharmaceutically acceptable salt thereof, wherein R⁵ is R⁵ᵃ:

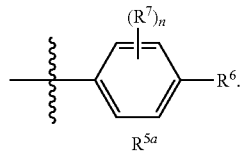

10. A compound according to claim 9, or a pharmaceutically acceptable salt thereof, wherein:

R⁶ is selected from the group consisting of hydrogen, halo, (C₁-C₆)alkyl, —CF₃, —CHF₂, —CH₂F, —CF₂—(C₁-C₆)alkyl, —SF₅, —CN, —(C₁-C₆)alkyl-CN, —NO₂, —(C=O)—R⁸, —(C=O)—OR⁸, —O—(C=O)—N(R⁸)₂, —S(O)R⁸, —S(O)₂R⁸, NH₂, —NH—(C₁-C₆)alkyl, —N[(C₁-C₆)alkyl]₂, —NH—(C=O)—R⁸, —NH—(C=O)—OR⁸, —N[(C₁-C₆)alkyl](C=O)—R⁸, —N[(C₁-C₆)alkyl](C=O)—OR⁸, (C₂-C₆)alkenyl, (C₂-C₆)alkynyl, (C₃-C₁₅)cycloalkyl, (C₁-C₁₄)heterocyclic, (C₆-C₁₀)aryl, and (C₁-C₁₃)heteroaryl; wherein each of said (C₃-C₁₅)cycloalkyl and (C₁-C₁₄)heterocyclic optionally contains one double or triple bond and optionally contains one to two oxo (O=) groups; and each R⁷ is independently selected from the group consisting of halo, (C₁-C₆)alkyl, (C₂-C₄)alkenyl, (C₂-C₆)alkynyl, —CN, —CF₃, —CHF₂, —CH₂F, —O—(C₁-C₆)alkyl and (C₃-C₁₅)cycloalkyl.

11. A compound according to claim 10, or a pharmaceutically acceptable salt thereof, wherein R⁶ is halo, (C₁-C₆)alkyl, —CF₃, —CHF₂, —OR⁸, or (C₃-C₁₅)cycloalkyl.

12. A compound according to claim 11, or a pharmaceutically acceptable salt thereof, wherein each R⁷ is independently selected from the group consisting of halo and (C₁-C₆)alkyl; and n is 0, 1, or 2.

13. A compound according to claim 1, or a pharmaceutically acceptable salt thereof, wherein:

"-Q¹-R⁵" is Q¹ᵃR⁵:

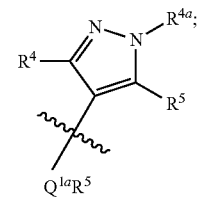

R¹ is (C₁-C₆)alkyl;

R² is —N(R³)₂ wherein both of said R³ are taken together with the nitrogen atom to which they are attached to form a 4- to 6-membered heterocyclic ring optionally containing one or two oxo groups (O=), and optionally may be substituted with one to three substituents each independently selected from the group consisting of fluoro, —CN, —CF₃, —CHF₂, —CH₂F, —OH, —O—(C₁-C₆)alkyl, NH₂, —NH—(C₁-C₆)alkyl, —N[(C₁-C₆)alkyl]₂, (C₁-C₆)alkyl, (C₂-C₆)alkenyl, (C₂-C₆)alkynyl, —(C=O)—R⁸, —(C=O)—OR⁸, —(C=O)—N(R⁸)₂—O—(C=O)—R⁸, —OR⁸, —O—(C=O)—OR⁸, —SR⁸, —S(O)R⁸, —S(O)₂R⁸, —S(O)₂N(R⁸)₂, —NH—(C=O)—R⁸, —NH—(C=O)—OR⁸, —O—(C=O)—N(R⁸)₂, —NH—(C=O)—N(R⁸)₂, —N[(C₁-C₆)alkyl](C=O)—R⁸, —N[(C₁-C₆)alkyl](C=O)—OR⁸, —N[(C₁-C₆)alkyl](C=O)—N(R⁸)₂, (C₃-C₁₅)cycloalkyl, (C₆-C₁₀)aryl, (C₁-C₁₄)heterocyclic, and (C₁-C₁₃)heteroaryl; wherein each of said (C₃-C₁₅)cycloalkyl and (C₁-C₁₄)heterocyclic optionally contains one double or triple bond and optionally contains one to two oxo (O=) groups, and wherein each of said (C₃-C₁₅)cycloalkyl, (C₆-C₁₀)aryl, (C₁-C₁₄)heterocyclic, and (C₁-C₁₃)heteroaryl is optionally substituted with one to three substituents each independently selected from fluoro, chloro, bromo, —CN, —CF₃, —CHF₂, CH₂F, —OH, —O—(C₁-C₆)alkyl, —O—(C₁-C₆)haloalkyl, NH₂, —NH—(C₁-C₆)alkyl, —N[(C₁-C₆)alkyl]₂, (C₁-C₆)alkyl, (C₁-C₆)haloalkyl, (C₂-C₆)alkenyl, and (C₂-C₆)alkynyl;

$R^4$ is hydrogen;
$R^{4a}$ is $(C_1-C_6)$alkyl; and
$R^5$ is $R^{5a}$, $R^{5b}$, $R^{5c}$, or $R^{5d}$:

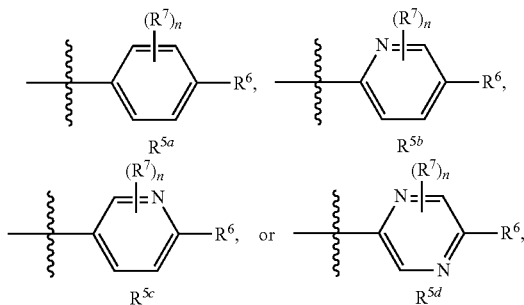

where n is 0, 1, 2, 3, or 4.

14. A compound of Formula Ia according to claim 2, or a pharmaceutically acceptable salt thereof, wherein:
$R^1$ is methyl, —$CF_3$, —$CHF_2$, or —$CH_2F$;
$R^2$ is —$N(R^3)_2$, wherein both of said $R^3$ are taken together with the nitrogen atom to which they are attached to form an optionally substituted 4- to 6-membered heterocyclic ring that is a moiety of

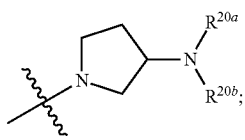

the "$Q^{1a}R^5$" moiety of

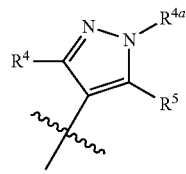

is a moiety of

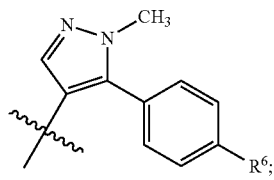

each of $R^{20a}$ and $R^{20b}$ is independently $(C_1-C_3)$alkyl;
or $R^{20a}$ and $R^{20b}$, together with the nitrogen atom to which they are attached, form a 5- or 6-membered heterocyclic ring; and
$R^6$ is methyl, ethyl, or Cl.

15. A compound of Formula Ia according to claim 2, or a pharmaceutically acceptable salt thereof, wherein the compound of Formula Ia or a pharmaceutically acceptable salt thereof is a compound of Formula Id:

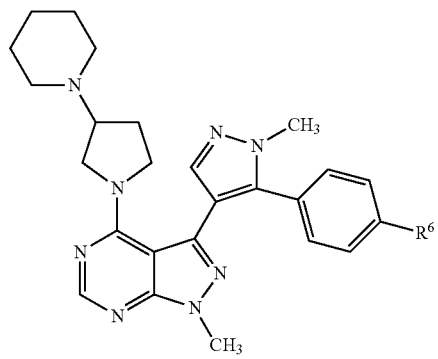

or a pharmaceutically acceptable salt thereof, wherein $R^6$ is methyl or ethyl.

16. A compound according to claim 1 wherein said compound is:
  4-(azetidin-1-yl)-1-methyl-3-[1-methyl-5-(4-methylphenyl)-1H-pyrazol-4-yl]-1H-pyrazolo[3,4-d]pyrimidine;
  3-[5-(4-cyclopropylphenyl)-1-methyl-1H-pyrazol-4-yl]-4-(3-fluoroazetidin-1-yl)-1-methyl-1H-pyrazolo[3,4-d]pyrimidine;
  4-(azetidin-1-yl)-1-methyl-3-{1-methyl-5-[5-(trifluoromethyl)pyridin-2-yl]-1H-pyrazol-4-yl}-1H-pyrazolo[3,4-d]pyrimidine;
  4-(azetidin-1-yl)-3-{5-[4-(difluoromethyl)phenyl]-1-methyl-1H-pyrazol-4-yl}-1-methyl-1 H-pyrazolo[3,4-d]pyrimidine;
  3-[5-(4-ethylphenyl)-1-methyl-1H-pyrazol-4-yl]-4-(3-fluoroazetidin-1-yl)-1-methyl-1H-pyrazolo[3,4-d]pyrimidine;
  4-(azetidin-1-yl)-3-[5-(4-ethylphenyl)-1-methyl-1H-pyrazol-4-yl]-1-methyl-1H-pyrazolo[3,4-d]pyrimidine;
  methyl (1-{3-[5-(4-cyclopropylphenyl)-1-methyl-1H-pyrazol-4-yl]-1-methyl-1H-pyrazolo[3,4-d]pyrimidin-4-yl}azetidin-3-yl)carbamate;
  4-(azetidin-1-yl)-3-[5-(4-cyclopropylphenyl)-1-methyl-1H-pyrazol-4-yl]-1-methyl-1H-pyrazolo[3,4-d]pyrimidine;
  4-(azetidin-1-yl)-3-[5-(3-fluoro-4-methoxyphenyl)-1-methyl-1H-pyrazol-4-yl]-1-methyl-1 H-pyrazolo[3,4-d]pyrimidine;
  4-(azetidin-1-yl)-1-methyl-3-{1-methyl-5-[4-(trifluoromethyl)phenyl]-1H-pyrazol-4-yl}-1 H-pyrazolo[3,4-d]pyrimidine;
  4-(3,3-difluoroazetidin-1-yl)-1-methyl-3-{1-methyl-5-[4-(trifluoromethyl)phenyl]-1H-pyrazol-4-yl}-1H-pyrazolo[3,4-d]pyrimidine;
  4-(3-fluoroazetidin-1-yl)-1-methyl-3-{1-methyl-5-[4-(trifluoromethyl)phenyl]-1H-pyrazol-4-yl}-1H-pyrazolo[3,4-d]pyrimidine;
  4-(azetidin-1-yl)-3-[5-(4-bromophenyl)-1-methyl-1H-pyrazol-4-yl]-1-methyl-1H-pyrazolo[3,4-d]pyrimidine;
  4-(3,3-difluoroazetidin-1-yl)-3-[5-(4-ethylphenyl)-1-methyl-1H-pyrazol-4-yl]-1-methyl-1 H-pyrazolo[3,4-d]pyrimidine;
  3-[5-(4-cyclopropylphenyl)-1-methyl-1H-pyrazol-4-yl]-4-(3,3-difluoroazetidin-1-yl)-1-methyl-1H-pyrazolo[3,4-d]pyrimidine; or
  3-{5-[4-(difluoromethyl)phenyl]-1-methyl-1H-pyrazol-4-yl}-4-(3-fluoroazetidin-1-yl)-1-methyl-1H-pyrazolo[3,4-d]pyrimidine,
or a pharmaceutically acceptable salt thereof.

17. A compound of Formula Id according to claim 15 wherein said compound is 1-methyl-3-[1-methyl-5-(4-methylphenyl)-1H-pyrazol-4-yl]-4-[(3S)-3-(piperidin-1-yl)pyrrolidin-1-yl]-1H-pyrazolo[3,4-d]pyrimidine, or a pharmaceutically acceptable salt thereof.

18. A pharmaceutical composition comprising a compound according to claim 1 or a pharmaceutically acceptable salt thereof and a pharmaceutically acceptable carrier.

19. A method for the treatment of cognitive impairment associated with schizophrenia, psychosis, schizophrenia, anxiety, depression, neuropathic pain, inflammatory pain, sepsis, or endotoxicosis in a human, comprising administering to said human a therapeutically effective amount of a compound according to claim 1 or a pharmaceutically acceptable salt thereof.

20. A method for inhibiting an activity of CYP3A4, comprising contacting the CYP3A4 with a compound of Formula Id according to claim 15 or a pharmaceutically acceptable salt thereof.

\* \* \* \* \*